(12) United States Patent
Gorodeski et al.

(10) Patent No.: US 8,314,068 B2
(45) Date of Patent: Nov. 20, 2012

(54) P2X$_7$ INHIBITION OF EPITHELIAL CANCERS AND PAPILLOMAS

(75) Inventors: George Gorodeski, Beachwood, OH (US); Wen Fu, Broadview Ht, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 337 days.

(21) Appl. No.: 12/554,444

(22) Filed: Sep. 4, 2009

(65) Prior Publication Data
US 2010/0130418 A1    May 27, 2010

(51) Int. Cl.
*A61P 35/00*   (2006.01)
*C07K 14/705*  (2006.01)

(52) U.S. Cl. .................. 514/18.9; 514/19.2; 514/19.3

(58) Field of Classification Search .................. None
See application file for complete search history.

*Primary Examiner* — Christine J Saoud
*Assistant Examiner* — Jon M Lockard
(74) *Attorney, Agent, or Firm* — Medlen & Carroll, LLP

(57) ABSTRACT

The present invention demonstrates that P2X$_7$ receptor induced apoptosis may be specific for cancerous cells. Treatment with the P2X$_7$ ligand BzATP, increased cellular apoptosis with no associated inflammatory changes or abnormal skin or systemic effects. In mice treated with DMBA/TPA, BzATP decreased papilloma skin formation. BzATP also induced involution of developed papillomas and stimulated apoptosis in keratinocytes outgrowing at the base of developed papillomas. These data show that (a) P2X$_7$ regulates apoptosis of epidermal cells; (b) in vivo, local administration of a drug that activates the P2X$_7$ receptor can inhibit development and progression of epidermal premalignant lesions.

14 Claims, 43 Drawing Sheets
(7 of 43 Drawing Sheet(s) Filed in Color)

P2X$_7$ INHIBITION OF EPITHELIAL CANCERS AND PAPILLOMAS

FIELD OF INVENTION

The present invention is related to the field of treatment and prevention of cancer. Cancer is believed to be a disease of overproliferation, wherein the present invention provides a method to reduce this overproliferation. For example, the methods herein result in the induction of intracellular apoptosis, thereby resulting in the prevention of cancerous growth and/or a reduction in cancer tumor size and number. The administration of a specific membrane receptor agonist (i.e., for example, a P2X$_7$ receptor agonist) is shown herein to reduce cancer growth and progression.

BACKGROUND

Cancer is a disease having many etiologies encompassing environmental toxins, disease, microbiological infections, and/or genetic predispositions. As such, each causative factor can, and does, result in a different type of cancer that usually manifests in a different biological tissue. As a result, no one therapeutic approach has been identified that has been effective at slowing or preventing the progression of a large percentage of different cancerous types. The only commonality that is currently recognized between all cancer diseases is manifested by an uncontrolled cellular growth rate.

Current theories related to epithelial cell growth predicts a regulatory pathway that balances the effects of mitogenic stimuli and apoptosis. Croker et al., "Cancer stem cells: implications for the progression and treatment of metastatic disease" *J Cell Mol Med* 2008, 12:374-390; and Rodriguez-Nieto et al., "Role of alterations in the apoptotic machinery in sensitivity of cancer cells to treatment" *Curr Pharm Des* 2006, 12:4411-4425. Apoptosis is believed to be a homeostatic process orchestrated by the host's genome of selective cell deletion without stimulating inflammatory response. Wyllie et al., "Cell death: the significance of apoptosis" *Int Rev Cytol* 1980, 68:251-306; Ellis et al., "Mechanisms and functions of cell death" *Annul Rev Cell Biol* 1991, 7:663-698; and Fawthrop et al., "Mechanisms of cell death" *Arch Toxicol* 1991, 65:437-444. Dysregulation of apoptotic cell-death has been implicated in states of disease and in the neoplastic transformation. Soti et al., "Apoptosis, necrosis and cellular senescence: chaperone occupancy as a potential switch" *Aging Cell* 2003, 2:39-45; and Renvoize et al., "Apoptosis: identification of dying cells" *Cell Biol Toxicol* 1998, 14:111-120. Present anti-cancer therapies all share a common problem in that normal non-cancerous cells are susceptible to the various treatments (i.e., for example, radiation and/or chemotherapy).

What is needed in the art is a single unified approach to cancer treatment that is directed at the common unifying mechanism of uncontrolled growth rates. One approach having a potential for success is related to re-balancing cell proliferation/apoptosis homeostasis such that apoptosis predominates, such that the cell proliferation/apoptosis homeostasis is not affected in non-cancerous tissues.

SUMMARY

The present invention is related to the field of treatment and prevention of cancer. Cancer is believed to be a disease of overproliferation, wherein the present invention provides a method to reduce this overproliferation. For example, the methods herein result in the induction of intracellular apoptosis, thereby resulting in the prevention of cancerous growth and/or a reduction in cancer tumor size and number. The administration of a specific membrane receptor agonist (i.e., for example, a P2X$_7$ receptor agonist) is shown herein to reduce cancer growth and progression.

In one embodiment, the present invention contemplates a method for treating cancer comprising administering a P2X$_7$ agonist (i.e., for example, 3'-O-(4-benzoylbenzoyl)adenosine triphosphate; BzATP). In one embodiment, the P2X$_7$ agonist activates apoptosis. In one embodiment, the cancer comprises a papilloma. In one embodiment, the cancer comprises an epithelial cancer. In one embodiment, the apoptosis is activated in the papilloma. In one embodiment, the apoptosis is activated in the epithelial cancer. In one embodiment, the apoptosis is not activated in non-cancerous tissue.

In one embodiment, the present invention contemplates a method, comprising: a) providing: i) a subject comprising a plurality of malignant cancer cells and a plurality of non-cancer cells; ii) a P2X$_7$ receptor agonist capable of inducing apoptosis in said cancer cells; b) administering said agonist to said cancer cells under conditions such that apoptosis is induced. In one embodiment, the agonist comprises BzATP. In one embodiment, the apoptosis kills the cancer cell. In one embodiment, the agonist does not induce apoptosis in the non-cancerous cells. In one embodiment, The administering is selected from the group consisting of intradermal, intratumoral, transdermal, intraperitoneal, intranasal, intravenous, intramuscular, and subcutaneous. In one embodiment, the administering further comprises TNFα. In one embodiment, the cancer cell is derived from an epithelial cell. In one embodiment, the cancer cell comprises a squamous cell carcinoma. In one embodiment, the cancer cell comprises a P2X$_7$ receptor. In one embodiment, the non-cancer cell comprises a P2X$_7$ receptor.

In one embodiment, the present invention contemplates a method, comprising: a) providing: i) a subject at risk for developing a plurality of benign cancer cells; ii) a P2X$_7$ receptor agonist capable of inducing apoptosis in said cancer cells; b) administering said agonist to said subject under conditions such that apoptosis is induced, thereby preventing the development of said cancer cells. In one embodiment, the agonist comprises BzATP. In one embodiment, the apoptosis kills said developing cancer cell. In one embodiment, the administering is selected from the group consisting of intradermal, intratumoral, transdermal, intraperitoneal, intranasal, intravenous, intramuscular, and subcutaneous. In one embodiment, the administering further comprises TNFα. In one embodiment, the developing cancer cell is derived from an epithelial cell. In one embodiment, the developing cancer cell comprises a papilloma. In one embodiment, the subject further comprises a plurality of non-cancerous cells. In one embodiment, the agonist does not induce apoptosis in the non-cancerous cells. In one embodiment, the cancer cell comprises a P2X$_7$ receptor. In one embodiment, the non-cancerous cell comprises a P2X$_7$ receptor.

In one embodiment, the present invention contemplates a method of treating and/or preventing cancer by administering compounds capable of binding to a P2X$_7$ receptor gene enhancer region, wherein the enhancer region increases P2X$_7$ receptor expression. In one embodiment, the P2X$_7$ gene comprises an enhancer region (i.e., for example, +222/+232). In one embodiment, the compounds modulate P2X$_7$ receptor expression regulator proteins. In one embodiment, the regulator proteins may be selected from the group including, but not limited to, p300, Elk-1, E47, E11aE, E2F, or p53. In one embodiment, a sequence of the putative enhancer region +222/+232 comprises binding sites for regulator proteins selected from the group including, but not limited to, p300, Elk-1, E47, E11aE, E2F, or p53.

DEFINITIONS

The term "cancer", as used herein refers to any presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemia cells. The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The term "inhibit the proliferation of a cancer cell" as used herein, means to kill a cancer cell, or permanently or temporarily arrest or slow the growth of a cancer cell. Inhibition of cancer cell proliferation can be inferred if the number of cancer cells in a subject remains constant or decreases after administration of a miRNA gene product and/or an miRNA gene expression-inhibiting compound. An inhibition of cancer cell proliferation can also be inferred if the absolute number of such cells increases, but the rate of tumor growth decreases.

The term "detecting" as used herein, refers to obtaining indirect evidence regarding the likelihood of the presence of a pathophysiological condition or assessing the predisposition of an organism to the development of the pathophysiological condition (i.e., for example, epithelial cancer).

The term "diagnosing" as used herein, refers to establishing scientific evidence demonstrating the actual presence of a pathophysiological condition (i.e., for example, epithelial cancer).

The term "tumor" or "papilloma" as used herein, refers to all neoplastic cell growth and proliferation, whether malignant or benign, and all precancerous and cancerous cells and tissues. The size of a tumor can be ascertained by direct visual observation, or by diagnostic imaging methods, including, but not limited to, X-ray, magnetic resonance imaging, ultrasound, and scintigraphy. Diagnostic imaging methods used to ascertain size of the tumor can be employed with or without contrast agents. The size of a tumor can also be ascertained by physical means, such as palpation of the tissue mass or measurement of the tissue mass with a measuring instrument, such as a caliper.

The term "precancerous" as used herein, refers to cells or tissues having characteristics relating to changes that may lead to malignancy or cancer. Examples include, but are not limited to, adenomatous growths in uterus, skin, colon, ovary, breast, or prostate. Examples also include, abnormal neoplastic, in addition to dysplastic nevus syndromes, polyposis syndromes, prostatic dysplasia, and other such neoplasms, whether the precancerous lesions are clinically identifiable or not.

The term "tumor-cell killing" as used herein, refers to any inhibition of tumor cell proliferation by means of blocking a function or binding to block a pathway related to tumor-cell proliferation. For example, inhibition of an mRNA (i.e., for example, $P2X_7$ mRNA) may block a pathway resulting in tumor-cell proliferation.

The term "anti-$P2X_7$ antibody" as used herein, refers to any antibody or antibody fragment that specifically binds a polypeptide encoded by a $P2X_7$ gene, mRNA, cDNA, or a subsequence thereof. These antibodies can mediate anti-proliferative activity on tumor-cell growth.

The term "immunoassay" as used herein, refers to any assay that utilizes the binding interaction between an antibody and an antigen. Typically, an immunoassay uses the specific binding properties of a particular antibody to isolate, target, and/or quantify the antigen.

The term "specifically (or selectively) binds to an antibody" or "specifically (or selectively) immunoreactive with" as used herein, when referring to a protein or peptide, refers to any binding reaction that is determinative of the presence of the protein in a heterogeneous population of proteins and other biologics. For example, under designated immunoassay conditions, specified antibodies bind to a particular protein at a level at least two times the background and do not substantially bind in a significant amount to other proteins present in the sample. Specific binding to an antibody under such conditions may require an antibody that is selected for its specificity for a particular protein. For example, antibodies raised to a particular $P2X_7$ polypeptide can be selected to obtain only those antibodies that are specifically immunoreactive with a $P2X_7$ polypeptide, and not with other proteins, except for polymorphic variants, orthologs, and alleles of a specific $P2X_7$ polypeptide.

The term "cancer symptoms" as used herein, refers to observable changes in a subject's physical and/or medical condition consistent with a specific type of cancer. In general, cancer symptoms may include, but are not limited to, weight loss, fatigue, localized swelling, or localized pain. Each cancer type comprises symptoms that may or may not occur in a different type of cancer. For example, symptoms of uterine cancer include, but are not limited to, abnormal bleeding, spotting, or other discharges from the vagina. On the other hand, symptoms of cervical cancer include, but are not limited to, continuous vaginal discharge, abnormal and/or heavy vaginal bleeding, loss of appetite, pelvic and/or back pain, single swollen leg, or bone fractures.

The term "suspected" or "suspecting" as used herein, refers to a medical deduction based upon the observance of cancer symptoms concluding that a subject (i.e., for example, a patient and/or mammal) may have contracted a disease or other medical condition (i.e., for example, cancer).

The term "in need of a diagnosis" as used herein, refers to a patient or subject (i.e., for example, a mammal) comprising at least one hypermethylated gene region (i.e., for example, a hypermethylated $P2X_7$ gene region).

The term "in need of a treatment" as used herein, refers to a patient or subject (i.e., for example, a mammal) having been diagnosed with a disease or other medical condition (i.e., for example, cancer).

The term "local" as used herein, refers to the non-parenteral administration of a therapeutic agent. A local administration may include, but is not limited to topical or intratumoral. A minimal amount of systemic distribution is expected during a local administration but would be expected to maintain subclinical thresholds.

The term "detecting" as used herein, refers to obtaining indirect evidence regarding the likelihood of the presence of a disease and/or assessing the predisposition of an organism to the development of the disease (i.e., for example, uterine cancer).

The term "diagnosing" as used herein, refers to establishing scientific evidence demonstrating the actual presence of a disease (i.e., for example, uterine cancer).

The term "tumor" as used herein, refers to all neoplastic cell growth and proliferation, whether malignant or benign, and all precancerous and cancerous cells and tissues. The size of a tumor can be ascertained by direct visual observation, or by diagnostic imaging methods, including, but not limited to, X-ray, magnetic resonance imaging, ultrasound, and scintigraphy. Diagnostic imaging methods used to ascertain size of the tumor can be employed with or without contrast agents. The size of a tumor can also be ascertained by physical means, such as palpation of the tissue mass or measurement of the tissue mass with a measuring instrument, such as a caliper.

The term "precancerous" as used herein, refers to cells or tissues having characteristics relating to changes that may lead to malignancy or cancer. Examples include, but are not limited to, adenomatous growths in uterus, skin, colon, ovary, breast, or prostate. Examples also include, abnormal neoplastic, in addition to dysplastic nevus syndromes, polyposis syndromes, prostatic dysplasia, and other such neoplasms, whether the precancerous lesions are clinically identifiable or not.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc) to a binding partner under conditions such that the binding partner becomes unresponsive to its natural ligands Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "medium" as used herein, refers to any material, or combination of materials, which serve as a carrier or vehicle for delivering of a drug to a treatment point (e.g., wound, surgical site etc.). For all practical purposes, therefore, the term "medium" is considered synonymous with the term "carrier". It should be recognized by those having skill in the art that a medium comprises a carrier, wherein said carrier is attached to a drug or drug and said medium facilitates delivery of said carrier to a treatment point. Further, a carrier may comprise an attached drug wherein said carrier facilitates delivery of said drug to a treatment point. Preferably, a medium is selected from the group including, but not limited to, foams, gels (including, but not limited to, hydrogels), xerogels, microparticles (i.e., microspheres, liposomes, microcapsules etc.), bioadhesives, or liquids. Specifically contemplated by the present invention is a medium comprising combinations of microparticles with hydrogels, bioadhesives, foams or liquids. Preferably, hydrogels, bioadhesives and foams comprise any one, or a combination of, polymers contemplated herein. Any medium contemplated by this invention may comprise a controlled release formulation. For example, in some cases a medium constitutes a drug delivery system that provides a controlled and sustained release of drugs over a period of time lasting approximately from 1 day to 6 months.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded as biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "bioerodible" as used herein, refers to any material that is mechanically worn away from a surface to which it is attached without generating any long term inflammatory effects such that the molecular structure has not been altered. In one sense, bioerosin represents the final stages of "biodegradation" wherein stable low molecular weight products undergo a final dissolution.

The term "bioresorbable" as used herein, refers to any material that is assimilated into or across bodily tissues. The bioresorption process may utilize both biodegradation and/or bioerosin.

The term "biostable" as used herein, refers to any material that remains within a physiological environment for an intended duration resulting in a medically beneficial effect.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "a cell comprising a $P2X_7$ receptor" as used herein, refers to any cell derived from a bodily tissue displaying a $P2X_7$ receptor. wherein activation of the receptor induces apoptosis. For example, such cell include, but are not limited to, epithelial cells, neuronal cells, glial cells, endothelial cells, bone marrow cells, muscle cells, hemopoietic cells, white blood cells, gastrointestinal cells, urinary tract cells, gonadal cells, renal cells, pancreatic cells, retinal cells, prostate cells, lung cells, or kidney cells.

BRIEF DESCRIPTION OF THE FIGURES

The file of this patent contains at least one drawing executed in color. Copies of this patent with color drawings will be provided by the Patent and Trademark Office upon request and payment of the necessary fee.

Micrographs a and b: $P2X_7$ mRNA in-situ hybridization of human normal keratinocytes; a anti-sense probe, b sense probe (×10).

Micrographs c and d (×40): $P2X_7$ immunostains of cultured human normal keratinocytes (c) and SCC-9 cells (d); arrows point to cells membranes. In c and d the immunoreactivity to the anti-$P2X_7$ antibody was blocked by pre-incubation with the $P2X_7$ antigen (not shown).

Micrograph e: Quantitative analysis of $P2X_7$ immunostaining (empty bars) and $P2X_7$ mRNA qPCR (normalized to E-Cadherin mRNA, filled bars) in human normal keratinocytes (K) and SCC-9 (S-9) cells (means±SD, n=3); *-p<0.01.

Insert in e: Effects of treatments with ATP on apoptosis. Human normal keratinocytes (K) and SCC-9 (S-9) cells were treated with 250 μM ATP for 8 hrs; Control—no treatment. Shown are means±SD of 3 experiments. * and -p<0.03-0.01 compared to k; *-p<0.01 compared to control. AU—arbitrary units.

Micrographs f and g: Cross-sections (×10) of mouse dorsal skin; f-$P2X_7$ immunostain, g-phase. The vertical arrow in f points the epidermis and the horizontal arrow points a hair shaft.

Figure 2:
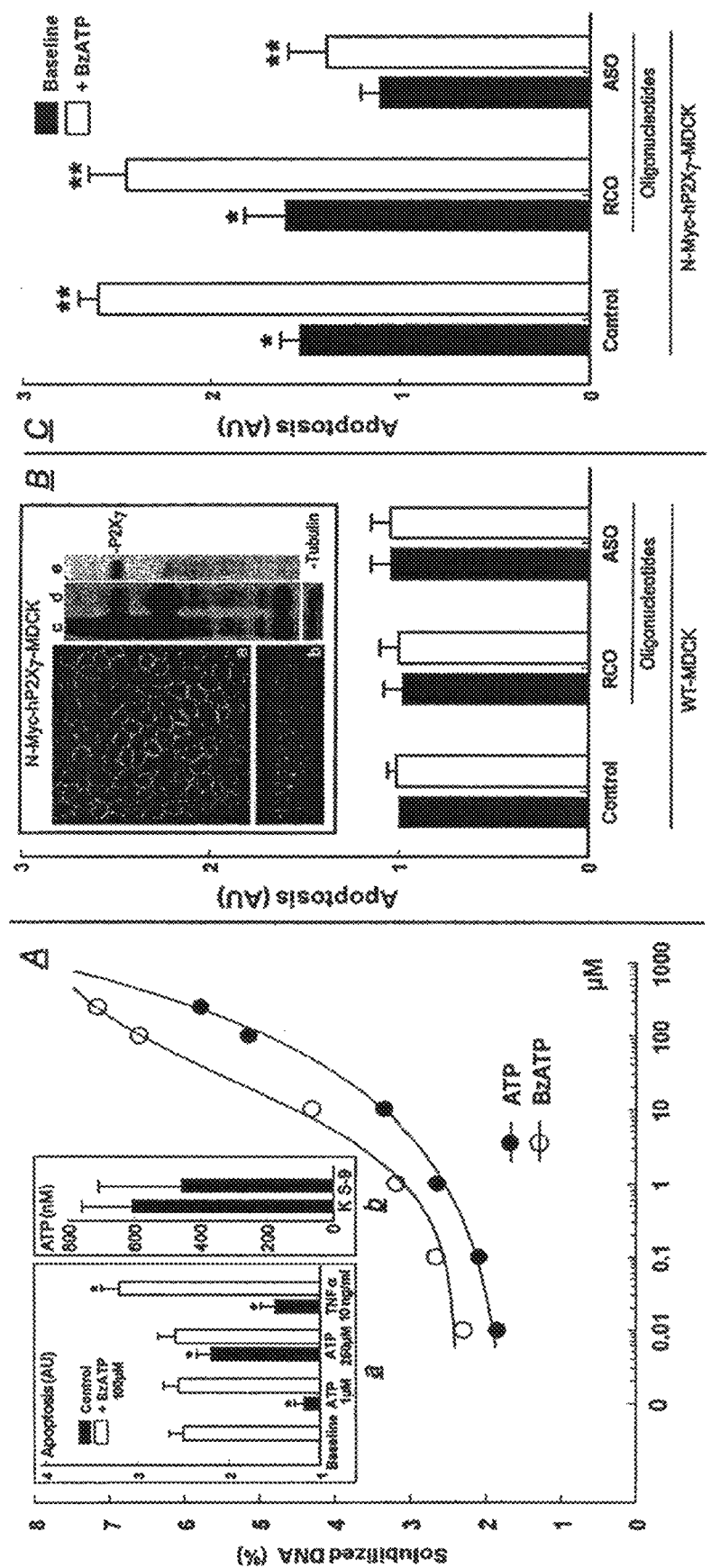

FIG. 2A presents exemplary data showing apoptosis dose-related effects of ATP and BzATP in human normal keratinocytes (means of 3 experiments, variability ranged 3-8%).

Insert a: Effects on apoptosis of treatments with ATP, BzATP, and TNFα, alone or in combination (means±SD, n=3-5). Data were normalized to apoptosis level (=1) in non-treated cells (Baseline condition). *-p<0.01.

Insert b: Steady-state levels of ATP in conditioned media of cultured human normal keratinocytes (K) and SCC-9 (S-9) cells (means±SD, n=3).

FIGS. 2B and 2C present exemplary data showing heterologous expression in MDCK cells of the human full-length $P2X_7$ cDNA (Myc-tagged at the N-terminus), and effects of treatments on baseline and of BzATP-induced apoptosis (100 μM, 8 hrs). Cells were also co-treated with the vehicle (Control); with anti-sense $P2X_7$ oligonucleotides (ASO), or with random-control $P2X_7$ oligonucleotides (RCO) (means±SD, n=3). WT—wild-type.

Insert: $P2X_7$ immunoreactivity in N-Myc-hP2X7-MDCK cells captured by laser confocal microscopy at the planar (a) and vertical (b) axes.

FIGS. 2C-2E present exemplary data showing Western immunoblots of lysates obtained from N-Myc-hP2X7-MDCK cells treated with the random-control $P2X_7$ oligonucleotides (RCO) (c) or with the anti-sense $P2X_7$ oligonucleotides (ASO) (d and e) (n=3). The c and d lanes represent gel blotted initially with the anti Myc antibody and reprobed with the anti $P2X_7$ antibody. Experiments were repeated 3 times with similar results. * and **-p<0.01 compared to WT-MDCK. AU—arbitrary units.

Figure 3:
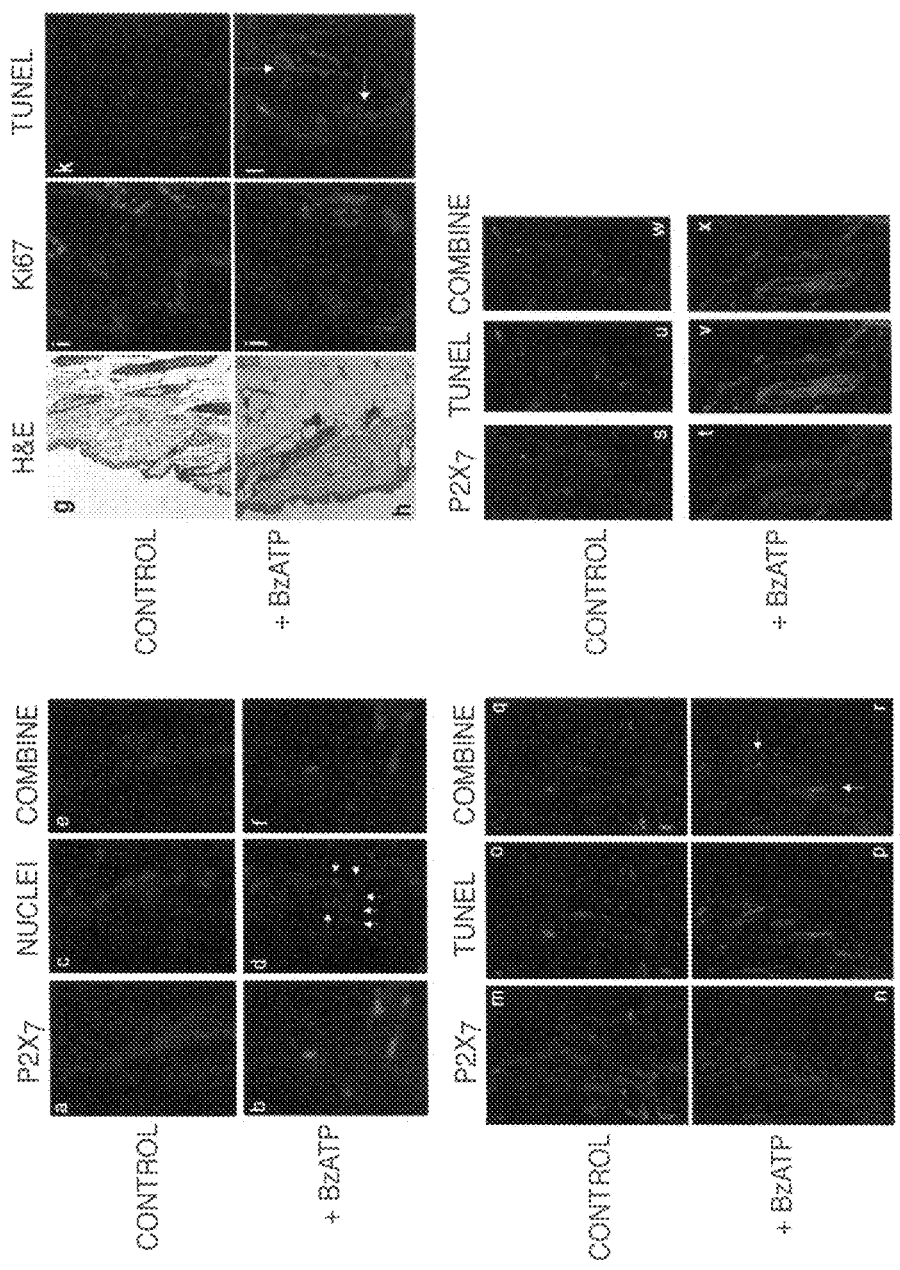

FIG. 3 presents exemplary data showing BzATP effects in vivo on epidermal apoptosis.

FIGS. 3A-F: Experiment 1: Cross-sections (×40) taken from the anterior (Control) and posterior (BzATP-treated) regions of the dorsal skin of the same mouse. Sections were immunostained with anti-$P2X_7$ antibody and co-stained with DAPI for nuclear morphology. Arrows in d point to nuclei of $P2X_7$-positive epidermal cells in basal/parabasal regions of the epidermis at stages of condensation, fragmentation and pyknosis.

Figures G-L: Experiment-2: Cross-sections (×10) were either stained with H&E (g,h), immunostained with anti-Ki67 antibody (i,j), or stained for TUNEL (apoptosis) (k,l). Arrows in l point to increased TUNEL staining in BzATP-treated cells in basal/parabasal layers of the epidermis (horizontal arrow) and in a hair shaft (vertical arrow).

Figures M-X: Experiment-2: Cross-sections (m-r, x10; s-x x20) immunostained with anti-$P2X_7$ antibody and co-stained for TUNEL (apoptosis). Arrows in r show co-localization of $P2X_7$ immunoreactivity with TUNEL in epidermal cells in the basal/parabasal layers (horizontal arrow) and in a hair shaft (vertical arrow) of BzATP-treated animals. Experiments were repeated 3-5 times with similar results. Panel x shows enhanced TUNEL staining co-localized with $P2X_7$ immunoreactivity in epidermal cells from BzATP-treated animal in the basal/parabasal layers and in a hair shaft. Experiments were repeated 3-5 times with similar results.

Figure 4:
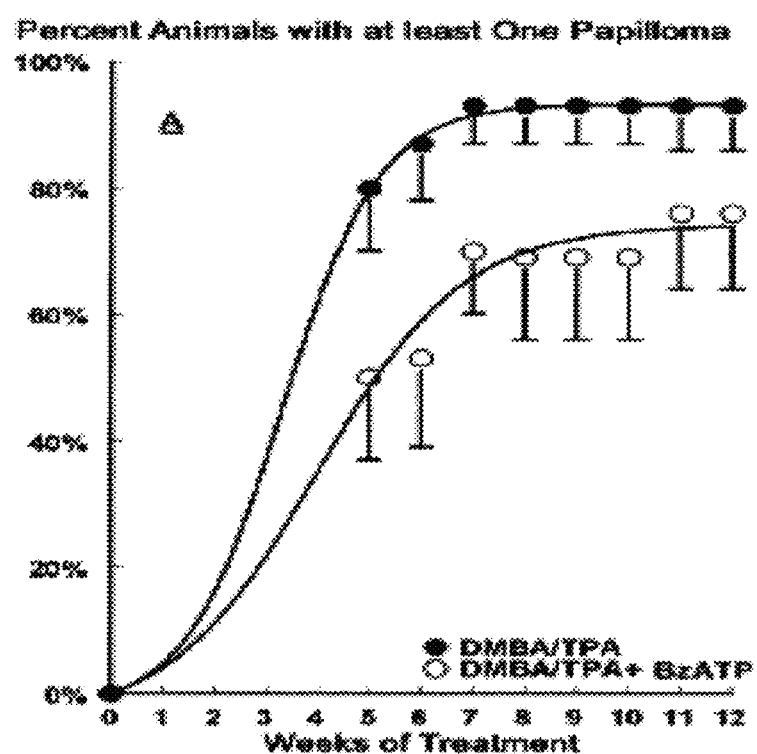
Figure 4:
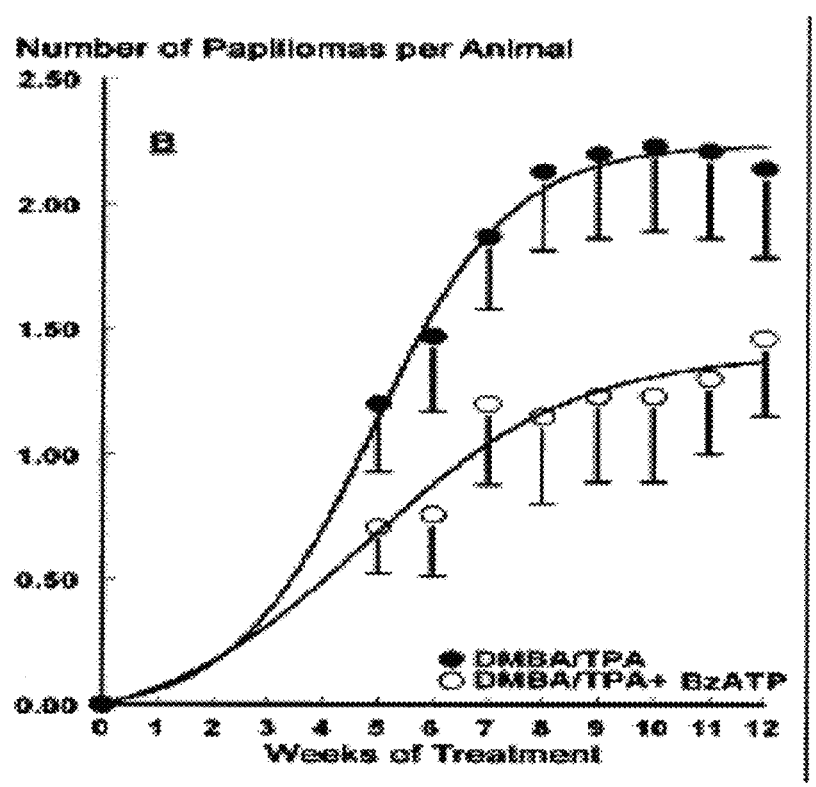
Figure 4:
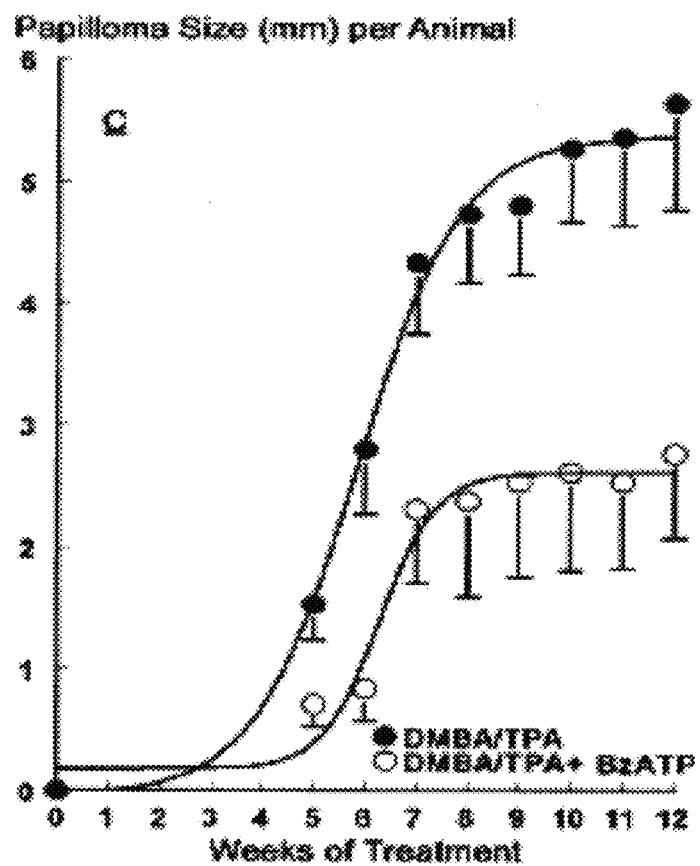

FIG. 4 present exemplary data showing BzATP effects on skin papilloma formation in DMBA/TPA-treated mice. Treatments are described herein as Experiment-3. Shown are means (±SEM) of data obtained in the DMBA/TPA group (filled circles, n=15) and in the DMBA/TPA+BzATP group (empty circles, n=14).

FIG. 4A: Percent animals with at least one papilloma.
FIG. 4B: Number of papillomas per animal.
FIG. 4C: Mean papilloma size (mm [largest lesion dimension]).

Figure 5:
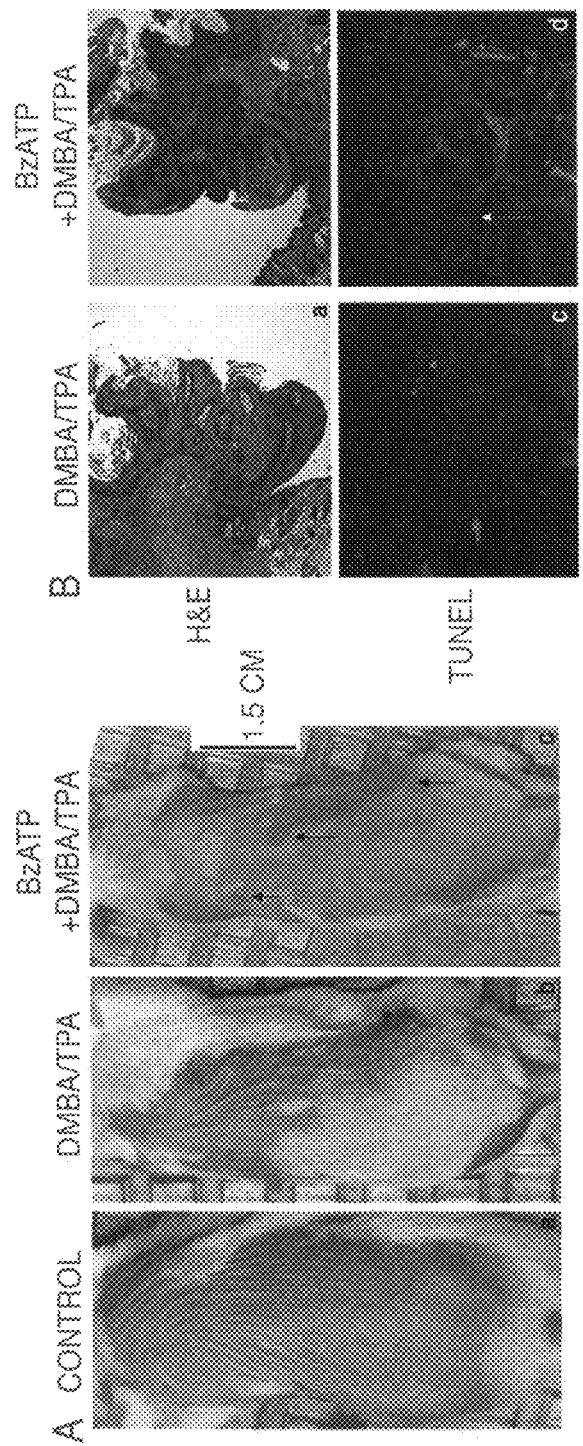

FIG. 5 presents illustrative photographs of gross morphology of skin papillomas in DMBA/TPA− and in DMBA/TPA+ BzATP-treated mice following treatments described herein as Experiment-3. Arrows in c point to papillomas at various stages of involution. FIGS. 5A and 5B represent hematoxylin/eosin (H&E) staining. FIGS. 5C and 5B represent TUNEL staining (c,d) (×10). Arrow in d points to increased TUNEL staining in basal/parabasal layers of outgrowing keratinocytes in the papilloma.

Figure 6:
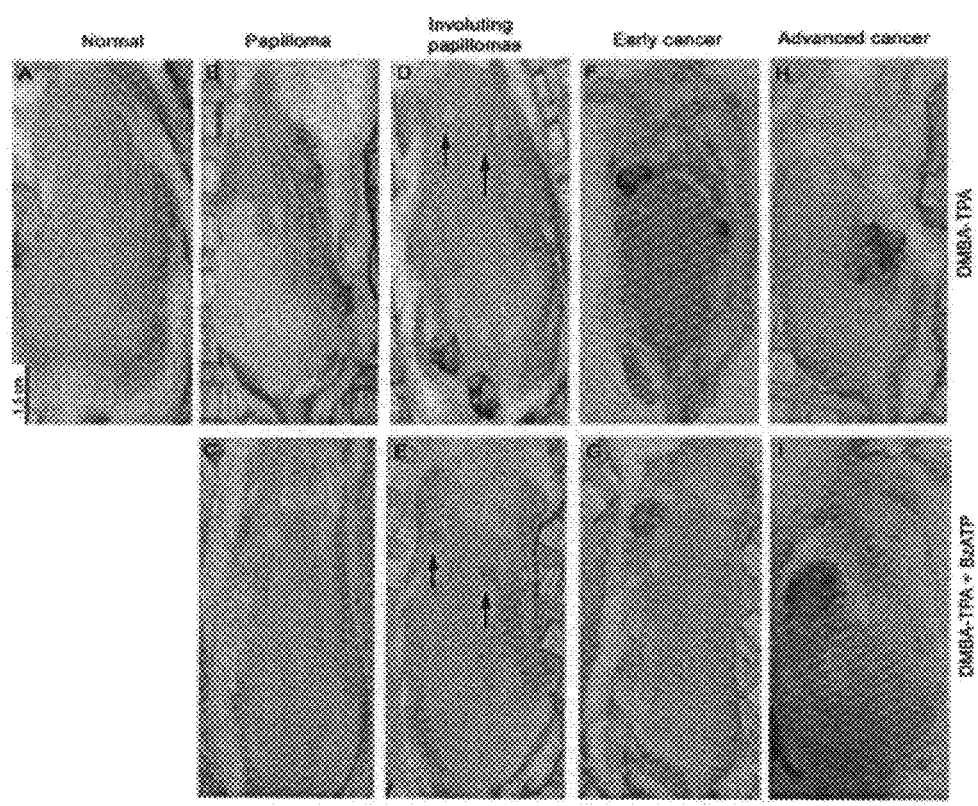

FIG. 6 presents representative photographs of DMBA/TPA-induced skin lesions in mice in-vivo, and the effects of co-treatment with BzATP. Arrows in D and E point to involuting papillomas. Treatments are described herein as Experiment-4.

Figure 7:
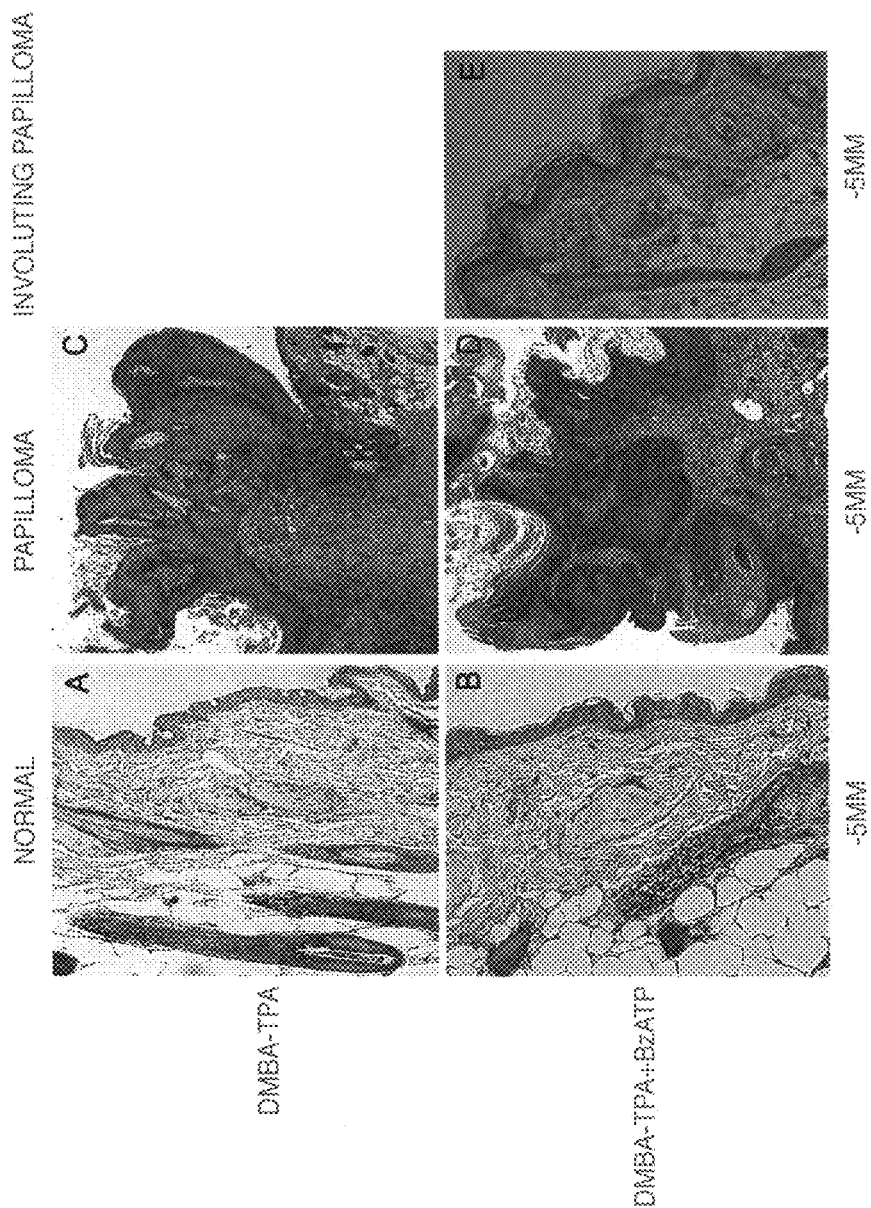
Figure 7:
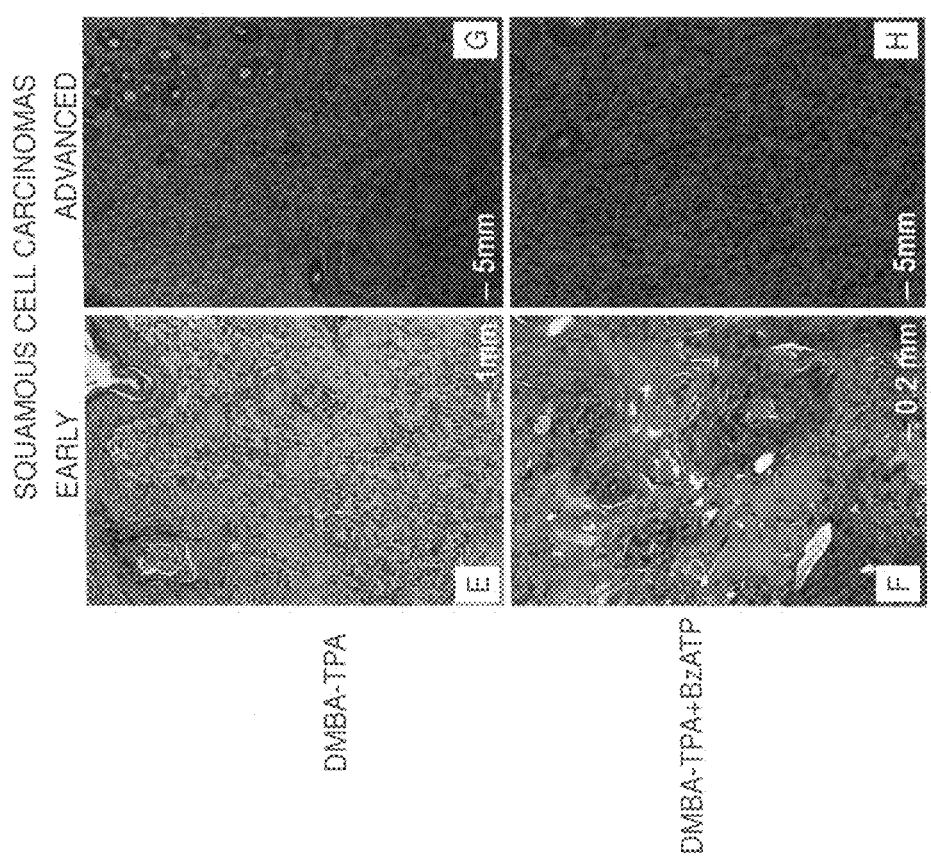

FIG. 7 presents representative histological cross-sections, evaluated histologically by H&E staining, of DMBA/TPA-induced skin lesions in mice in-vivo, and the effects of co-treatment with BzATP.

Figure 8:
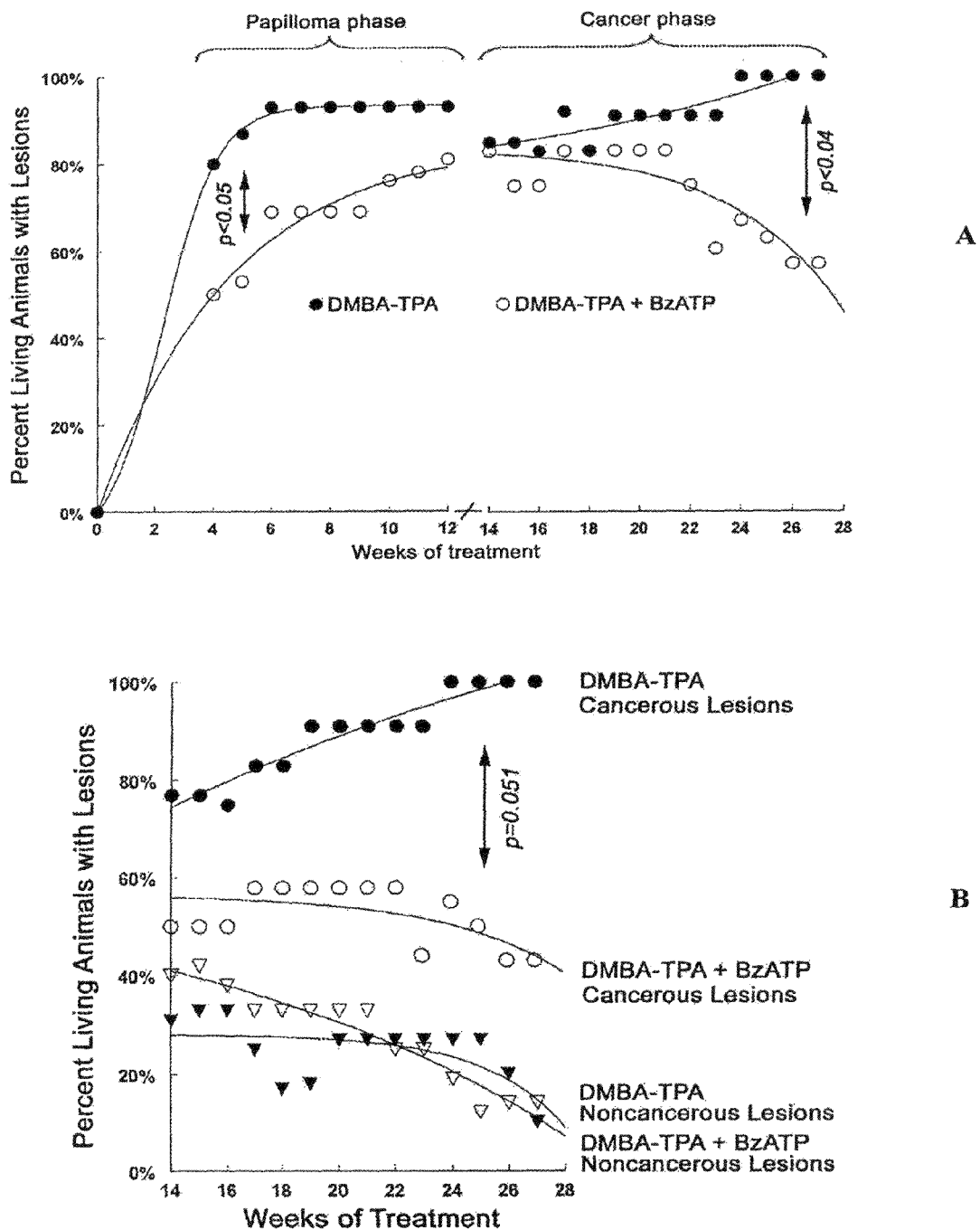

FIG. 8 presents exemplary data showing a summary of the effects of local treatments with DMBA/TPA (black symbols) or DMBA/TPA+BzATP (white symbols) on the proportion of living mice with skin lesions. Treatment is described herein as Experiment-4. (expressed as mean data; standard deviation (SD) ranges between 3-11%).

FIG. 8A: Skin lesions at 0-12 weeks of treatment were papillomas. Skin lesions at 14-28 weeks of treatment were grouped either as cancerous lesions (squamous spindle-cell carcinomas, circles), or as non-cancerous lesions (existing or involuting papillomas, triangles).

FIG. 8B: Skin lesions at 14-28 weeks of treatment were grouped either as cancerous lesions (squamous spindle-cell carcinomas, circles), or as non-cancerous lesions (existing or involuting papillomas, triangles).

Figure 9:
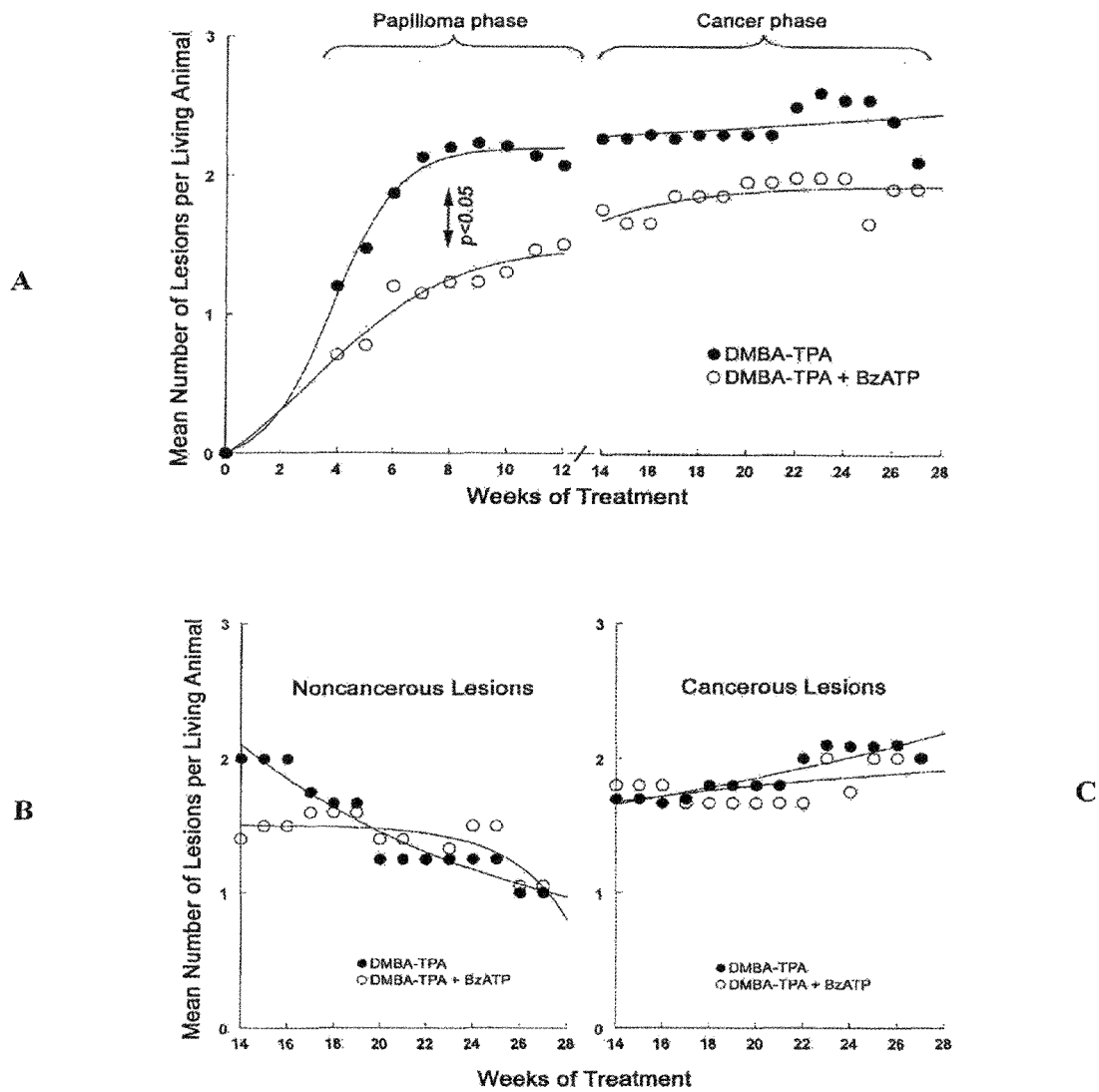

FIGS. 9A-9C present exemplary data showing a summary of the effects of local treatments with DMBA/TPA (black symbols) or DMBA/TPA+BzATP (white symbols) on the mean number of skin lesions per living animal. Treatments are described herein as Experiment-4. Values represent means, and standard deviations ranged between 5-9%.

Figure 10:
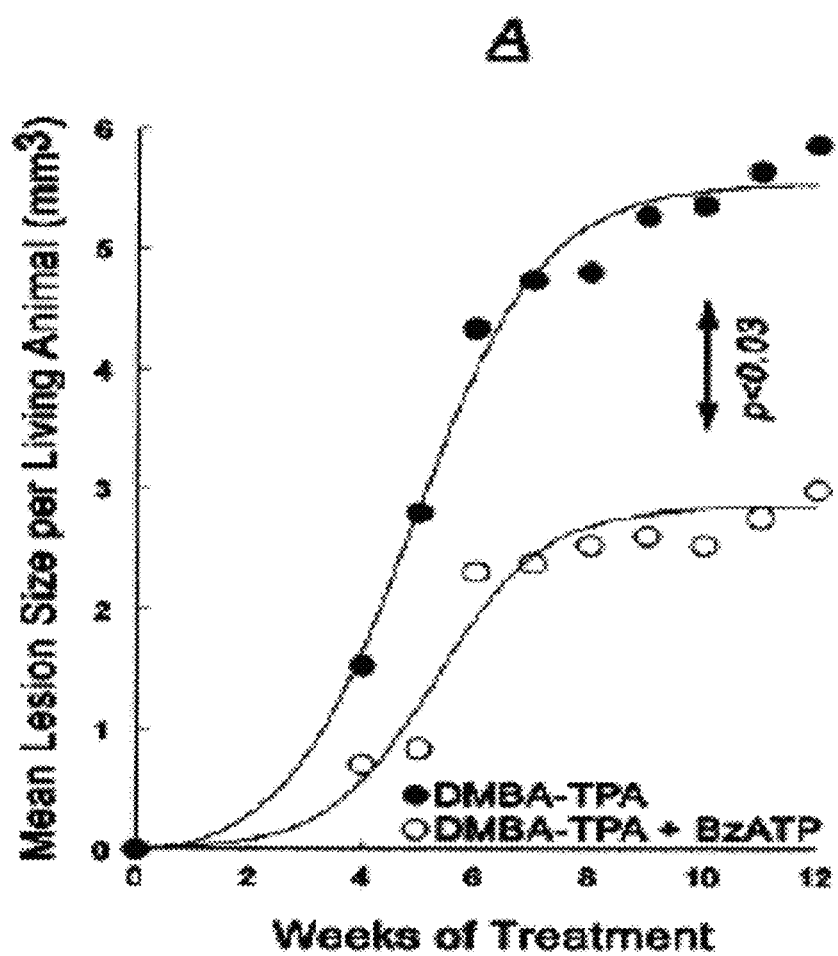
Figure 10:
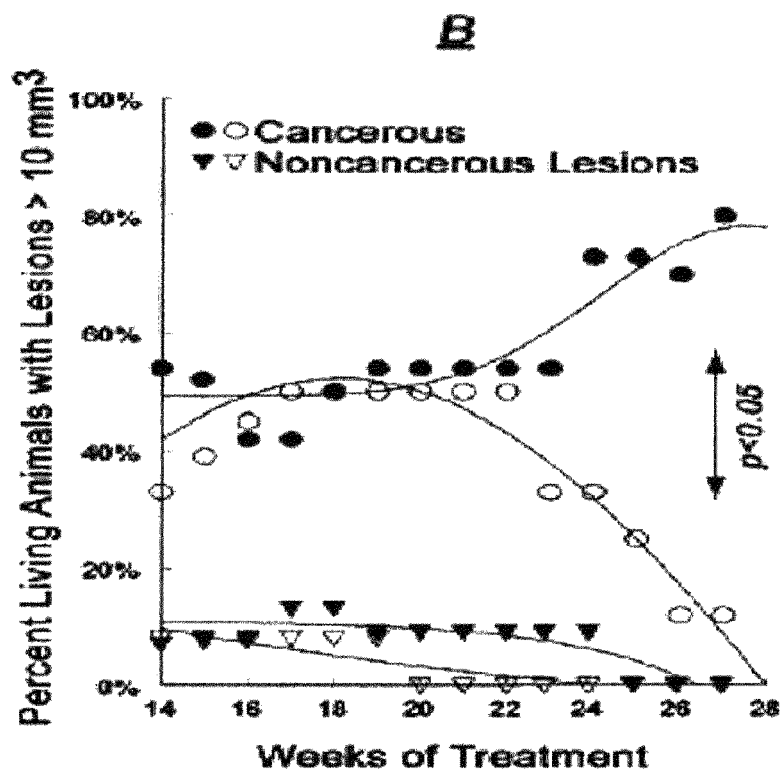
Figure 10:
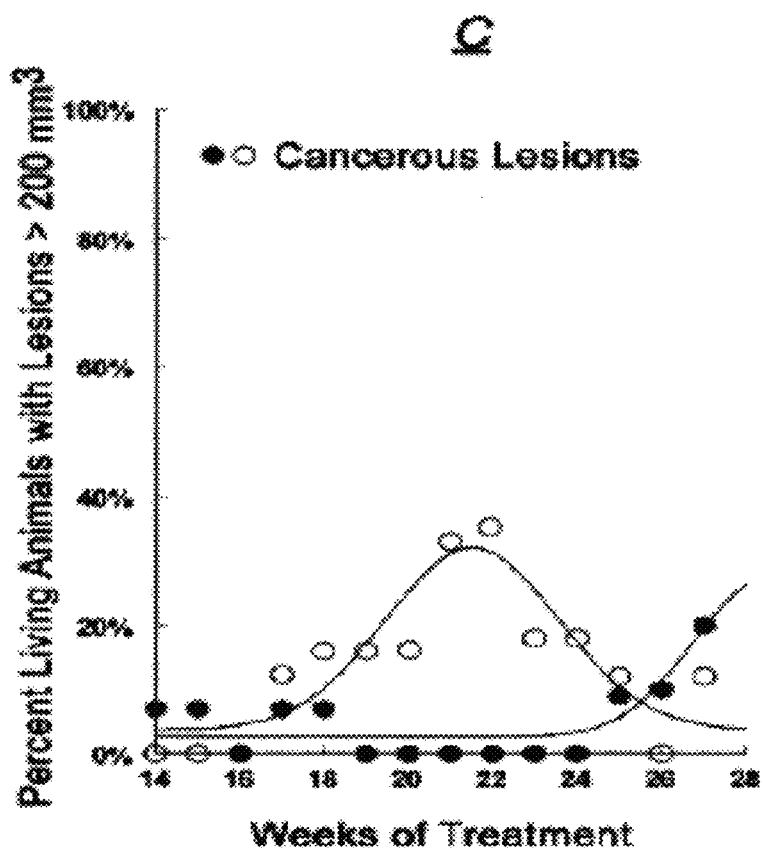

FIG. 10 presents exemplary data showing a summary of the effects of local treatments with DMBA/TPA (black symbols) or DMBA/TPA+BzATP (white symbols). Treatments are described herein as Experiment-4. Values represent means, and standard deviations ranged between ranged 2-18%.

FIG. 10A: Mean lesion size between 0-12 weeks.

FIG. 10B: Proportion of living mice with total lesions volume per animal of >10 $mm^3$ FIG. 10C: Proportion of living mice with total lesions volume per animal of >200 $mm^3$.

Figure 11:
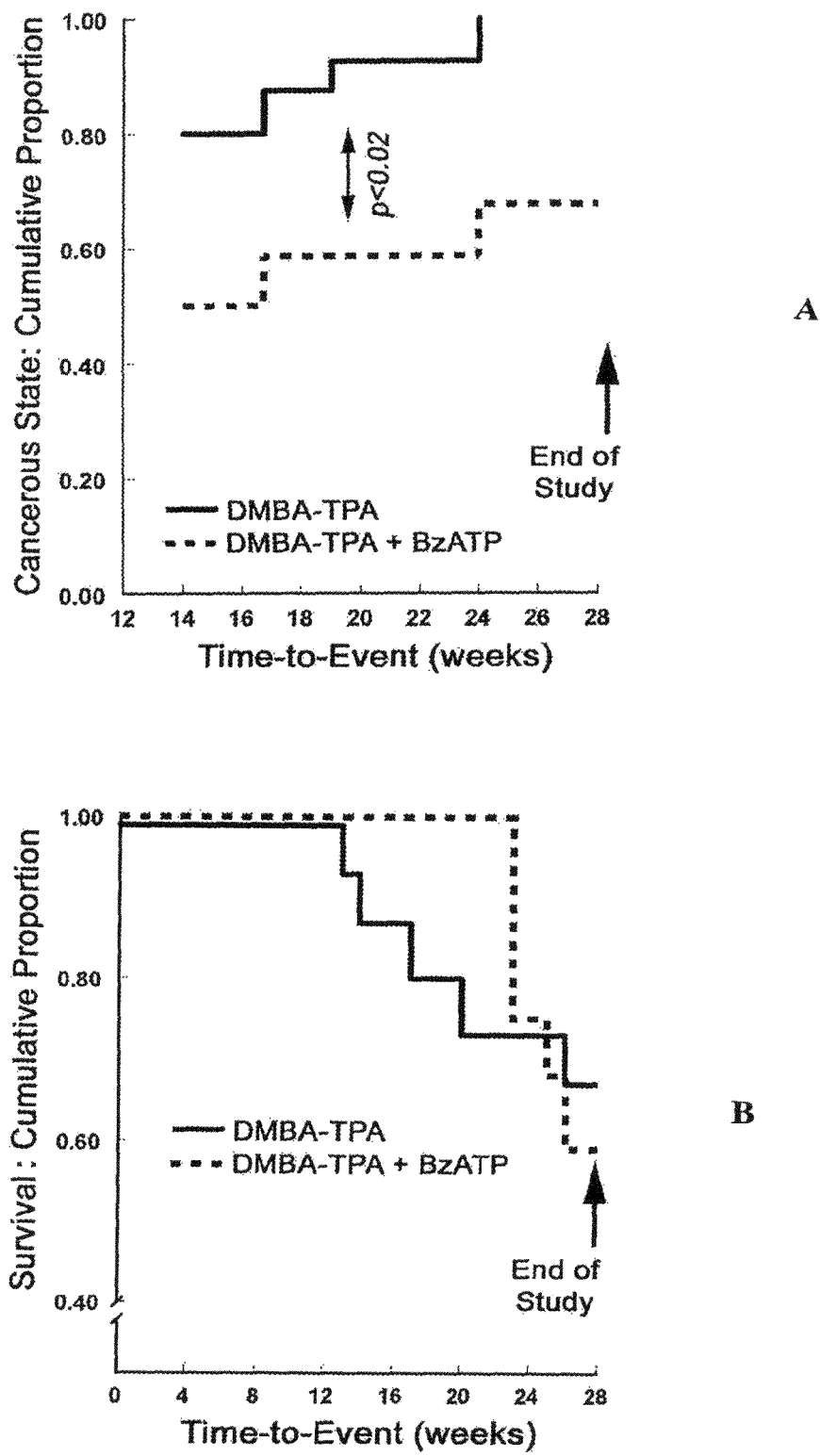

FIG. 11 presents exemplary data showing a summary of the effects of local treatments with DMBA/TPA (black symbols) or DMBA/TPA+BzATP (white symbols). Treatments are described herein as Experiment-4.

FIG. 11A: Time-to-event of cancer state.

FIG. 11B: Survival rates.

Figure 12:
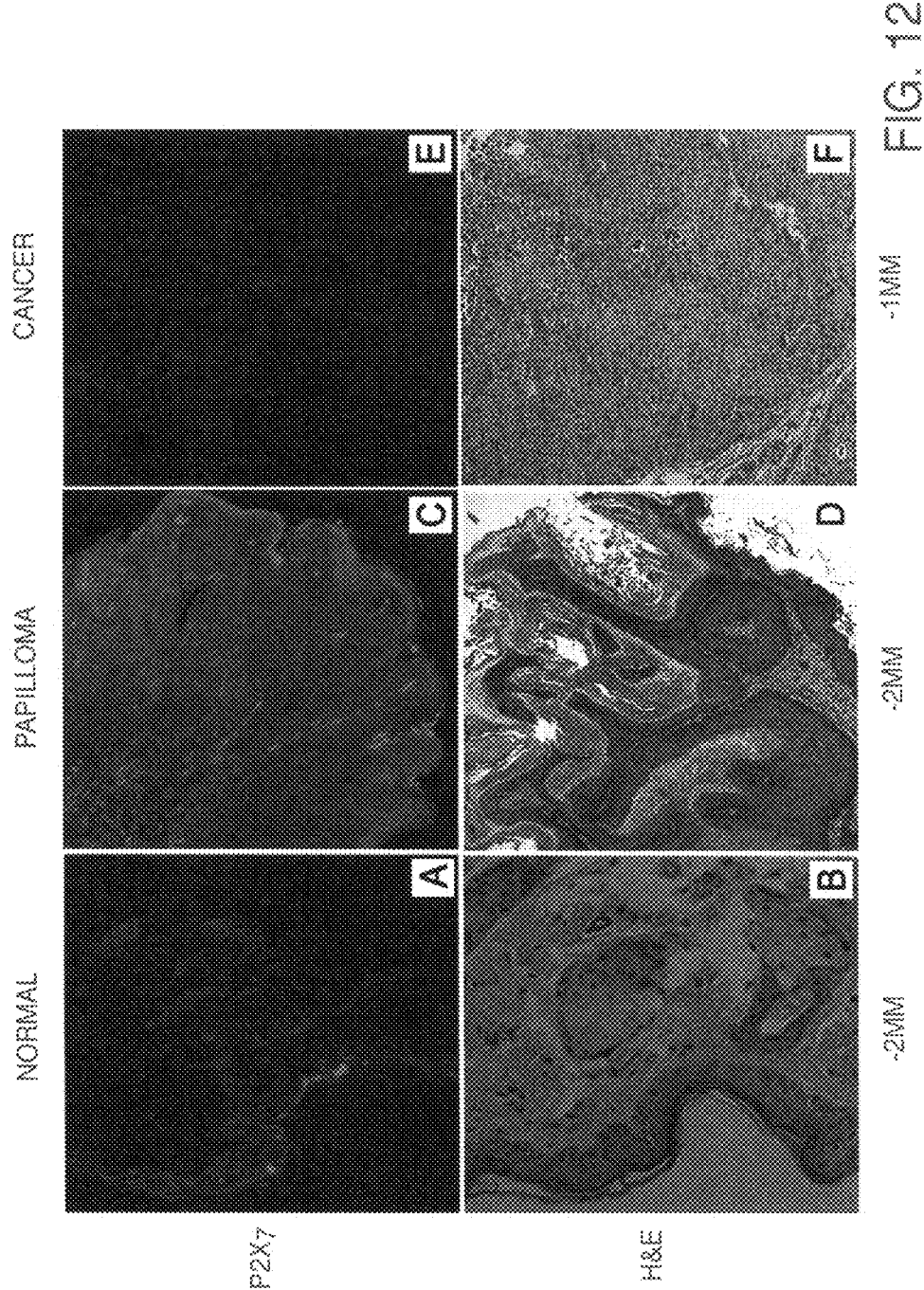

FIG. 12 presents exemplary data showing $P2X_7$ immunoreactivity in mice. Treatments are described herein as Experiment-4.

FIG. 12A: Normal epidermis.

FIG. 12B: An H&E stained parallel cross section of a normal epidermis.

FIG. 12C. Papilloma epidermis.

FIG. 12D: An H&E stained parallel cross section of a papilloma epidermis.

FIG. 12E: Cancerous epidermis.

FIG. 12F: An H&E stained parallel cross section of a cancerous epidermis.

FIG. 12G: Analysis of $P2X_7$ immunoreactivity compared among paired histologically normal and cancerous tissues. Bars are means (±SD) of levels in tissues of five mice. Normal tissue data was normalized in each case to an arbitrary value of 10. *-p<0.01. AU—arbitrary units.

FIG. 12H: $P2X_7$ protein assays in mouse normal and cancer skin tissues. Lysates fractionated by gel electrophoresis were immunoblotted with the anti-$P2X_7$ antibody and membranes were re-probed with the anti-GAPDH antibody. Normal tissue data was normalized in each case to an arbitrary value of 10. *-p<0.01. AU—arbitrary units.

Insert: Western immunoblot of lysates of histologically normal and cancerous tissues obtained from the same animal. Similar results were obtained in tissues of two additional mice. Bars show means (±SD) of densitometry results of the $P2X_7$-specific 75 KDa bands in tissues of three mice.

FIG. 12I: $P2X_7$ mRNA levels (relative to GAPDH mRNA) (means±SD) in histologically normal and cancerous tissues obtained from three animals. Normal tissue data was normalized in each case to an arbitrary value of 10. *-p<0.01. AU—arbitrary units.

Figure 13:
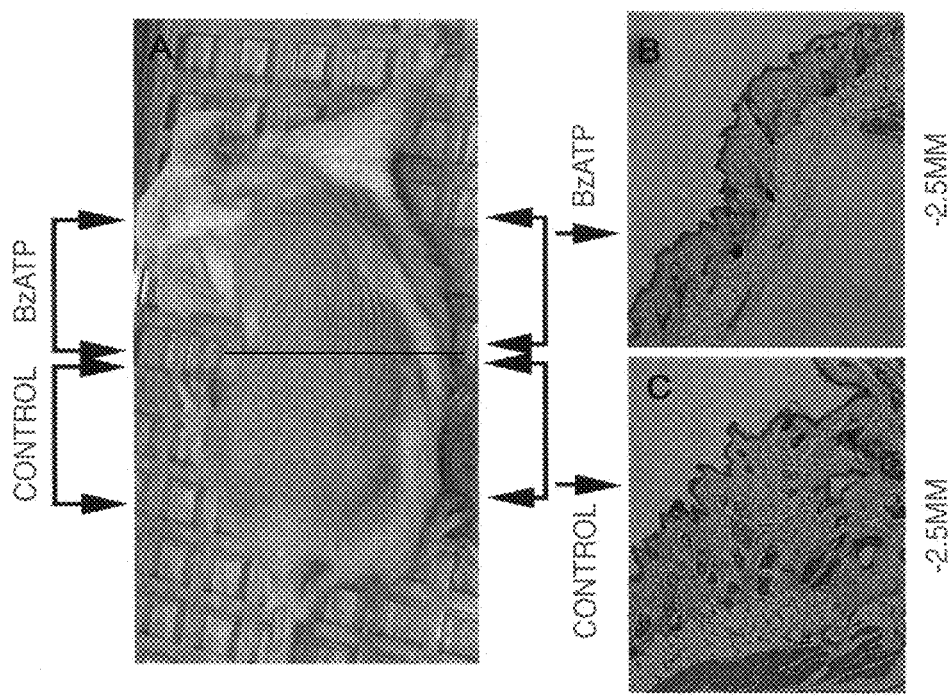
Figure 13:
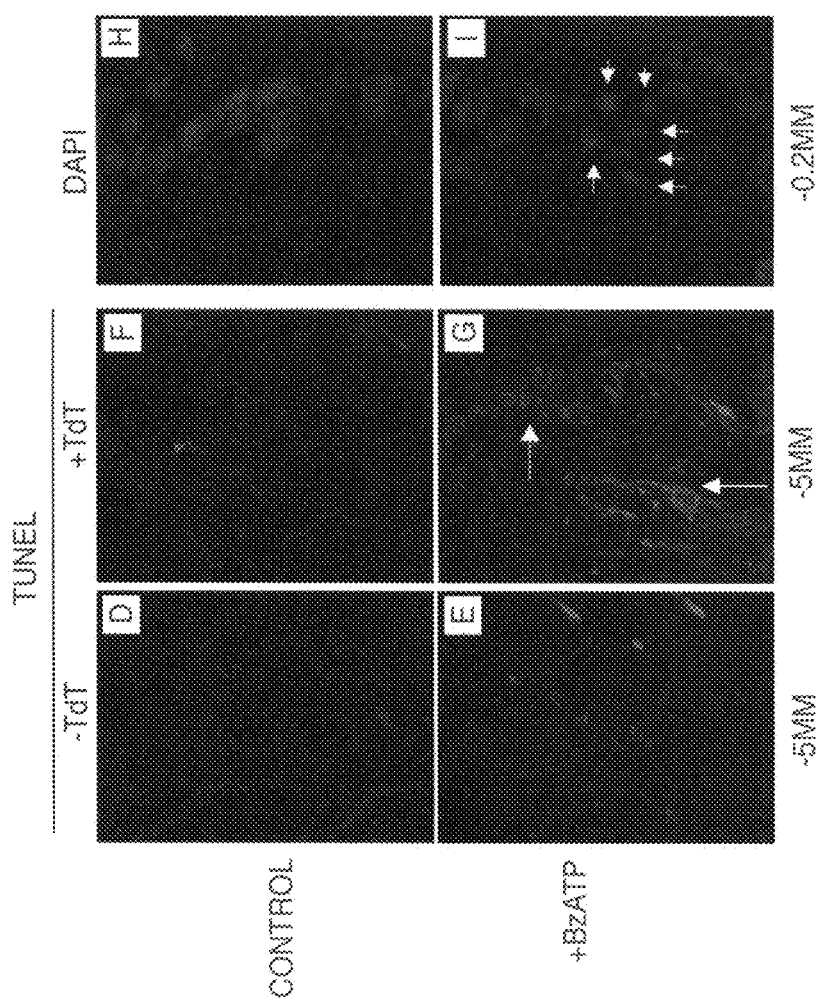

FIG. 13 presents exemplary data showing the effects in mice (n=5) in-vivo of local treatment with BzATP on skin apoptosis. Treatments are described herein as Experiment-5. BzATP (B) was applied on the shaved anterior skin area with the Control (C) applied in parallel on the shaved posterior skin area. The horizontal line shows schematically separation of the anterior and posterior dorsal skin regions. Data in A-I are representative of similar results in five animals.

FIG. 13A: Gross morphology of an untreated control mouse.

FIG. 13B: An H&E stained cross section of BzATP treated anterior skin.

FIG. 13C: An H&E stained cross section of control posterior skin.

FIG. 13D: A TUNEL stained cross section of control posterior skin in the absence of TdT.

FIG. 13E: A TUNEL stained cross section of BzATP treated anterior skin in the absence of TdT.

FIG. 13F: A TUNEL stained cross section of control posterior skin in the presence of TdT.

FIG. 13G: A TUNEL stained cross section of BzATP treated anterior skin in the presence of TdT. Arrows: Enhanced TUNEL staining in epidermal cells of the basal/parabasal layers (horizontal arrow) and of epidermal hair shaft cells (vertical arrow).

FIG. 13H: Nuclear staining with DAPI in control posterior skin.

FIG. 13I: Nuclear staining with DAPI in BzATP treated anterior skin. Arrows: Nuclei of epidermal cells in basal/parabasal regions of the epidermis at advanced stages of condensation, fragmentation and pyknosis.

Figure 14:
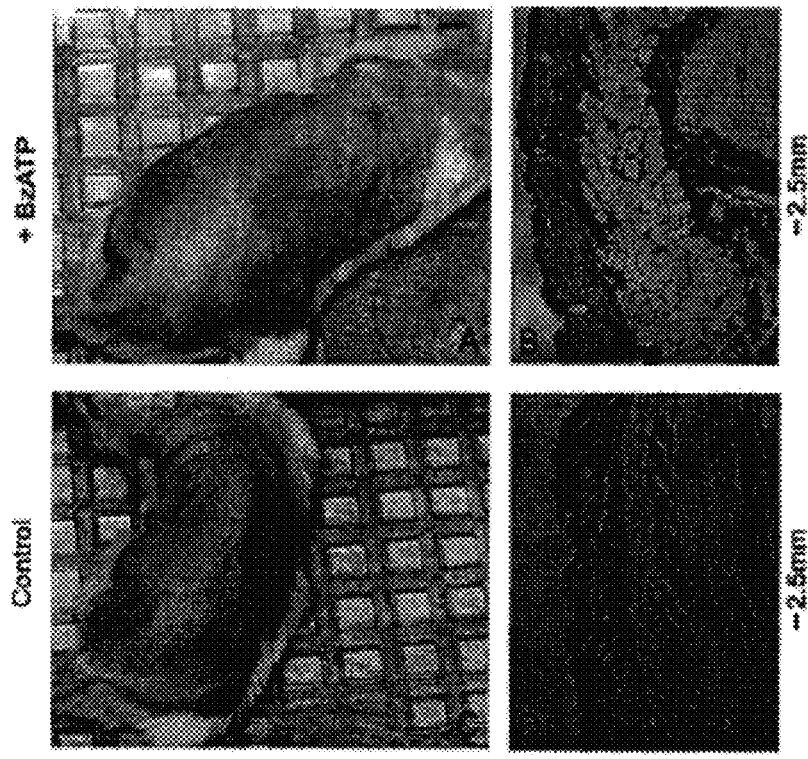
Figure 14:
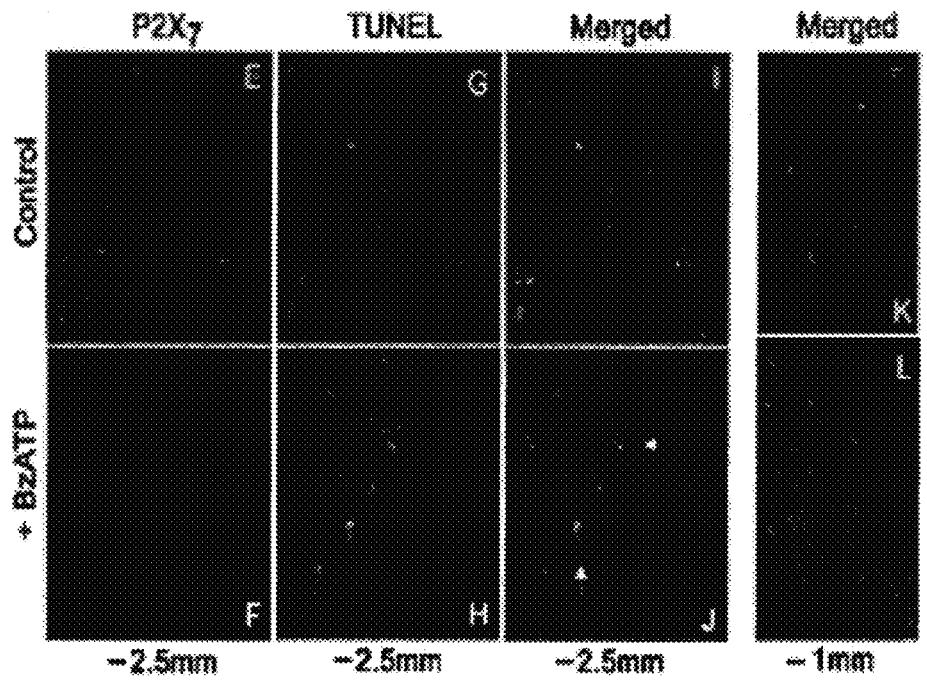
Figure 15:
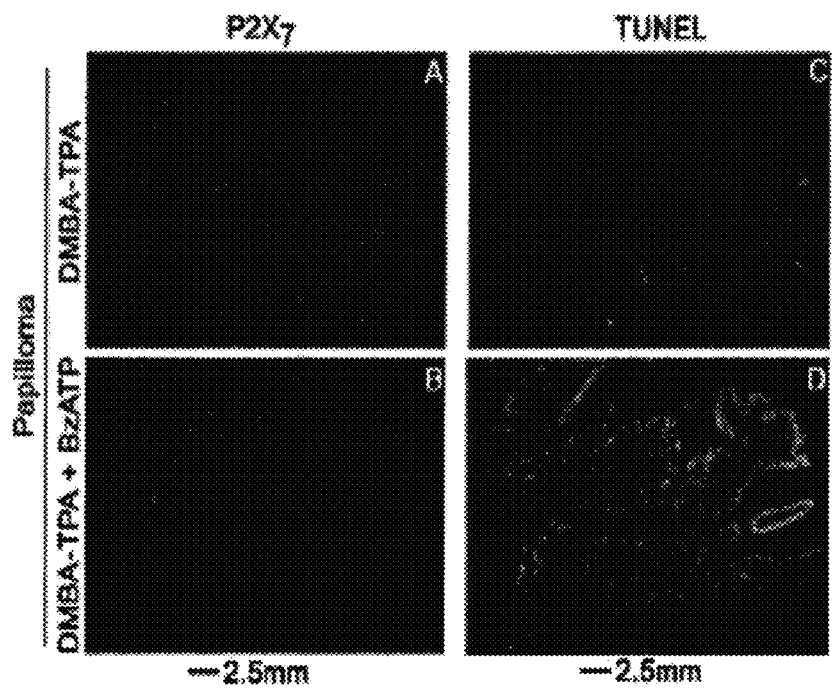
Figure 15:
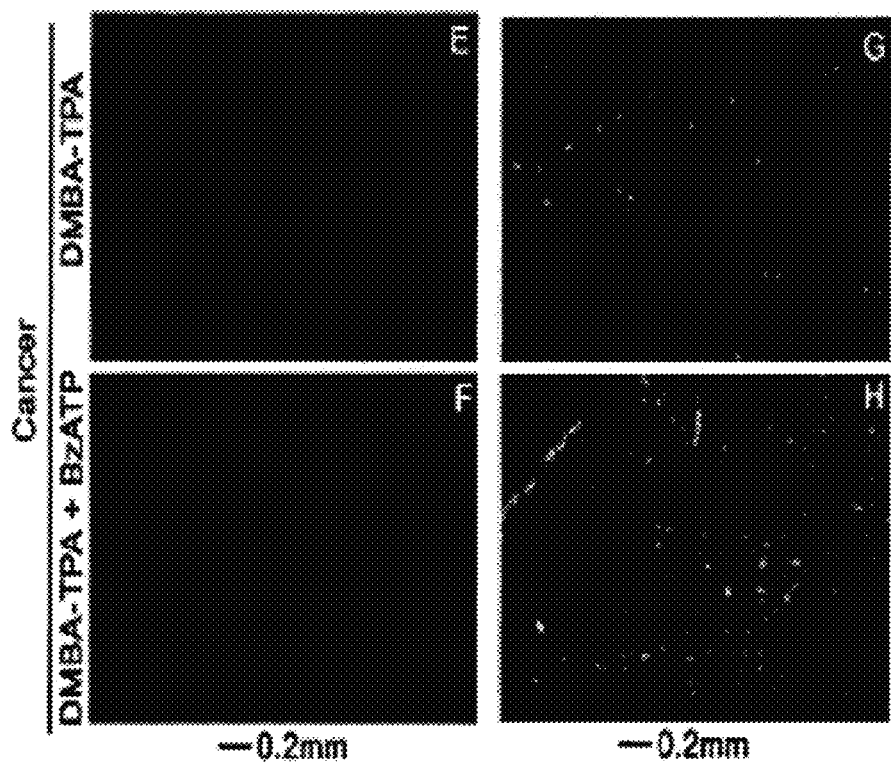

FIG. 14 presents exemplary data showing the effects in mice in-vivo of local treatment with BzATP on skin apoptosis. Treatments are described herein as Experiment-6. Animals (n=5) were treated for 16 weeks either with BzATP, applied locally twice a week. Assays were repeated 3-5 times with similar trends FIG. 14A: Gross morphology of dorsal skin treated with BzATP.

FIG. 14B: Cross section of dorsal skin treated with BzATP with H&E stain.

FIG. 14C: Gross morphology of dorsal skin treated with vehicle.

FIG. 14D: Cross section of dorsal skin treated with vehicle with H&E stain.

FIG. 14E: Cross section of dorsal skin treated with vehicle with $P2X_7$ immunostain.

FIG. 14F: Cross section of dorsal skin treated with BzATP with $P2X_7$ immunostain.

FIG. 14G: Cross section of dorsal skin treated with vehicle with TUNEL stain.

FIG. 14H: Cross section of dorsal skin treated with BzATP with TUNEL stain.

FIG. 14I: Overlay of FIG. 14E and FIG. 14G showing co-localization at low magnification.

FIG. 14J: Overlay of FIG. 14F and FIG. 14H showing co-localization at low magnification. Arrows: Increased TUNEL staining co-localizing with $P2X_7$ immunoreactivity in epidermal cells of the basal/parabasal layers (horizontal arrow) and of epidermal hair shaft cells (vertical arrow).

FIG. 14K: Overlay of FIG. 14E and FIG. 14G showing co-localization at high magnification.

FIG. 14L: Overlay of FIG. 14F and FIG. 14H showing co-localization at high magnification.

FIGS. 15A-15H present exemplary data showing the effects of treatments with BzATP on $P2X_7$ expression and apoptosis in DMBA/TPA-induced skin papillomas FIGS. (15A-15D) and cancers (FIGS. 15E-15H). Treatment is described herein as Experiment-4. Assays were repeated 4 times with similar trends. FIGS. 15C, 15D, 15G, & 15H are parallel cross sections to FIGS. 15A, 15B, 15E, & 15F, respectively.

Figure 16:
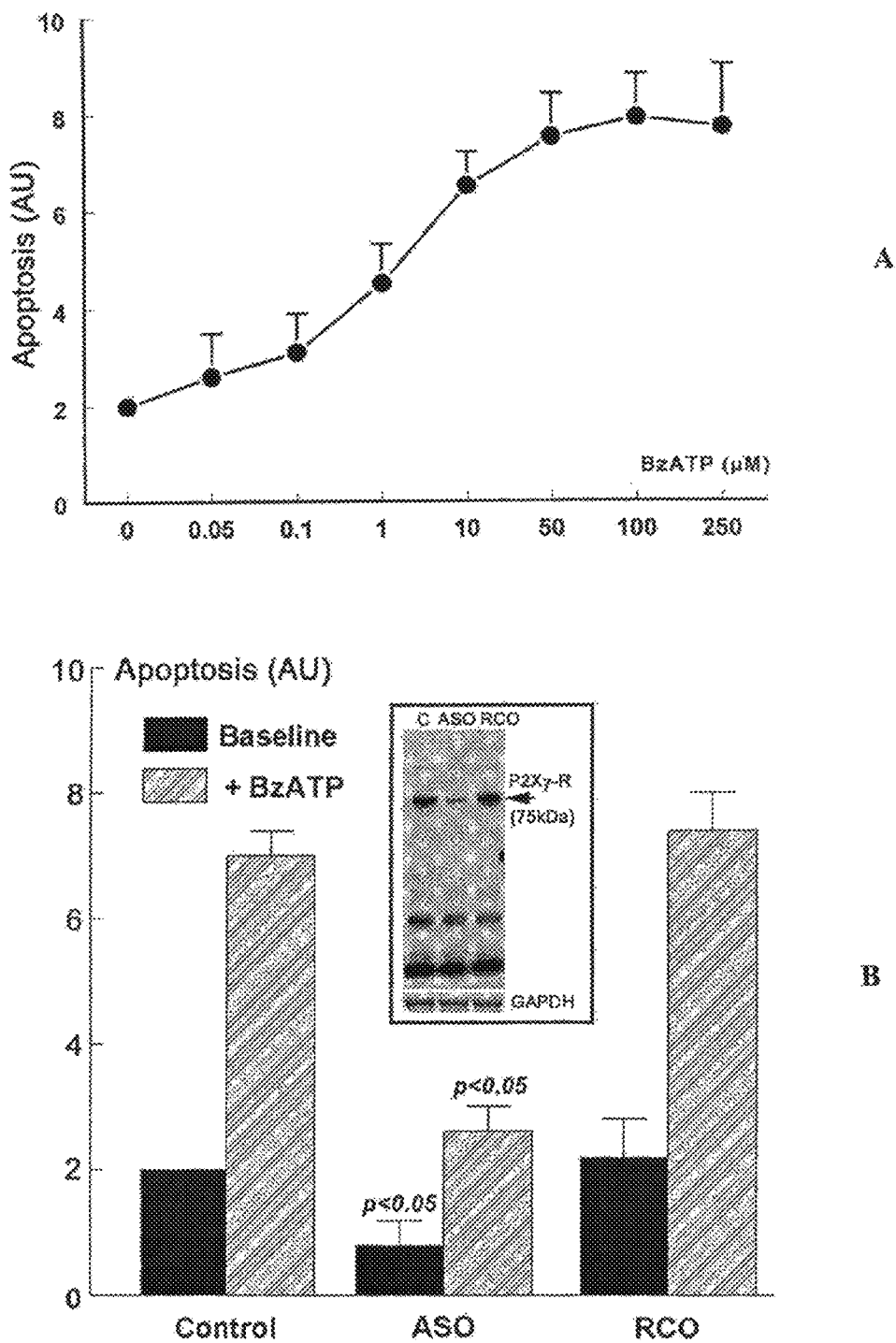
Figure 16:
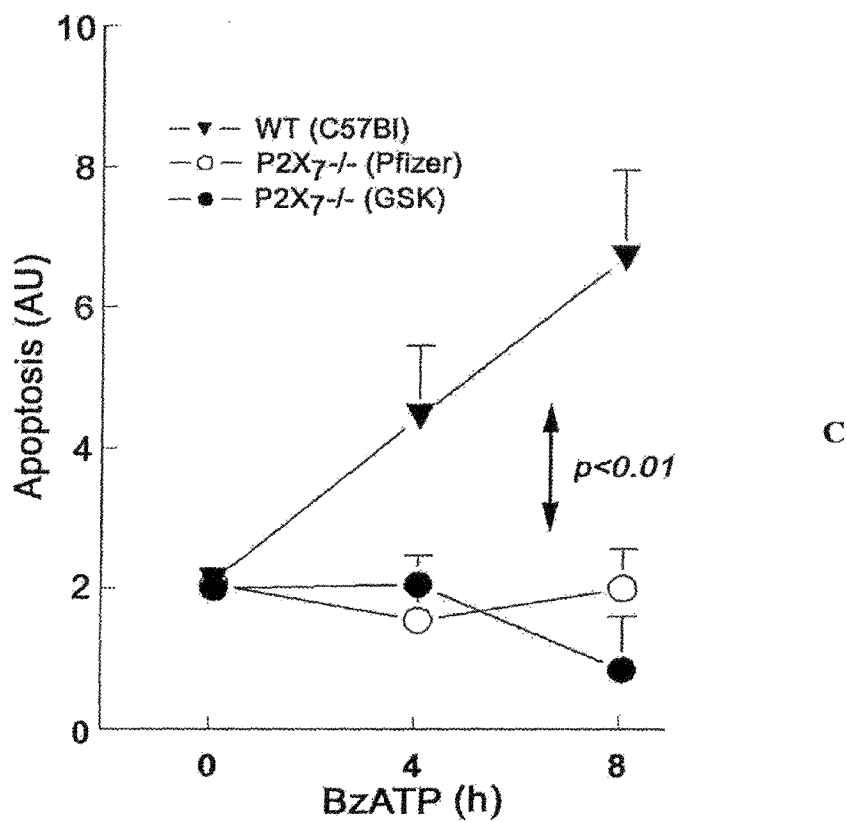

FIG. 16 presents exemplary data showing the effects of BzATP on apoptosis in cultured mouse keratinocytes. In all experiments, levels of apoptosis were normalized to an arbitrary value of 2 AU in control cells. AU=arbitrary units.

FIG. 16A: BzATP dose-response effect in cultured mouse normal (wild-type, C57B1) keratinocytes (means±SD, n=3). Cells were treated with one of the indicated concentrations of BzATP for 8 hours. Changes in apoptosis were determined in terms of solubilized DNA FIG. 16B: Cultured mouse normal keratinocytes (wild-type, C57B1) were pre-treated with 100 µM anti-sense $P2X_7$ oligonucleotides (ASO) or random-control $P2X_7$ oligonucleotides (RCO) for 14 hours followed by 8 hours treatment with 100 µM BzATP. Control=cells treated with the vehicle of the ASO. Values are means (±SD) of 3 experiments for each condition. Insert: Western immunoblot with anti-$P2X_7$ antibody of lysates of cells treated with ASO or RCO (n=2). Changes in apoptosis were determined in terms of solubilized DNA FIG. 16C: BzATP time-response effect in cultured mouse normal keratinocytes (wild-type, C57B1; filled triangles), or in keratinocytes obtained from C57B1 background $P2X_7$-deficient mice ($P2X_7^{-/-}$Pfizer; empty circles; or $P2X_7^{-/-}$ GSK; filled circles). Values are means (±SD) of 3 experiments for each condition. Changes in apoptosis were determined using cell-death detection ELISA.

Figure 17:
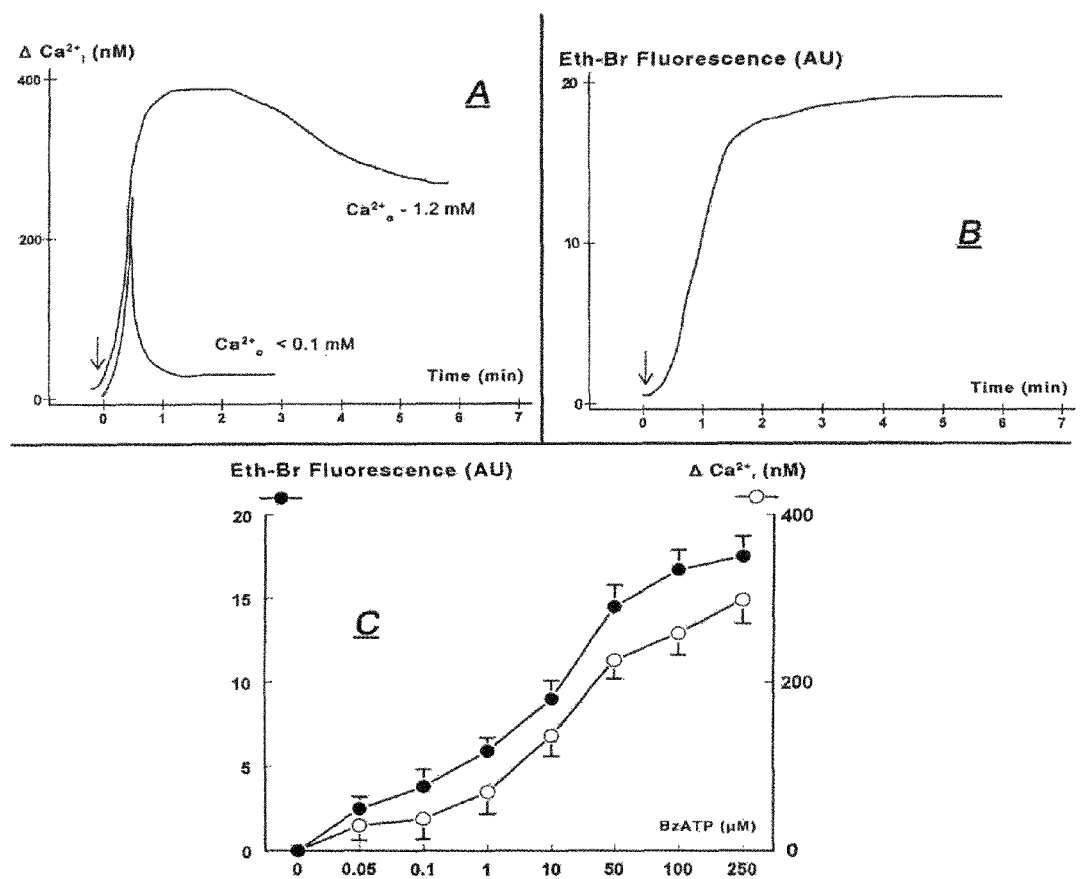

FIG. 17 presents exemplary data showing the effects of BzATP in mouse wild-type normal keratinocytes. BzATP was added (arrows) at 100 µM. $Ca^{2+}{}_o$=extracellular calcium.

FIG. 17A: Time course of changes in cytosolic calcium ($\Delta Ca^{2+}{}_i$), in medium containing 1.2 mM $Ca^{2+}$ (upper trace) or 1.2 mM Ca2+ plus 1.2 mM EGTA (lower trace).

FIG. 17B: Time course of influx of ethidium bromide (Eth-Br).

FIG. 17C: Dose response profile comparison between $\Delta Ca^{2+}{}_i$ and Eth-Br influx. Cells were treated with each BzATP concentration for 8 hours. Levels of $\Delta Ca^{2+}{}_i$ (empty circles) were determined 2 min after adding BzATP; changes in Eth-Br fluorescence (filled circles) were determined 5 min after adding BzATP. Values=means±SD. Experiments were repeated 3 times. AU=arbitrary units.

Figure 18:
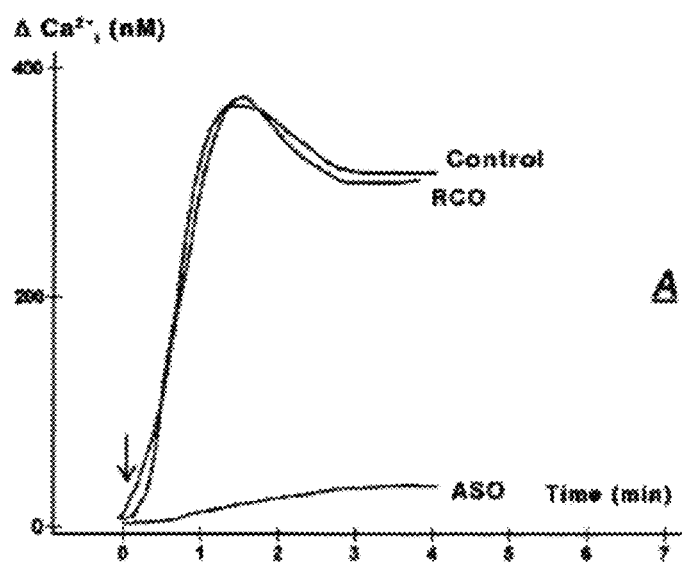
Figure 18:
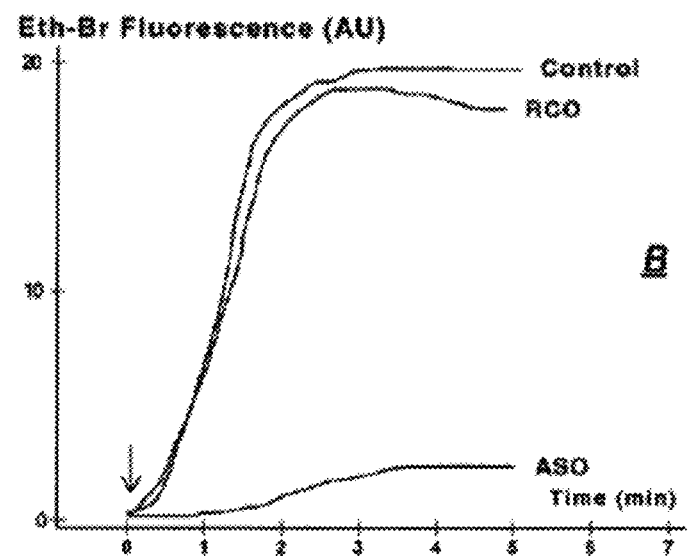

FIG. 18 presents exemplary data showing the effects of anti-sense $P2X_7$ oligonucleotides on BzATP treatment of cultured mouse wild-type normal keratinocytes pretreated with 100 µM anti-sense $P2X_7$ oligonucleotides (ASO) or random-control $P2X_7$ oligonucleotides (RCO) for 14 hours followed by 8 hours treatment with 100 µM BzATP. Control=cells treated with the vehicle of the ASO. The experiments were repeated twice with similar trends.

FIG. 18A: Changes in cytosolic calcium ($\Delta Ca^{2+}{}_i$).

FIG. 18B: Influx of ethidium bromide (Eth-Br).

Figure 19:
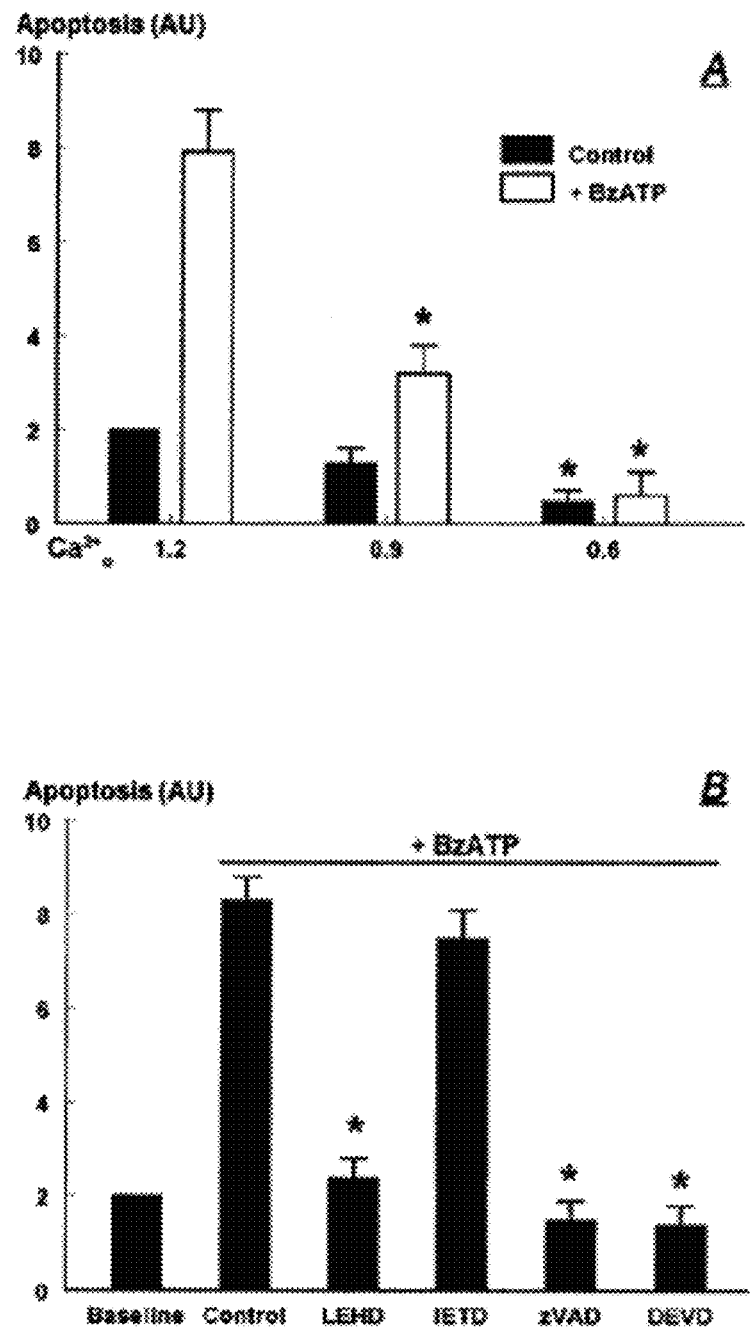

FIG. 19A presents exemplary data showing the dependence of BzATP-induced apoptosis on extracellular calcium ($Ca^{2+}{}_o$). Cultured mouse wild-type normal keratinocytes were shifted for 10 minutes to medium containing one of the indicated $Ca^{2+}{}_o$ concentrations. Control (physiological) level of $Ca^{2+}{}_o$ was 1.2 mM, and levels of $Ca^{2+}{}_o$ were modulated by adding 1.2 mM EGTA. Cells were treated with 100 µM BzATP, or the vehicle (Control), and changes in apoptosis were determined after 8 hours. Apoptosis were determined in terms of solubilized DNA. Values are means (±SD) of 3 experiments. Levels of apoptosis were normalized to an arbitrary value of 2 in non-treated cells. AU=arbitrary units. *=p< 0.01 as compared to $Ca^{2+}{}_o$ 1.2 mM.

FIG. 19B presents exemplary data showing modulation of BzATP-induced apoptosis (100 µM, 8 hours) in mouse wild-type normal keratinocytes by 50 µM caspase inhibitors incubated for 8 hours. Apoptosis were determined in terms of solubilized DNA. Values are means (±SD) of 3 experiments. Levels of apoptosis were normalized to an arbitrary value of 2 in non-treated cells. AU=arbitrary units. *=p<0.01 compared to control.

Figure 20:
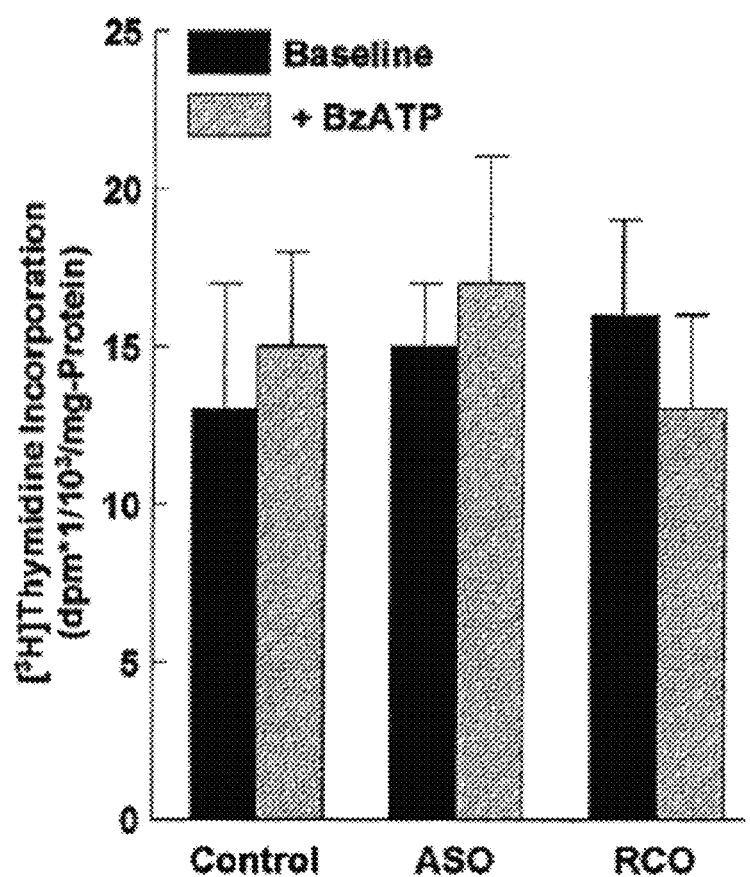

FIG. 20 presents exemplary data showing the effects of pre-treatment with anti-sense $P2X_7$ oligonucleotides (ASO) or random-control $P2X_7$ oligonucleotides (RCO) (both at 100 µM for 14 hours), and of treatments with BzATP (100 µM, 8 hours) on [$^3$H]-thymidine incorporation in mouse wild-type normal keratinocytes (values are means±SD, n=4).

Figure 21:
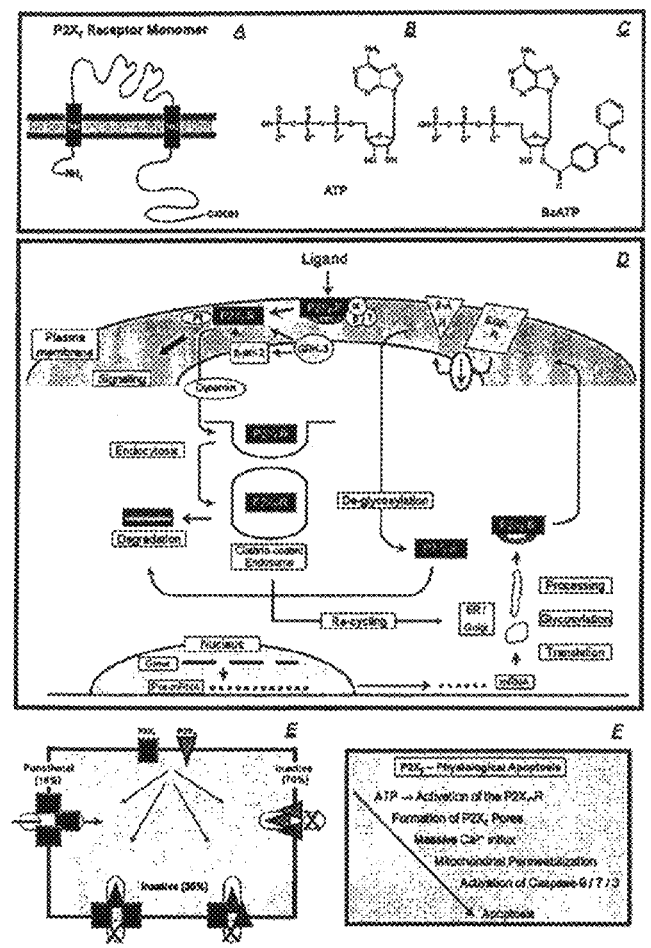

FIG. 21A shows one embodiment of a predicted structure of a $P2X_7$ receptor monomer, showing a short intracellular N-terminus; two transmembrane (TM) segments containing the extracellular domain; and the long intracellular C-terminus.

FIG. 21B and FIG. 21C show structural embodiments of $P2X_7$ receptor ligands ATP and BzATP.

FIG. 21D illustrated one embodiment of the expression, mechanism of action, and regulation of the $P2X_7$ receptor. The functional $P2X_7$ receptor is a glycosylated G-coupled membrane-bound protein and its natural ligand is ATP. Activation stimulates GRK-3-mediated phosphorylation of the receptor (pi-$P2X_7$-R), and recruitment of β-arrestin-2 (β-arr-2) to the plasma membrane. The activated receptor can induce stimulation of one or more signaling pathways. β-arrestin binding facilitates uncoupling of the receptor from the heterotrimeric G proteins (a,b,g), and targets the receptor in a dynamin-related mechanism to clathrin-coated pits for endocytosis. Endocytosis can be followed by receptor sequestration into various cellular domains, recycling, and degradation. Glycosylation of the $P2X_7$ receptor is controlled by β2-adrenoceptor (β-AR)-activation of PKA, resulting in de-glycosylation of the $P2X_7$ receptor and enhanced receptor degradation. The PKA effect is regulated by the action of the EGF-EGFR system; it involves facilitated, PI3K-dependent inhibition of β-AR internalization, and facilitated β-AR recycling, thereby increasing the pool of β-ARs in the plasma membrane that are available for activation upon ligand binding.

FIG. 21E illustrates one embodiment of ligand-induced pore formation involving homo(tri)-oligomerization of $P2X_7$ monomers. Cells express the full-length receptor (square), as well as truncated forms of the $P2X_7$, e.g. the $P2X_{7-j}$ variant (triangle) that can hetero-oligomerize with the full-length $P2X_7$ form and produce non-functional pores. Data in host cells co-expressing the $P2X_7$ plus the $P2X_{7-j}$ suggested the formation, shown in the figure, of four types of complexes (numbers in parentheses are the order of expression). F. Pathway of physiological $P2X_7$-mediated apoptosis in epithelial cells. Activation of the P2X$_7$ receptor (P2X$_7$R) by ATP induces pore formation and uncontrolled influx of Ca$^{2+}$, triggering permeabilization of the mitochondria and activation of caspase 9/7/3-mediated apoptosis.

Figure 22:
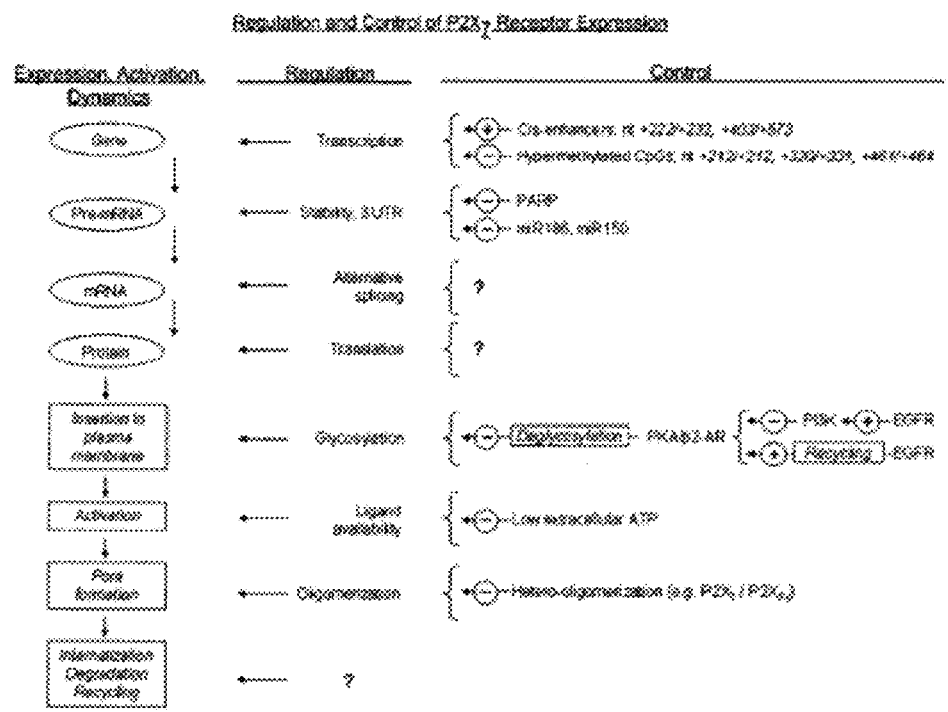

FIG. 22 presents a schema of possible mechanisms that regulate and control the expression, activation, and dynamics of the P2X$_7$ receptor.

Figure 23:
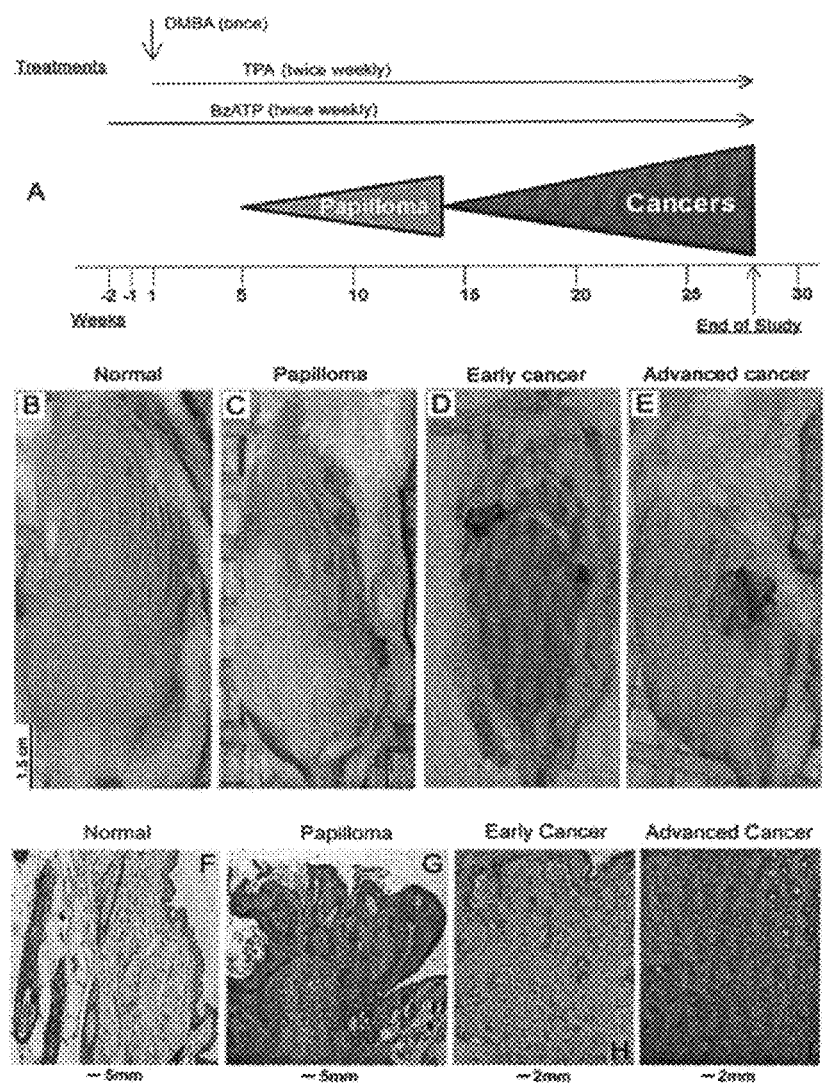

FIG. 23A: Design of the study, Fu et al., "Activation of P2X(7)-mediated apoptosis Inhibits DMBA/TPA-induced formation of skin papillomas and cancer in mice" BMC Cancer 9:114 (2009). Drugs were applied locally on the shaved dorsal skin of mice at the indicated times. Shown are the phases of papilloma and skin cancers formation in response to the treatments with DMBA and TPA.

FIGS. 23B-E: Representative pictures of DMBA/TPA-induced skin lesions in-vivo.

FIGS. 23F-I: Representative skin cross-sections, evaluated histologically by H&E, of normal and DMBA/TPA-induced lesions in-vivo.

Figure 24:
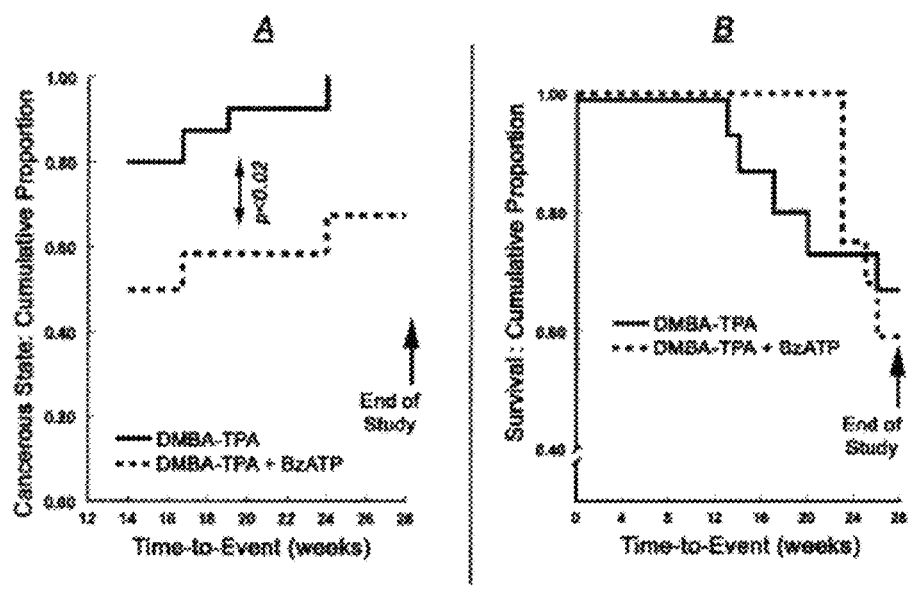

FIG. 24 present a summary of the effects of local treatments with DMBA/TPA (continuous lines) or DMBA/TPA+ BzATP (broken lines) on the time-to-event of cancer state (A) and on the animals' survival rates (B).

Figure 25:
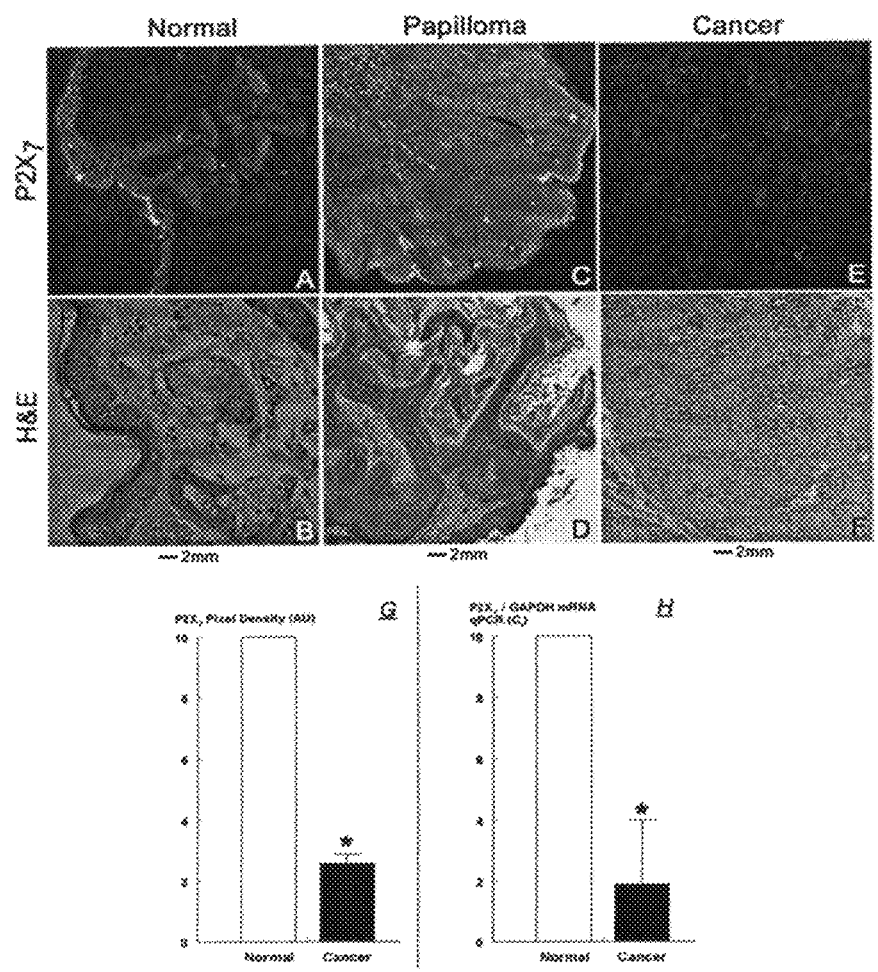

FIG. 25 presents illustrative data showing P2X$_7$ immunoreactivity in mouse normal skin (A), papilloma (C), and skin cancer tissues (E); B,D,F are parallel cross sections, respectively, stained by H&E. G. Analysis of P2X7 immunoreactivity compared among paired histologically normal and cancerous tissues. Bars are means (±SD, n=5). H. P2X7 mRNA levels (relative to GAPDH mRNA) (means±SD, n=3) in histologically normal and cancerous tissues. In G and H data were normalized to an arbitrary value of 10. *p<0.01. AU—arbitrary units.

Figure 26:
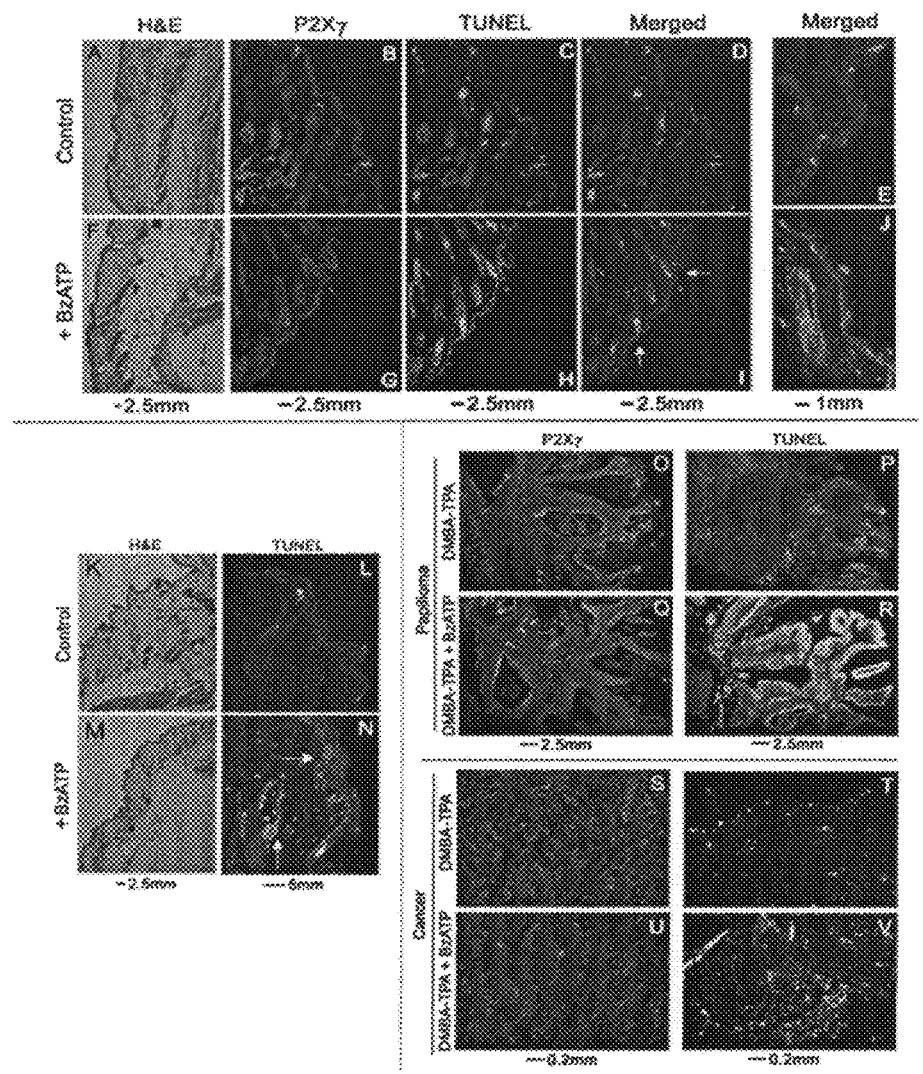

FIG. 26 presents illustrative data showing effects of local treatment with BzATP in-vivo on skin apoptosis. A-J: Mice were treated for 16 weeks either with BzATP, applied locally twice a week on the shaved dorsal skin (F-J), or with the vehicle (Control, A-E). At the end of the experiment animals were euthanized and strips were obtained from each animal dorsal skin areas for H&E (A,F); and for P2X7 immunostaining plus TUNEL (apoptosis) co-staining (B-E, G-J). Arrows in I show increased TUNEL staining co-localizing with P2X7 immunoreactivity in epidermal cells of the basal/parabasal layers (horizontal arrow) and of epidermal hair shaft cells (vertical arrow). E and J are higher magnification of D and I. K-N: Mice were treated with BzATP, applied locally twice a week for 4 weeks on the shaved anterior skin area, and with the vehicle (Control) applied in parallel on the shaved posterior skin area. At the end of the experiment animals were euthanized and skin cross sections were generated from each animal for H&E (K,M) and TUNEL (L,N) staining. Arrows in N show enhanced TUNEL staining in epidermal cells of the basal/parabasal layers (horizontal arrow), and of epidermal hair shaft cells (vertical arrow). O-V: Effects of treatments with BzATP on P2X7 expression and apoptosis in DMBA/TPA-induced skin papillomas (O-R) and cancers (S-V). P,R,T,V are parallel cross sections to O,Q,S,U, respectively.

Figure 27:

FIG. 27 demonstrates one embodiment of a proposed schema of a CpG-rich 547 nt DNA region (+26/+573) downstream of an active promoter of a P2X$_7$ gene. Filled ellipses denote CpG sites that were found experimentally to inhibit P2X$_7$ transcription. Upwards pointing arrows denote CpG sites that were found experimentally to be hypermethylated in cultured cervical cells and in cervix epithelial tissues in vivo. Hatched squares are cis regions that were found experimentally to possess transcription enhancer activity. Horizontal bi-directional arrows show four putative sites within the cis-enhancer regions that were found to form DNA-protein complexes.

Figure 28:
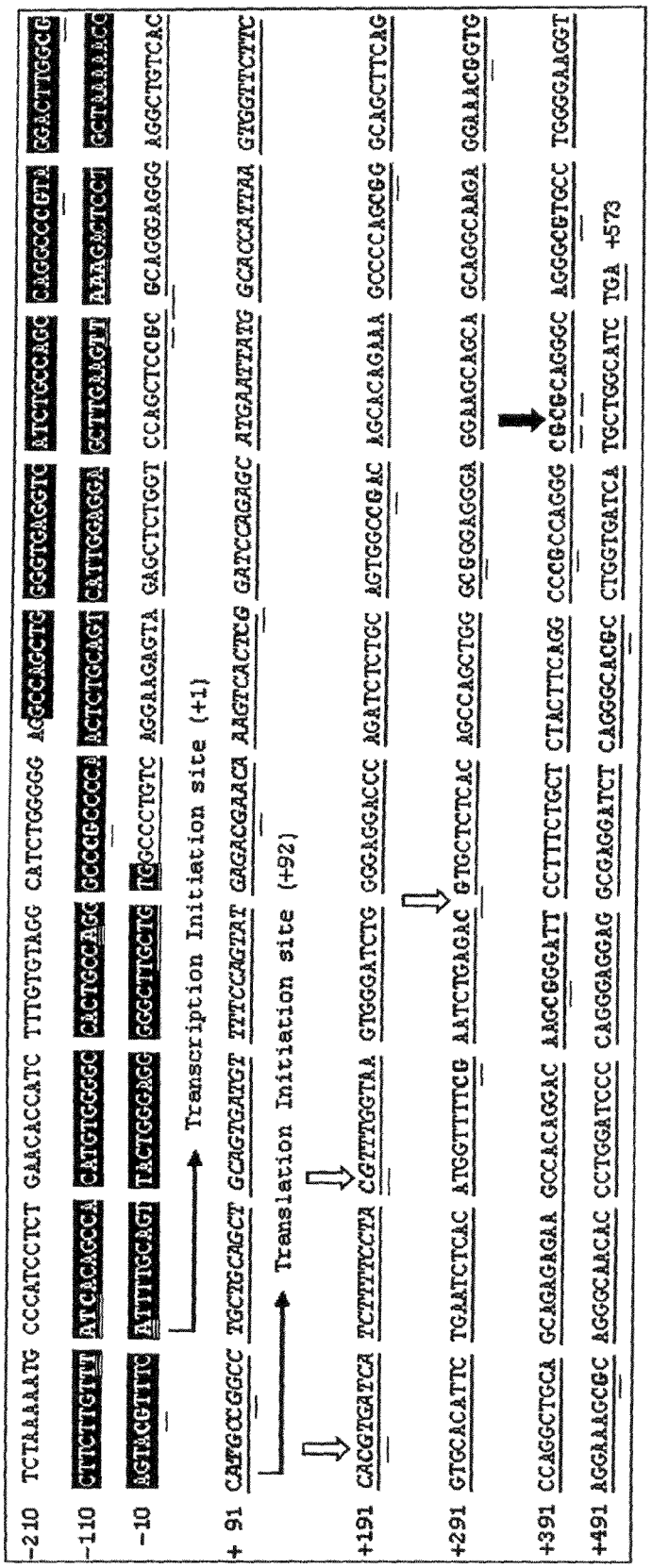

FIG. 28 presents one embodiment of a nucleotide sequence of a 5' region of human P2X$_7$ (SEQ TD NO: 62), containing an active promoter (white symbols on black background, nt −158/+32); a 547 nt CpG-rich region (underlined, nt -+26/+ 573) downstream of the promoter; Exon 1 (underlined and italics, nt +92/+216); and the proximal part of intron-1 (distal to Exon 1, underlined, beginning at nt +217). Nucleotides were numbered relative to the Transcription Initiation Start Site (TpIS) (+1; nt 1683 according to GenBank Y12851). TpISs and TATA-like sequences within the active promoter bases/regions are bolded and doubly underlined. CpG dinucleotides are bolded and doubly underlined. Vertical thick empty arrows point to MaeII-sensitive CpG sites (nt +193/+194, +211/+212, and +330/+331). The vertical thick filled arrow points to a BstUI-sensitive CpG-CpG site (nt +461/+462 and +463/+464). For DNA methylation experiments the 547 nt CpG-rich region was subdivided into Segment-1 (nt +26/+247), Segment-2 (nt +223/+399), and Segment-3 (nt +352/+573).

Figure 29:
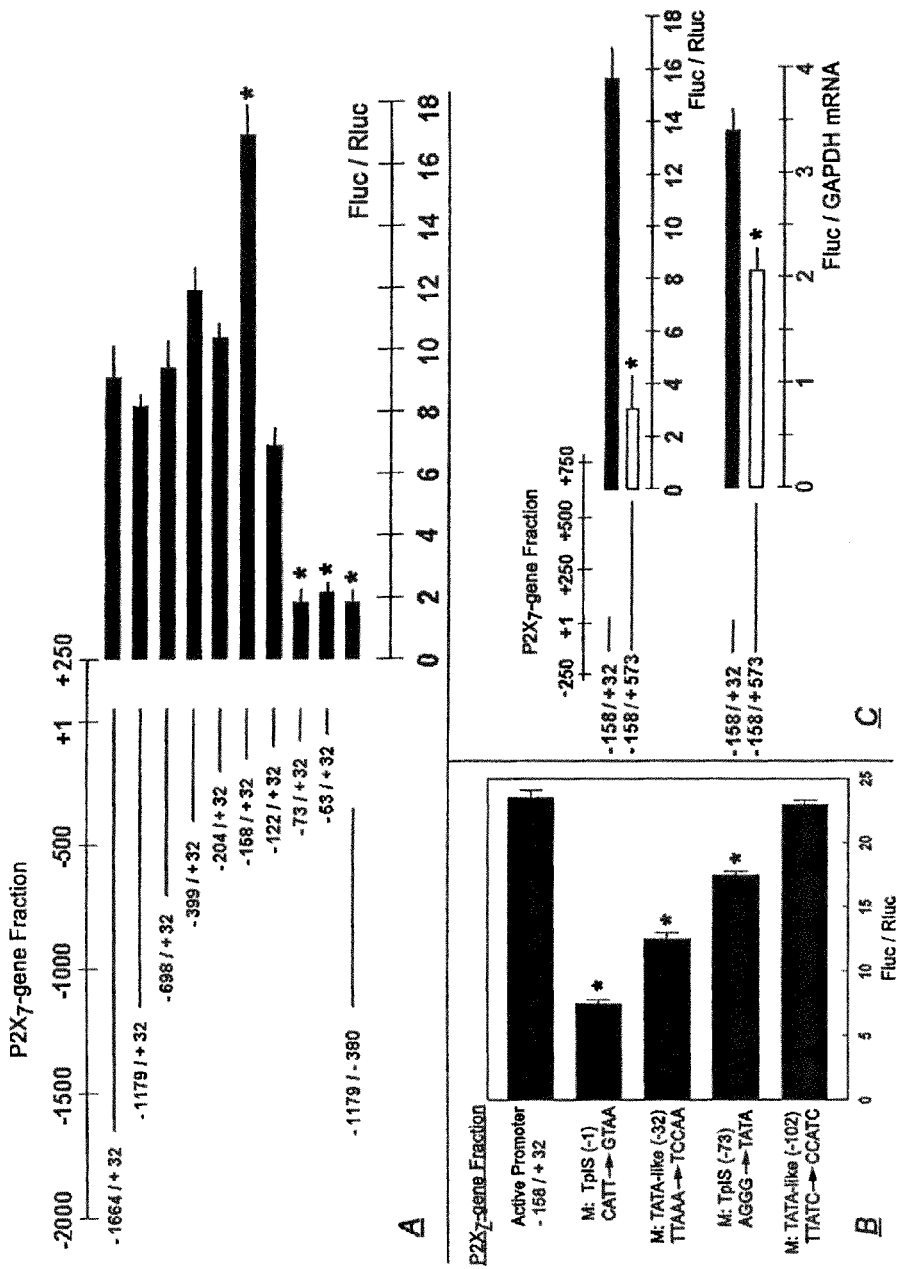

FIG. 29 presents one embodiment of an elucidation of a P2X$_7$ active promoter region.

FIG. 29A: cDNA fragments corresponding to regions within a 1.7 kb DNA segment of the 5' region of the human P2X$_7$ gene were inserted into luciferase vector; the P2X$_7$-luciferase reporters were transfected into HEK293 and P2X$_7$ promoter activity was determined in terms of changes in luciferase activity (Fluc/Rluc). Data (means±SD, 3-5 experiments in triplicates) were normalized (=1) to Fluc/Rluc recorded in cells transfected with empty vector. *-p<0.01 compared to the rest.

FIG. 29B: Confirmation of P2X$_7$ TpIS. Two potential TpISs and their related TATA-like regions were mutated and effects on P2X$_7$ transcription were determined as in FIG. 29A (means±SD, 3-5 experiments in triplicates). *-p<0.01 as compared to −158/+32.

FIG. 29C: P2X$_7$ transcription is modulated by effectors downstream of the active promoter. P2X$_7$ −158/+32 or −158/+573 luciferase reporters were transfected into HEK293 cells and P2X$_7$ promoter activity was determined in terms of changes in luciferase activity (Fluc/Rluc, upper panel) or in terms of changes in Fluc/GAPDH mRNA (lower panel). Shown are means (±SD) of 1-3 experiments in triplicates. Data of Fluc/GAPDH mRNA were normalized (=0) to those recorded in cells transfected with empty vector. *-p< 0.01.

Figure 30:
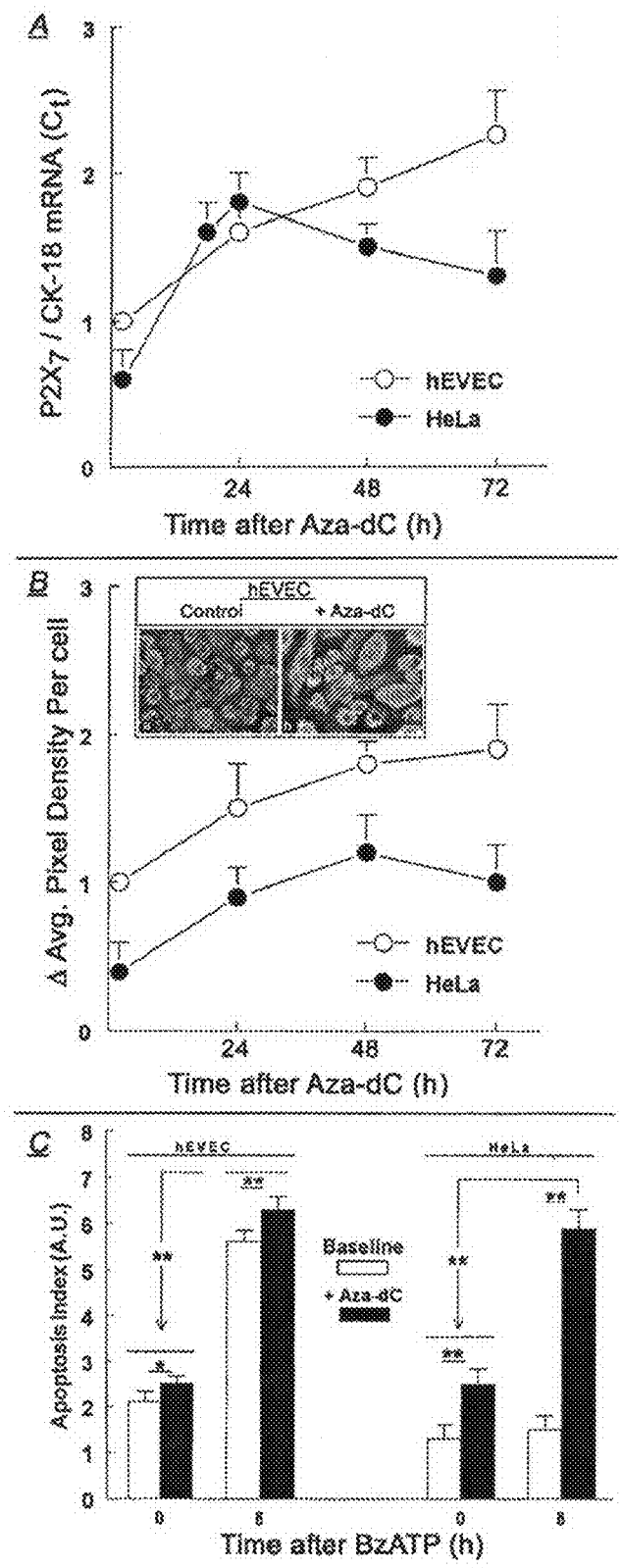

FIG. 30 presents exemplary data showing effects of treatments with Aza-dC (1 μM) on P2X$_7$ mRNA expression in hEVEC and HeLa cells. Data in A and B were normalized (=1) to levels in hEVEC cells at t=0. Means±SD of 3-6 experiments in triplicates.

FIG. 30A: Steady-state levels of P2X$_7$ mRNA. (p<0.01)

FIG. 30B: P2X$_7$ receptor protein levels. Insert: Immunofluorescence data @ 20×. (p<0.01)

FIG. 30C: BzATP-induced apoptosis (in arbitrary units [A.U.]) following Aza-dC. The degree of apoptosis (in arbitrary units [A.U.]) was normalized to levels determined in non-treated cells. *-p<0.05; **-p<0.01.

Figure 31:
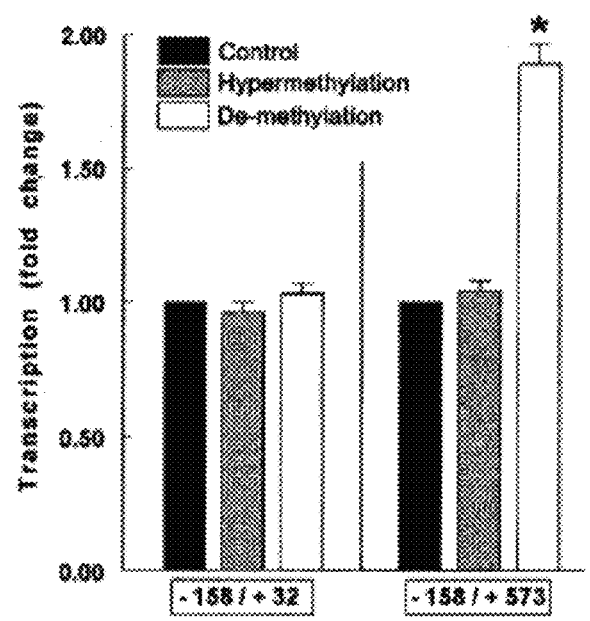

FIG. 31 presents exemplary data showing effects of hypermethylation and de-methylation on changes in transcription in HEK293 cells transfected with the luciferase −158/+32 or −158/+573 reporter constructs (means±SD of two experiments in triplicates).

Hypermethylation assays were done by incubating the test plasmids prior to transfections with the CpG-Methylase M.SssI and changes in transcription were determined in terms of changes in luciferase activity (Fluc/Rluc). De-methylation assays were done by treating transfected cells with Aza-dC (1 µM for 48 hours). Changes in transcription were determined in terms of changes in Fluc/GAPDH mRNA levels. Data were normalized (=1) to levels in control cells. *-p<0.01.

Figure 32:
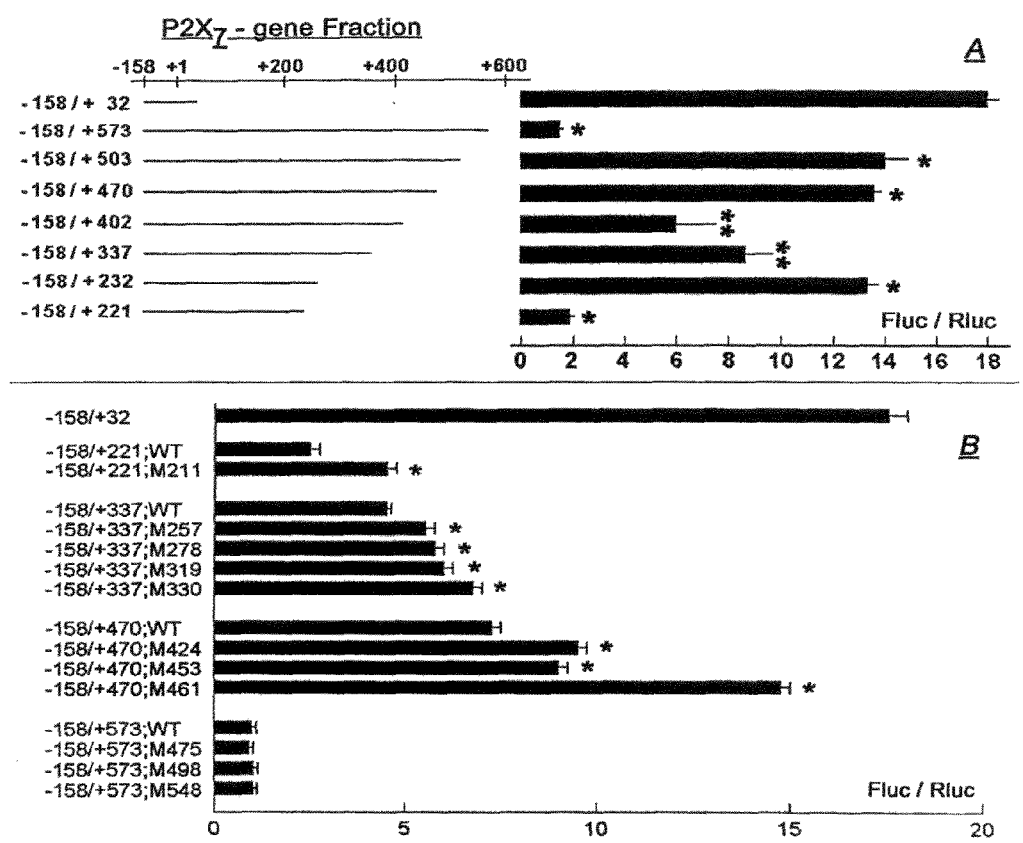

FIG. 32 presents several embodiments of constructs utilized to elucidate transcription regulatory cis-elements within a CpG-rich 547 nt region downstream of the P2X$_7$ promoter. Constructs comprise a P2X$_7$ active promoter attached with one of the shown segments and were inserted into a luciferase vector and transfected into HEK293 cells. Promoter activity was determined in terms of changes in luciferase activity (Fluc/Rluc, means±SD, of two experiments in triplicates).

FIG. 32A: cDNA fragments were constructed containing the P2X$_7$ active promoter (nt −158/+32) attached with one of the shown segments of the 547 nt region downstream of the promoter. *-p<0.01 compared to −158/+32; **-p<0.05-0.01 compared to −158/+232.

FIG. 32B: Effects of mutations in the CpG sites within the 547 nt region downstream of the promoter on P2X$_7$ transcription. WT—wild-type. *-p<0.01 compared to the wild-type sequence in each case.

Figure 33:
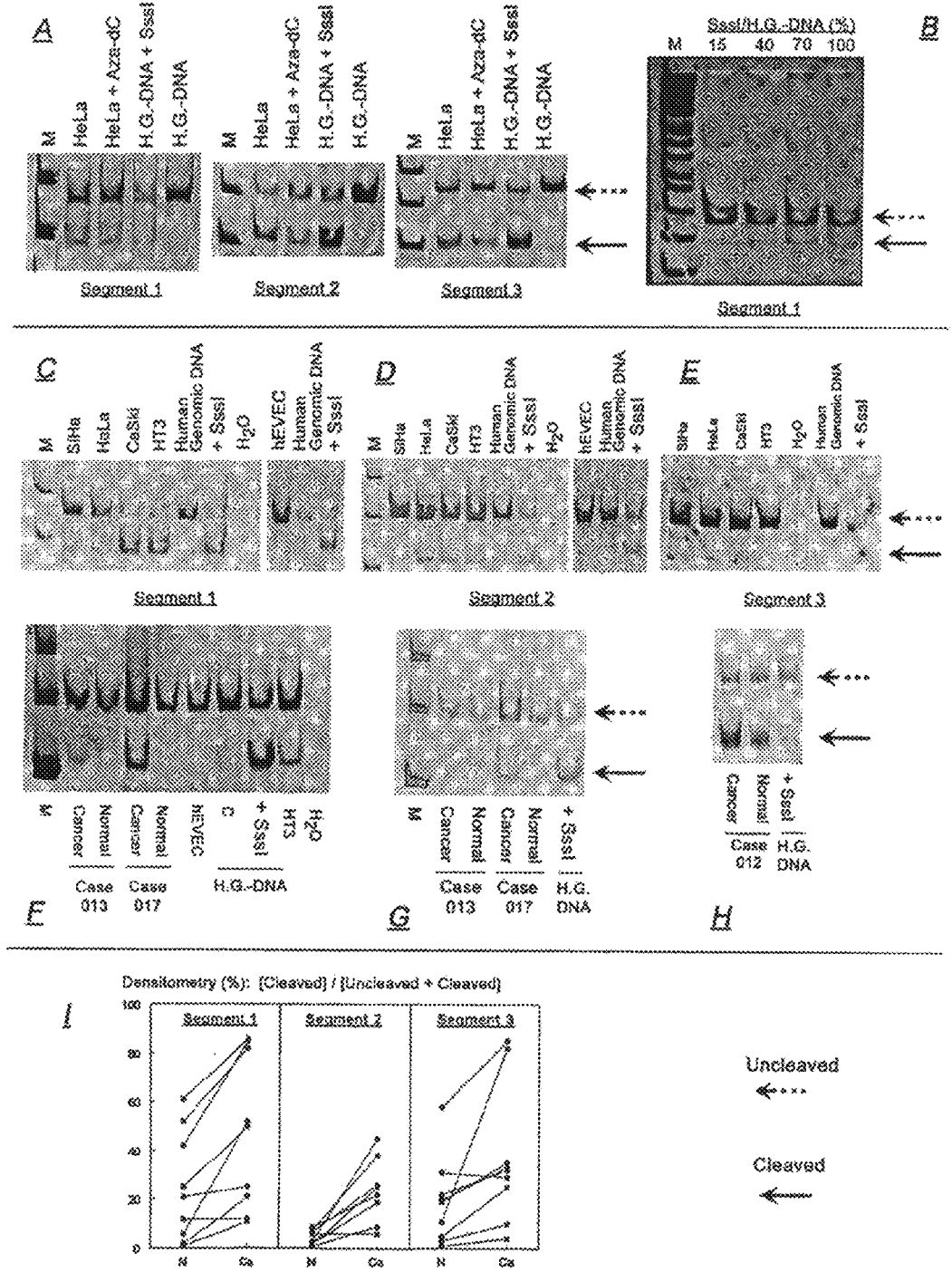

FIG. 33A presents exemplary data showing effects of treatment with Aza-dC in HeLa cells (1 µM, 48 hours) on methylation of cytosines in CpG sites +193/+194 (and/or +211/+212), +330/+331, and +461/+462 (and/or +463+464), within Segments 1, 2, and 3 respectively of a 547 nt region downstream of the P2X7 active promoter. Methylation of cytosines in CpG sites was determined in terms of cleavage at CpG sites using the genomic DNA bisulfite conversion method followed by gene specific PCR and restriction enzyme cutting. Left-pointing arrows show bands corresponding to uncleaved (broken lines) and cleaved fractions (continuous lines) at the CpG sites. M—markers. Controls were aliquots of human placental genomic DNA (H.G.—DNA) treated in vitro with the CpG methylase SssI.

FIG. 33B presents exemplary data from aliquots of human placental genomic DNA were mixed with different molar concentrations of SssI and the degree of cleavage at CpG sites +193/+194 (and/or +211/+212) within Segment-1. Data were normalized to the effect (100%) obtained in a reaction mixture containing 1 µg DNA.

FIGS. 33C-E present exemplary data showing methylation status of cytosines in CpG sites in cultured human epithelial uterine cervical cells.

FIGS. 33F-H present exemplary data showing methylation status of cytosines in CpG sites in human uterine cervix tissues in-vivo.

FIG. 33I presents exemplary data showing degree of restriction enzyme cleavage at CpG sites in tissues of human cervix. Data were compiled from 10 sets of paired cervical specimens, including in each case normal and squamous cell carcinoma tissues. Available for analysis were 9 cases for Segments 1 and 3, and 8 cases for Segment 2. Lines connect paired tissues (Normal [N] and Cancer [Ca]) from the same patient.

Figure 34:
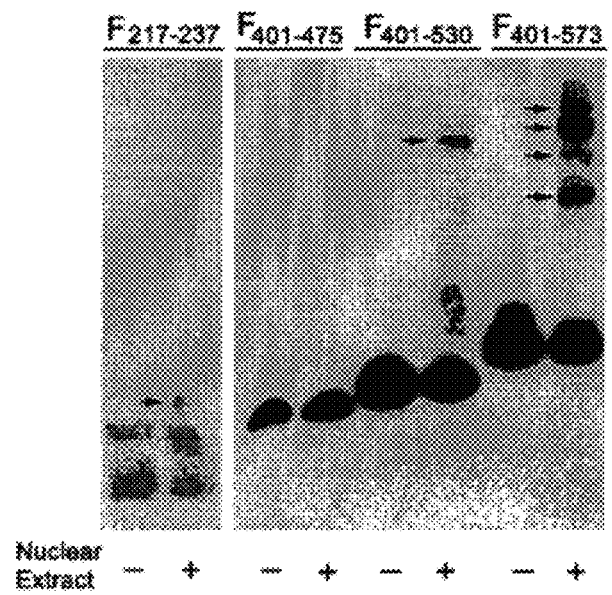

FIG. 34 presents exemplary data showing an elucidation of representative DNA-protein binding within the 547 nt region downstream of the P2X$_7$ promoter. The indicated cDNA fragments are depicted herein. See, Table 4. Electrophoretic mobility shift assays (EMSA) were used to detect DNA-protein complexes. Right-pointing arrows indicate shifted bands. The experiment was repeated twice.

DETAILED DESCRIPTION OF THE INVENTION

The present invention is related to the field of treatment and prevention of cancer. Cancer is believed to be a disease of overproliferation, wherein the present invention provides a method to reduce this overproliferation. For example, the methods herein result in the induction of intracellular apoptosis, thereby resulting in the prevention of cancerous growth and/or a reduction in cancer tumor size and number. The administration of a specific membrane receptor agonist (i.e., for example, a P2X$_7$ receptor agonist) is shown herein to reduce cancer growth and progression.

Anti-apoptotic mechanisms may contribute to the development of cancer. The P2X$_7$ system is believed to be a pro-apoptosis modulator in epithelial cells, and augmentation of P2X$_7$-mediated apoptosis has been proposed as a pharmacological modality for chemoprevention and treatment of epithelial cancers.

The growing understanding of mechanisms of P2X$_7$-mediated apoptosis has generated a strategy for targeting directly and specifically skin neoplasia. Although it is not necessary to understand the mechanism of an invention, it is believed that the data presented herein link directly, for the first time, an up-regulation of apoptosis with cancer prevention and treatment. For example, significant antitumor efficacy has been achieved in a rodent cancer model, and it is likely that compounds affecting P2X$_7$-control of apoptosis are useful for preventing and treating cancer (i.e., for example, epithelial cancer).

The data discussed herein demonstrates that a pharmacological activation of P2X$_7$-mediated apoptosis (i.e., for example, by a P2X$_7$-receptor agonist such as BzATP) inhibits chemically-induced (i.e., for example, by DMBA/TPA) formation of epithelial papillomas and/or squamous spindle-cell carcinomas. P2X$_7$ agonists, such as BzATP, are believed to increase intracellular apoptosis.

In one embodiment, the present invention contemplates a composition comprising at least one compound capable of activating P2X$_7$-induced apoptosis. In one embodiment, the compound comprises BzATP. Although it is not necessary to understand the mechanism of an invention, it is believed that, in vivo, P2X$_7$-induced apoptosis may control the development and progression of neoplasias. In one embodiment, the neoplasias comprise epithelial neoplasias. In one embodiment, the epithelial neoplasia is derived from an ectoderm layer. In one embodiment, the ectoderm layer neoplasia is selected from the group consisting of a skin neoplasia and a breast neoplasia. In one embodiment, the epithelial neoplasia is derived from a uro-genital sinus. In one embodiment, the uro-genital sinus neoplasia comprises a bladder neoplasia. In one embodiment, the epithelial neoplasia is derived from a distal paramesonephric duct. In one embodiment, the distal paramesonephric duct neoplasia is selected from the group consisting of a uterine cervix neoplasia and an endometrium neoplasia. Li et al., "The P2X$_7$ Receptor: A novel biomarker of uterine epithelial cancers" *Cancer Epidemiol Biomarkers Preven* 2006, 15:1-8; Li et al., "Decreased expression of P2X7 in endometrial epithelial pre-cancerous and cancer cells" *Gynecol Oncology* 2007, 106:233-243; Zhou et al., "Micro-RNAs miR-186 and miR-150 downregulate expression of the pro-apoptotic purinergic P2X$_7$ receptor by activation of instability sites at the 3'-untranslated region of the gene that decrease steady-state levels of the transcript" *J Biol Chem* 2008, 283:28274-28286; and Li et al., "P2X$_7$ receptor expression is decreased in epithelial cancer cells of ectodermal, uro-genital sinus, and distal paramesonephricduct origin" (Submitted, 2009).

I. Cancer

Cancer is believed to be an uncontrolled growth of abnormal cells in the body. Cancerous cells are also called malignant cells and are derived from normal cells in the body.

Cancer appears to occur when the growth of cells in the body is out of control and cells divide too quickly. It can also occur when cells "forget" how to die (i.e., for example, reduced apoptosis). There are many different kinds of cancers. Cancer can develop in almost any organ or tissue, including, but not limited to, the lung, colon, breast, skin, bones, or nerve tissue.

There are many causes of cancers, including, but not limited to, benzene and other chemicals, poisonous mushrooms and a type of poison that can grow on peanut plants (i.e., for example, aflatoxins), viruses, radiation, sunlight, or tobacco. However, the cause of many cancers remains unknown. The most common cancers in men in the United States include, but are not limited to skin cancer, prostate cancer, lung cancer, and colon cancer. In women in the U.S., the most common cancers include, but are not limited to, breast cancer, skin cancer, lung cancer, and colon cancer.

Some other types of cancers include, but are not limited to, brain cancer, cervical cancer, Hodgkin's lymphoma, kidney cancer, leukemia, liver cancer, Non-Hodgkin's lymphoma, ovarian cancer, skin cancer, testicular cancer, thyroid cancer, or uterine cancer. Symptoms of cancer depend on the type and location of the tumor. For example, lung cancer can cause coughing, shortness of breath, or chest pain. Colon cancer often causes diarrhea, constipation, and blood in the stool. Some cancers may not have any symptoms at all. In certain cancers, such as gallbladder cancer, symptoms often do not start until the disease has reached an advanced stage. The following symptoms can occur with most cancers: chills, fatigue, fever, loss of appetite, malaise, night sweats, or weight loss.

Common tests to identify cancer may include, but are not limited to, biopsy, blood chemistries x-ray, complete blood count, computerized tomography scan, or magnetic resonance imaging scan.

Conventional treatment varies based on the type of cancer and its stage. The stage of a cancer refers to how much it has grown and whether the tumor has spread from its original location. If the cancer is confined to one location and has not spread, current treatments are oriented towards surgery, radiation and/or chemotherapy. This is often the case with skin cancers, as well as cancers of the lung, breast, and colon.

A. Epithelial Cancers

Epithelial cancers are common and usually display aggressive and fatal biological-clinical behavior. Epithelia are tissues that line body surfaces. Although it is not necessary to understand the mechanism of an invention, it is believed that the present invention will lead to better understanding of how epithelial cancers develop. In one embodiment, the present invention contemplates a method for detecting cancers at early stage of development, consequently resulting in earlier treatment and improved survival rates. In one embodiment, the present invention contemplates methods of treating epithelial cancers. In one embodiment, the present invention contemplates methods of preventing epithelial cancers (i.e., for example, prophylactic treatments).

Epithelial cancers are thought to be common and can display aggressive and potentially fatal biological clinical behavior. Although it is not necessary to understand the mechanism of an invention, it is believed that some embodiments of the present invention could lead to: i) improved understanding of epithelial cancer development; ii) improved early cancer detection; iii) improved early cancer treatment; iv) new modalities and directions for cancer treatments; and v) improved epithelial cancer prevention.

Cancer development is believed associated with inactivation of tumor-controlling genes, including tumor suppressor and apoptosis-related genes. Inactivation of genes can be the result of allelic loss or loss-of-heterozygosity chromosomal sites due to gene mutations, deletions, and genomic rearrangements. Some cancers exhibit a number of genomic alterations including monoallelic hemizygous deletions at 4p15.3, 10q24, 5q35, 3p12.3, and 11q24. Wistuba et al., "Deletions of chromosome 3p are frequent and early events in the pathogenesis of uterine cervical carcinoma" *Cancer Res.* 57:3154-3158 (1997); Chu et al., "Monoclonality and surface lesion specific microsatellite alterations in premalignant and malignant neoplasia of uterine cervix: a local field effect of genomic instability and clonal evolution" *Genes Chromosomes Cancer* 24:127-134 (1999); and Hamoudi et al., "Identification of novel prognostic markers in cervical intraepithelial neoplasia using lDMAS (loh data management and analysis software)" *BMC Bioinformatics* 6:18 (2005). Alternatively, other studies demonstrate a possible loss of tumor suppressor gene on chromosome 11q23. Lai et al., "Hypermethylation of two consecutive tumor suppressor genes, BLU and RASSF1A, located at 3p21.3 in cervical neoplasias" *Gynecol Oncol.* 104:629-635 (2007).

II. Apoptosis

The current theory of epithelial cell growth predicts regulation by the concerted actions of mitogenic stimuli and apoptosis [1,2]. Apoptosis is a homeostatic process orchestrated by the host's genome of selective cell deletion without stimulating inflammatory response [3-5]. Earlier studies showed that apoptosis is activated in response to noxious stimuli e.g. starvation, inflammation, infection, irradiation, etc. More recent data suggested a physiological role for apoptosis, including the control of tissue development and differentiation, regulation of mitogenic effects, and control of cell death and loss of tissue with aging, and dysregulation of apoptotic cell-death has been implicated in states of disease [6].

Apoptosis is believed to be a process of programmed cell death that may occur in multicellular organisms. Programmed cell death involves a series of biochemical events leading to a characteristic cell morphology and death, in more specific terms, a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Processes of disposal of cellular debris whose results do not damage the organism differentiate apoptosis from necrosis.

In contrast to necrosis, which is a form of traumatic cell death that results from acute cellular injury, apoptosis, in general, confers advantages during an organism's life cycle. For example, the differentiation of fingers and toes in a developing human embryo occurs because cells between the fingers apoptose; the result is that the digits are separate. Between 50 billion and 70 billion cells die each day due to apoptosis in the average human adult. For an average child between the ages of 8 and 14, approximately 20 billion to 30 billion cells die a day. In a year, this amounts to the proliferation and subsequent destruction of a mass of cells equal to an individual's body weight. Excessive apoptosis causes hypotrophy, such as in ischemic damage, whereas an insufficient amount results in uncontrolled cell proliferation, such as cancer.

Apoptosis may occur when a cell is damaged beyond repair, infected with a virus, or undergoing stressful conditions such as starvation. Damage to DNA from ionizing radiation or toxic chemicals can also induce apoptosis via the actions of the tumour-suppressing gene p53. The "decision" for apoptosis can come from the cell itself, from the surrounding tissue, or from a cell that is part of the immune system. In these cases, apoptosis functions to remove the damaged cell, preventing it from sapping further nutrients from the organism, or halting further spread of viral infection.

As discussed further below, apoptosis may also play a role in preventing cancer. If a cell is unable to undergo apoptosis because of mutation or biochemical inhibition, it continues to divide and may develop into a tumor. For example, infection by papillomaviruses causes a viral gene to interfere with the cell's p53 protein, an important member of the apoptotic pathway. This interference in the apoptotic capability of the cell plays a role in the development of cervical cancer.

In an adult organism, the number of cells is kept relatively constant through cell death and division (i.e., proliferation). Cells must be replaced when they malfunction or become diseased, but proliferation must be offset by cell death. This control mechanism is part of the homeostasis required by living organisms to maintain their internal states within certain limits. Homeostasis is achieved when the rate of mitosis (cell division) in the tissue is balanced by cell death. If this equilibrium is disturbed, one of two potentially fatal disorders may occur: i) the cells are dividing faster than they die, effectively developing a tumor; or ii) the cells are dividing slower than they die, causing cell loss.

Homeostasis involves a complex series of reactions, an ongoing process inside an organism that calls for different types of cell signaling. Any impairment can cause a disease. For example, dysregulation of signaling pathway has been implicated in several forms of cancer. The pathway, which conveys an anti-apoptotic signal, has been found to be activated in pancreatic adenocarcinoma tissues.

A. Mechanisms of Apoptosis

Histologically, apoptosis may be characterized by DNA fragmentation, chromatin condensation, membrane bleeding, cell detachment from the extracellular matrix, cell rounding and shrinking, and alterations in plasma membrane lipid organization. Usually, the final stages of apoptosis are induced by a series of proteolytic enzymes termed caspases, which cleave and activate each other in a cascade of proteolysis [14], terminating with the effector caspases 7 and 3 [15].

Several cellular pathways are involved in the activation of the caspase family of proteases and the induction of apoptosis. In one embodiment, the present invention contemplates a method wherein apoptosis may involve pathways including, but not limited to: a) the intrinsic mitochondrial pathway; or b) the extrinsic death-receptor pathway. [16]

Apoptosis via the intrinsic pathway is characterized predominantly by mitochondrial changes. Effects are triggered by stimuli that cause mitochondrial disturbances and DNA damage (such as cancer therapeutic agents and ionizing irradiation), oxidative stress, hypoxia, cell detachment, and cellular distress [17]. Signals from these diverse stimuli converge upon the mitochondria, where propagation of the apoptotic signal is regulated by proteins that either promote (e.g. Bax, Bak, Bok, Bad, Bid, Bik, Bim, Bcl-Xs, Krk, Mtd, Nip3, Nix, Noxa, and Bcl-B) or suppress apoptosis (e.g. Bcl-2, Bcl-XL, Mcl-1, Bfl-1/Al, Bcl-W, and Bcl-G) [18,19]. Pro-apoptotic signals trigger permeabilization of the mitochondrial outer membrane, and facilitate the release of proteins from the mitochondrial intermembranous space into the cytoplasm, including cytochrome c and Smac/Diablo. The released cytochrome c then binds the caspase adaptor apoptotic protease-activating factor-1 (Apaf-1), thereby activating procaspase 9 and forming the apoptosome complex [20]. The apoptosome activates several downstream effector caspases, such as caspases 6, 7 and 3, leading to DNA fragmentation and cell death [21,22]. The effects of pro-apoptotic signals can be modulated by inhibitors of apoptosis proteins (IAPs), e.g. c-IAP1, c-IAP2, NAIP, Survivin, XIAP, Bruce, ILP-2, and Livin [23]. IAPs directly inhibit caspases and/or catalyze their ubiquitination and proteaseome-mediated degradation. This balance is finely regulated by endogenous inhibitors of IAPs, such as SMAC and HtrA2, which compete with active caspases to bind to IAP [24]. Anti-apoptotic signals such as Bcl-XL can bind and inactivate Apaf-1, and stimulate the release of Smac/DIABLO proteins from the mitochondria, thereby inactivating the IAPs [25].

The extrinsic pathway of apoptosis is a mechanism by which cells of the immune system trigger apoptosis in 'unhealthy' cells through ligand-mediated activation of cell surface death-mediating receptors, such as TNF Receptor 1 (TNFR1), TNF Receptor 2 (TNFR2), CD95/Fas/Apo1, and Death Receptors (tumor necrosis factor-related apoptosis-inducing ligand [TRAIL]-TRAIL receptors) 3-6 (DR3-6) [15,17].

Binding of these receptors by their respective ligands leads to receptor oligomerization and recruitment of death signal adaptor proteins. For example, binding of Fas ligand (Fas-L) to Fas, or TRAIL to TRAIL-R1 [26] leads to recruitment of FADD (Fas-associated death domain), and binding of TNF to TNFR1 leads to recruitment of TRADD (TNFR-associated death domain) [22]. The oligomerized receptors and recruited FADD or TRADD form a complex termed DISC (death-inducing signaling complex), which can bind to initiator caspases (caspase 8 and 10), followed by triggering the activation of caspases 7 and 3, and leading to apoptosis [13,15].

Recent studies underscore deficiencies in the arbitrary classification of intrinsic and extrinsic apoptosis pathways. First, some signals can activate both pathways, and an extensive crosstalk exists between these two apoptosis pathways. For instance, the transcription factor NF-kβ can activate the transcription of anti-apoptotic genes such as FLIP, Bcl-XL, XIAP and cIAP1; however, NF-kβ can also enhance the expression of apoptosis-inducing genes such as Fas, Fas-L, TRAIL-R1 and TRAIL-R2 [27].

Recent data has further suggested that the extrinsic death-receptor pathway is not limited to cells of the immune system, and that growth control of 'unhealthy' cells operates in most/all tissues containing proliferating cells. Thus, the $P2X_7$ receptor mechanism controls growth of certain types of epithelial cells, under normal physiological conditions, and, as contemplated herein, impaired $P2X_7$-mediated apoptosis could contribute to the neoplastic transformation in those tissues. Those discoveries suggest a physiological role for apoptosis in maintaining cellular homeostasis.

The improved understanding of apoptosis has provided a basis for targeted therapies that can induce death of cancer cells or sensitize them to established cytotoxic agents and radiation therapy [24,28,29]. Previous reports outlined agents and methods that suggest selective induction of apoptosis in cancer cells might be potentially useful in cancer therapy [reviewed in 13,24,25,30-32]. Such apopotic mechanisms include, but are not limited to, i) activation of the cell surface death receptors Fas, TRAIL and TNF receptors; ii) inhibition of cell survival signaling via EGFR, MAPK and PI3K; iii) altering the balance between pro-apoptotic and anti-apoptotic members of the Bcl-2 family; iv) down-regulating anti-apoptosis proteins such as XIAP, surviving and c-IAP2; e) proteasome inhibitors; f) nonsteroidal anti-inflammatory drugs (NSAIDs) and COX-2 inhibitors; g) peroxisome proliferator-activated receptor (PPAR) ligands; or h) DNA methylation.

Despite the expanse of present research, however, only a small number of therapies directly targeting the apoptotic pathways have advanced into clinical testing, and none have yet achieved approval by the United States Food And Drug Administration. Of the clinical trials that were initiated using agents such as those listed above, many were of limited value because of problems including, but not limited to: i) low efficacy [33]; ii) toxicity [34]; iii) presence of decoy receptors (DcR1, DcR2, and osteoprotegerin) which bind TRAIL and inhibit apoptosis [35]; iv) concerns of inducing immunodeficiency with hypogammaglobulinemia; or v) predisposition to develop lymphomas [36].

B. Apoptosis and Cancer

Defective apoptosis may play a role in the development of cancers [7-9]. In fact, one of the hallmarks of cancer is the development of mechanisms that evade apoptosis, and the loss of pro-apoptotic signals and gain of anti-apoptotic mechanisms contribute to tumorigenesis and the cancer phenotype. Thus, defective apoptotic mechanisms allow genetically unstable cancer cells to avoid elimination and confer resistance to cancer treatments [10-11]. Since apoptosis does not elicit inflammatory or immune response, this type of cell death is the preferred way of cancer cell killing by various treatments. The selective induction of apoptosis in cancer cells is emerging as a promising therapeutic approach for many cancers [13], and modulating the apoptotic pathways may be involved in mechanisms including, but not limited to, i) inducing tumor-cell death; ii) increasing responses to chemotherapy, radiotherapy and other targeted therapies; or iii) prevention of the neoplastic transformation.

Levels of the functional $P2X_7$ receptor in cancer epithelial cells of the ectoderm, the uro-genital sinus, and the distal paramesonephric duct are reported to be lower compared to normal cells (infra). The lesser expression of the $P2X_7$-receptor could be the result of the neoplastic transformation. Thus, in endometrial and bladder cells low expression of the $P2X_7$ receptor was found already in pre-cancerous and early cancerous cells, but not in hyperplastic benign cells [39,82,104]. As the data presented herein demonstrates, the carcinogenic process could have induced reduced expression of the $P2X_7$ at early stages of cancer development. Alternatively, the neoplastic transformation could have been triggered preferentially in cells expressing low levels of the receptor. This possibility is supported by data in uterine cervical epithelia, where low expression of the $P2X_7$ receptor was found already in dysplastic (precancerous) cells [39,82,104]. Few cases of dysplasia progress to cancer [109], so it is possible that low expression of the receptor preceded the neoplastic transformation. Accordingly, cells harboring defective $P2X_7$ expression mechanism have escaped apoptosis, and were rendered susceptible to carcinogenic stimuli and the neoplastic transformation.

In both scenarios, low expression of the $P2X_7$ receptor could promote cancer development, because decreased apoptosis due to reduced receptor expression can facilitate the growth of neoplastic cells. A recent study tested the hypothesis that in tissues at risk for undergoing malignant transformation augmentation of $P2X_7$-mediated apoptosis could inhibit cancer development [55].

II. P2X Receptor Family

The human $P2X_7$ receptor gene is localized to chromosome 12q24 and comprises 13 exons. Buell et al., "Gene structure and chromosomal localization of the human $P2X_7$ receptor" Receptors Channels 5:347-354 (1998). Some genetic mutations in the $P2X_7$ receptor gene have been described, but none regarding cervical cancer. Feng et al., "A truncated $P2X_7$ receptor variant ($P2X_{7-j}$) endogenously expressed in cervical cancer cells antagonizes the full-length $P2X_7$ receptor through hetero-oligomerization" J Biol Chem. 281:17228-17237 (2006). Since the overall prevalence of known chromosomal abnormalities in cervical cancers is low, genetic mutations cannot be considered the main etiological factor of the disease.

It has been reported that the $P2X_7$ receptor may belong to the P2X sub-family of P2 nucleotide receptors which are membrane-bound, ligand-operated channels. Buell et al, 1996; Soto et al, 1997; Dubyak and el-Moatassim, 1993; Ralevic and Burnstock, 1998; Khakh et al, 2001. For example the nucleotide, adenosine triphosphate (ATP), is believed to be a naturally occurring $P2X_7$ receptor ligand. Dubyak and el-Moatassim, 1993; Ralevic and Burnstock, 1998. ATP has been reported to be constitutively secreted by cells wherein ATP levels in extracellular fluids may be present in a low micromolar range. Sperlágh et al, 1998; Grahames et al, 1999; Henriksen and Novak, 2003; Loomis et al, 2003; Wang et al, 2004a. Early studies suggested that, in contrast to other types of ATP receptors, activation of the $P2X_7$ receptor might require a relatively high concentration of ligand. Ralevic et al., "Receptors for purines and pyrimidines" Pharmacol Rev 1998, 50:413-492. However, the data shown herein demonstrate that a threshold effect of $P2X_7$-mediated apoptosis occurs at nanomolar concentrations of ATP, suggesting that ATP levels which are present in the extracellular fluid are sufficient to activate the $P2X_7$ receptor.

One cellular effect of $P2X_7$ receptor activation may involve the formation of pores in the plasma membrane. Wang et al., "Anti-apoptotic effects of estrogen in normal and in cancer human cervical epithelial cells" Endocrinology 2004, 145: 5568-5579. For example, in uterine epithelial cells, formation of $P2X_7$ receptor pores induces apoptosis by a mechanism believed to involve influx of $Ca^{2+}$ via the $P2X_7$-pores in parallel with an activation of the mitochondrial-caspase-9 pathway. North R A, "Molecular physiology of P2X receptors" Physiol Rev 2002, 82:1013-1067; Wang et al., "Anti-apoptotic effects of estrogen in normal and in cancer human cervical epithelial cells" Endocrinology 2004, 145:5568-5579; and Feng et al., "A truncated $P2X_7$ receptor variant ($P2X_{7-j}$) endogenously expressed in cervical cancer cells antagonizes the full-length $P2X_7$ receptor through hetero-oligomerization" J Biol Chem 2006, 281:17228-17237. $P2X_7$ receptor activation by a brief exposure to extracellular ATP has been reported to open cation channels that apparently allow $Ca^{2+}$, $Na^+$ and $K^+$ influx. Surprenant et al, 1996. Further, a longer exposure to ATP may induce pore formation in the plasma membrane. Virginio et al, 1999.

The $P2X_7$ receptor is believed to play a role in cell growth because the receptor is expressed by proliferating cells. Li et al., "The $P2X_7$ Receptor: A novel biomarker of uterine epithelial cancers" Cancer Epidemiol Biomarkers Preven 2006, 15:1-8. Further, it has been reported that activation of the $P2X_7$ receptor induces apoptosis thereby having a regulatory impact on cell growth. Wang et al., "EGF facilitates epinephrine inhibition of $P2X_7$-receptor mediated pore formation and apoptosis: a novel signaling network" Endocrinology 2005, 146:164-174.

$P2X_7$-mediated apoptosis may also involve intracellular signaling mechanisms including, but not limited to, IL-1β (Ferrari et al, 1997a), TRAIL (Aggarwal et al, 1999), p38/JNK/SAPK (Humphreys et al, 2000) and NF-κB (Ferrari et al, 1997b). Other cellular effects of $P2X_7$ receptor activation may be determined by receptor synthesis (Guerra et al, 2003), glycosylation (Feng et al, 2005), trafficking and plasma membrane localization (Li et al, 2000; Bobanovic et al, 2002; Gu et al, 2000), oligomerization (Khakh et al, 2001; Feng et al, 2006), and post-activation internalization, recycling and degradation (Wang et al 2005; Feng et al, 2006).

Until recently, relatively little was known about the in vivo biological role of the P2X$_7$ receptor. Earlier studies suggested involvement of the P2X$_7$ receptor in inflammatory and immune processes since the receptor is expressed in the islets of Langerhans and inflammatory dendritic epidermal cells and in cultured immature dendritic epidermal cells. Georgiou et al. 2005; Mutini et al, 1999. Overexpression of P2X$_7$ was found in lesional skin of psoriasis and atopic dermatitis, where an intense P2X$_7$ immunoreactivity was confined to the cell membrane of the basal layer. Pastore et al, 2007. P2X$_7$ has been suggested to play a role in chemokine secretion by normal keratinocytes but available data are inconsistent. For example, one study reported that the treatment of cultured normal keratinocytes with the P2X$_7$ specific agonist 2',3'-0-(4-benzoylbenzoyl)-adenosine 5'-triphosphate (BzATP) increased IL-6 release, while a second report found that BzATP decreased chemokine secretion. Inoue et al, 2007; and Pastore et al, 2007, respectively.

Studies have also suggested a role for P2X$_7$ in the control of epidermal growth, but most studies were observational. The P2X$_7$ receptor expression has been found in: i) normal tissues, Greig et al, 2003a; ii) precancerous epidermal tissues, Slater and Barden, 2005; and skin cancer cells, Greig et al, 2003b; White et al, 2005; and Pastore et al, 2007. P2X$_7$ receptor immunoreactivity was found throughout the epidermis, including in the basal/parabasal germinative regions of the epidermis. Greig et al, 2003a. P2X$_7$ receptors were detected as early as 8-11 weeks in human fetal epidermis cells (i.e., for example, periderm), wherein the receptors co-localized with caspase-3 and TUNEL staining. Greig et al, 2003c. Co-localization of the P2X$_7$ receptors with such apoptosis-related markers was also reported in adult human epidermis, and recent studies reported BzATP-induced cell death in normal and cancer keratinocytes. Greig et al., 2003a, Greig et al, 2003b; and Slater & Barden, 2005.

Although these existing observational data suggest that the P2X$_7$ may regulate growth of epithelial cells little is known about the biological role of the P2X$_7$ receptor in the epidermal layers. For example, no previous studies have investigated experimentally the biological role of the P2X$_7$ receptor in vivo. The data presented herein demonstrates that P2X$_7$ receptors have an in vivo physiological role in the control of growth of epidermal epithelial cells. The data also suggest that this growth control may occur through apoptotic mechanisms, and that pharmacological stimulation of the receptor could inhibit development of epidermal neoplasia. For example, the presented data collected in cultured human normal keratinocytes and/or cancer keratinocytes provide direct evidence that P2X$_7$ receptors control the growth of cells through regulation of apoptosis. Specifically, in vivo mouse data discussed below show that locally applied P2X$_7$ receptor agonists inhibit DMBA/TPA-induced papilloma formation.

The translated product of the human P2X$_7$ transcript is a 595 aa linear polypeptide, predicted to traverse the plasma membrane and to possess two intracellular domains and an extracellular domain with the following topology. See, FIG. 21A. The P2X$_7$ polypeptide may comprise the following regions:

a) N-terminus (aa 1-25), which forms intracellular complexes with several proteins including β2 integrin, receptor-like tyrosine phosphatase (RPTP), α-actin, phosphatidylinositol 4-kinase, membrane-associated guanylate kinase, and several heat shock proteins [45]. These complexes may mediate some P2X$_7$-dependent signaling b) The first transmembrane segment (aa 26-46)

c) Extracellular domain (aa 47-334), which contains the ligand binding site [46-49], and five putative N glycosylation sites [43], of which Asn187, Asn213, and Asn241 are required to confer functionality [Ref. 50; and Gorodeski, unpublished data]

d) The second transmembrane segment (aa 335-355).

e) A long C-terminus (aa 356-595) [43] that is required for pore formation [50,51]. Domains within the carboxy-terminal tail of the P2X$_7$ also direct trafficking and stabilize expression of the receptor in the plasma membrane [50-54].

The functional P2X$_7$ receptor is a glycosylated G-coupled membrane-bound protein. See, FIG. 21D. [41,42,47,48,55]. The natural ligand of the P2X$_7$ receptor is ATP. See, FIG. 21B. [47,48]. ATP is present in extracellular fluids at high nanomolar, low micromolar concentrations [40,56-60], which suffice to activate the receptor [38,40-42,55]. Regulation of ATP in extracellular fluids was described [e.g. 46,61,62].

Activation of the P2X$_7$ receptor by ATP can stimulate various signaling pathways including the IL-1β [63], TNFα-TRAIL [64], and the p38, JNK/SAPK [65] and NF-kβ cascades [66], some of which can induce apoptosis. In epithelial cells, the quantitatively significant pro-apoptotic P2X$_7$ effect involves formation in the plasma membrane of pores with a diameter of ~4 nm that allow influx of molecules of 400-900 daltons. See, FIG. 21E. [38,40-42,49,55]. In its maximal size, the pore is relatively permeable to $Ca^{2+}$, but it remains selective to other cations and is impermeable to anions [49]. P2X$_7$ pore formation involves recruitment to the plasma membrane of receptor molecules [67-69] and pannexins [70,71], and the formation of complexes composed of receptor tri-oligomers. See, FIG. 21D. [47-50]. P2X$_7$ molecules can also form structural interactions with P2X$_4$ receptor molecules [73,74], which may stabilize the pores [75].

In epithelial cells e.g. human uterine ectocervical, endocervical and endometrial cells and human keratinocytes, activation of the P2X$_7$ receptor induces pore formation and uncontrolled influx of Ca2+, which triggers mitochondrial damage followed by activation of caspase 9/7/3-mediated apoptosis. See, FIG. 21F. [38,40-42,55].

Similar to other G-coupled protein receptors, activation stimulates GRK-3-mediated phosphorylation of the P2X$_7$ receptor on tyrosine, serine, and threonine residues, and recruitment of β-arrestin-2 to the plasma membrane [42]. β-arrestin binding facilitates uncoupling of the receptor from the heterotrimeric G proteins, and the activated phosphorylated receptor molecules participate in the stimulation of various signaling pathways [42]. However, most of the remaining activated receptor molecules are internalized by endocytosis, and 13-arrestin binding targets the receptor in a dynamin-related mechanism to clathrin-coated pits. Endocytosis is followed by receptor sequestration into various cellular domains, recycling, and degradation. See, FIG. 21D. [42].

A Biochemistry

P2X$_7$ is one of a number of pro-apoptotic systems that operate in epithelial tissues [37,38]. The P2X$_7$ receptor is expressed by proliferating cells [39], and activation of the receptor induces apoptosis that controls directly the growth of the epithelial cells [38,40-42].

The human P2X$_7$ gene is localized within a 55 kb region of chromosome 12q24; it has 13 exons that encode a 595 amino acid (aa) polypeptide [43]. The P2X$_7$ transcription initiation site (TpIS) is adenine (+1) at nucleotide (nt) 1683 of the human P2X$_7$ gene [GenBank Y12851]), with a TTAAA sequence at nt −32/−28 and an active promoter region within nt −158/+32 [44].

The low affinity of the P2X$_7$ receptor for ATP ($EC_{50}$ of 100 μM) and BzATP ($EC_{50}$ of 35 μM) [38,40,42,55] is unusual relative to the proposed physiological significance of the P2X$_7$ receptor mechanism to apoptosis, since extracellular steady-state levels of ATP are only in the high nanomolar, low micromolar range. This question could be answered by reference to the biological role of the receptor. In epithelial cells, the $P2X_7$ receptor controls the growth of cells through the induction of apoptosis [38]. A high affinity of the $P2X_7$ receptor for its natural ligand ATP would be disadvantageous to normal cells because the receptor would be activated continuously and induce cell death. Cells have apparently devised mechanisms to regulate expression and activity of the $P2X_7$ receptor, and the low affinity of the receptor could be an additional physiologic mechanism to control receptor activation and to avoid cell death. See, FIG. 22. Under normal conditions, the extracellular levels of ATP are in the range that corresponds to the threshold level for receptor activation [38, 40,42,49,55]. Accordingly, only a fraction of the receptor pool would be activated, and only few cells are likely to undergo apoptosis. This hypothesis is supported by the mouse data in vivo that in the normal skin the degree of baseline apoptosis in $P2X_7$-receptor-expressing keratinocytes is low. See, FIGS. 26C and 26L, [55].

B. Cellular Localization

The limiting factor of $P2X_7$-mediated apoptosis is cellular expression of the $P2X_7$ receptor [42,50]. Localization of the $P2X_7$ receptor has been studied by employing immune methods, and $P2X_7$ immunoreactivity was found in different cellular locations. Co-localization in the plasma membrane reflects foremost the full-length active receptor [42,50], although truncated forms (e.g. the $P2X_{7-j}$ protein) can be also sorted to the plasma membrane [50]. $P2X_7$ immunoreactivity found in the cytoplasm reflects newly formed receptor en route to be inserted into the plasma membrane, or post-activation internalized, degraded, or recycled receptor [50]. Perinuclear/nuclear $P2X_7$ immunoreactivity was described in epithelial [76-78] and non-epithelial cells [79,80], but its biological significance is unclear.

In some types of epithelial tissues, e.g. the cervix and endometrium, the $P2X_7$ receptor is sorted predominantly into apical domains of the plasma membrane [81,82]. In the endometrium, apical expression of the receptor depends on the level of tissue differentiation, and sorting into apical regions of the plasma membrane is highest in tissues of women at the late proliferative phase of the menstrual cycle [82]. The biological significance of these findings is unclear.

C. Regulation

One factor that determines activity of the $P2X_7$ system is the degree of expression in the plasma membrane of the full length functional receptor [42,50]. The $P2X_7$ system is a potent pro-apoptotic factor in vivo, and cells have developed mechanisms that regulate and control expression and function of the receptor [55].

1. Transcription Regulation $P2X_7$ transcription is regulated by two groups of cis-regulatory enhancer element(s) located within nt regions +222/+232 and +403/+573 downstream of the active promoter. See, FIG. 22. [44]. Correlative data suggest that these regions contain binding sites for transcription factors p300, Elk-1, E47, EIIaE, E2F, and p53 [44], which can integrate signals from enhancer and promoter regions and regulate cell growth and apoptosis [83-90]. The repression or absence of some of these transcription factors, e.g. E47 [85] and p53 [90], have been implicated in cancer development. The tumor suppressor p53 controls expression of genes involved in the regulation of cell cycle progression and cell death [90], and $P2X_7$ expression correlates with p53 protein levels [91], and with activation of the p53 apoptotic pathway [92].

$P2X_7$ transcription is controlled by methylated cytosines at cytosine-phosphodiester-guanosines (CpG) sites that cluster or co-localize with the enhancers' sites. See, FIG. 22. [44]. Cytosines at CpG sites +211/+212 +330/+331 and +461/+464 are constitutively methylated in vivo, and hypermethylation of these sites inhibits $P2X_7$ transcription [44]. Conversely, treatment of cells with de-methylation drugs, e.g. 5-aza-2'-deoxycytidine (Aza-dC) upregulates $P2X_7$ mRNA, possibly by inducing de-methylation of cytosines at the CpG sites +211/+212 +330/+331 and +461/+464 [44]. The molecular mechanism by which hypermethylated CpGs downstream of the $P2X_7$ promoter inhibit transcription possibly involves modulation of the spatial conformation of transcription factors recognition sites within the putative enhancers regions [44].

2. Post-Transcriptional Regulation

The full-length human $P2X_7$ 3'-untranslated region (3'UTR) contains sequences that confer instability to the $P2X_7$ transcript [93,94]. Human poly(ADP-ribose) polymerase (PARP) interacts with transcribed $P2X_7$ mRNA and de-stabilizes the (3'UTR)-$P2X_7$ mRNA [93]. In contrast, inhibition of PARP augments $P2X_7$-related apoptosis by increasing stability of the $P2X_7$ mRNA. See, FIG. 22.

The human $P2X_7$ 3'UTR also contains target sites for micro-RNAs (miRNA), which are small noncoding 18-25 nt RNAs that regulate mRNA targets [95]. The human $P2X_7$ 3'UTR contains binding sites for miR-186 and miR-150, which confer instability to the $P2X_7$ transcript [94]. Overexpression of miR-186 and miR-150 inhibits synthesis of $P2X_7$ mRNA [94], while inhibition of miR-186 and miR-150 upregulates synthesis of $P2X_7$ mRNA [94] and increases ligand-induced $P2X_7$ pro-apoptotic effects. See, FIG. 22. [94, 96].

3. Regulation of Receptor Glycosylation

Membrane expression and functionality of the $P2X_7$ receptor depend on glycosylation of the receptor. Glycosylation facilitates Golgi transport, trafficking, and insertion of the receptor into the plasma membrane, while receptor de-glycosylation abrogates receptor function [41]. Glycosylation of the $P2X_7$ receptor is controlled by (β2-adrenoceptor (β2-AR)—activation of protein kinase-A (PKA), resulting in de-glycosylation of the $P2X_7$ receptor and enhanced receptor degradation [41]. The PKA effect is regulated by the action of the epidermal growth factor (EGF); it involves facilitated, phosphoinositide 3-kinase (PI3K)-dependent inhibition of β2-AR internalization, and facilitated β2-AR recycling, thereby increasing the pool of β2-ARs in the plasma membrane that are available for activation upon ligand binding. See, FIG. 21D and FIG. 22. [41].

4. Regulation of Receptor Oligomerization $P2X_7$-mediated apoptosis involves ligand-induced pore formation [47-49], which depends on homo(tri)-oligomerization of the full-length receptor. See, FIG. 21E. [47-50]. Oligomerization of the $P2X_7$ receptor depends on the availability of $P2X_7$ monomers, and is influenced by the presence of truncated forms of the $P2X_7$ that can hetero-oligomerize with the full-length $P2X_7$ form and produce non-functional pores [50]. Five truncated variants of the human $P2X_7$ were previously reported ($P2X_{7-b}$, $P2X_{7-c}$, $P2X_{7-g}$, $P2X_{7-i}$, and $P2X_{7-j}$), resulting from alternative splicing [50,54,96]. All lack the carboxy terminus of the wild-type $P2X_7$ receptor, and some ($P2X_{7-b}$ and $P2X_{7-j}$) have been shown to be ineffective in pore formation and apoptosis induction when expressed singularly in host cells [50].

The $P2X_{7-j}$ form is expressed naturally in normal and in cancer epithelial cells [50]. It is composed of the proximal 248 amino-acids of the wild-type $P2X_7$ with an altered stretch of 10 amino-acids at its carboxy terminus. It lacks the distal 337 amino-acids of the $P2X_7$, including the entire intracellular carboxy terminus, the second transmembrane domain, and the distal third of the extracellular loop. When expressed heterologously, treatment with the $P2X_7$-specific ligand BzATP evokes minor channel activity but it fails to induce pore formation and apoptosis [50]. Co-expression in host cells of the $P2X_{7-j}$ plus the full-length $P2X_7$ results in hetero-oligomerization between the $P2X_{7-j}$ and the $P2X_7$, and the formation of nonfunctional $P2X_{7-j}/P2X_7$ hetero-oligomers [50].

Analysis of the oligomeric products in host cells co-expressing the $P2X_7$ plus the $P2X_{7-j}$ suggested formation of four types of trimeric complexes in the following order of relative expression. See, FIG. 21E. [50]:

$[P2X_{7-j}]^3$ (70%)
$[P2X_{7-j}]^2/[P2X_7]$ (15%)
$[P2X_7]^3$ (10%)
$[P2X_7]^2/[P2X_{7-j}]$ (5%)

Of these, only the $[P2X_7]^3$ forms a functional pore [50], indicating that co-expression of the $P2X_7$ plus the $P2X_{7-j}$ favors formation of inactive complexes. The data suggest that in cells expressing both receptor forms, abundance of the $P2X_{7-j}$ or paucity of the full-length $P2X_7$ receptor will increase the likelihood of formation of nonfunctional pores, and will tend to abrogate the induction of apoptosis. See, FIG. 22.

5. Estrogen Regulation of $P2X_7$-Mediated Apoptosis

In estrogen-responsive tissues, exposure to estrogen induces growth-promoting effects on cells. In the past it was believed that most of the effect involves activation of estrogen-dependent mitogenic stimuli. However, recent data show that some of the effect is the result of estrogen induced anti apoptotic effect. Experiments using human normal and cancerous estrogen-responsive uterine epithelial cells showed that estrogen inhibits baseline apoptosis (mediated primarily by the $P2X_7$-receptor [38]), as well as $P2X_7$-augmented apoptosis [40]. In these cells, the $P2X_7$-mediated apoptosis involves influx of $Ca^{2+}$ via $P2X_7$-pores and induction of apoptosis by the mitochondrial-caspase-9 pathway [38, 40-42]. Treatment with estrogen blocks $P2X_7$-receptor-induced activation of caspase 9, but the mechanism of apoptosis inhibition differs in normal and in cancer cells. In the normal cells, treatment with estrogen results in lower cytosolic calcium by attenuation of $P2X_7$-induced calcium-influx. In contrast, estrogen up-regulates activity of the anti-apoptotic factor Bcl-2 in cancer cells [40].

D. Biological Effects

Activation of the $P2X_7$ receptor stimulates numerous effects [46-49]. At the tissue/organ level the $P2X_7$ is involved in the innate immune response against microbial infections. Ligation of $P2X_7$ by ATP can stimulate inflammasome activation and secretion of proinflammatory cytokines such as IL-1β [e.g. 63, 97, 98], and the production of reactive oxygen species (ROS). In macrophages, $P2X_7$ stimulates ROS production through the MAPKs ERK1/2 and the nicotinamide adenine dinucleotide phosphate oxidase complex [99]. $P2X_7$ effects also regulate the function of the nervous [100], skeletal [101], and epithelial systems [102]. At the cellular level, non-apoptotic effects of $P2X_7$ receptor activation involve membrane responses, and alter profiles of cell surface lipid and protein composition that modulate the direct interactions of $P2X_7$-receptor-expressing cells with other cell types. The responses can also induce the release of bioactive proteins, lipids, and large membrane complexes into extracellular compartments for remote communication between $P2X_7$-receptor-expressing cells and other cells that amplify or modulate inflammation, immunity, and responses to tissue damage [103].

However, the hallmark of $P2X_7$ receptor activation is induction/augmentation of cell death. Early studies reported on the cytolytic effects of $P2X_7$ receptor activation in cells of the white lineage. Recent studies focused on the pro-apoptotic effects of $P2X_7$ receptor activation in epithelial cells.

1. Normal Epithelial Cell-Growth

Data in normal human epithelial uterine cells (i.e., for example, ectocervical, endocervical or endometrial) and epidermal cells, and in normal mouse epidermal keratinocytes, suggest that the $P2X_7$ system plays a physiological role in the regulation of epithelial cell growth for reasons including, but not limited to:

a) The $P2X_7$ receptor is both necessary and sufficient for controlling baseline apoptosis [38-42,50,55,94]
b) Blocking synthesis of the receptor abolishes baseline apoptosis [38-42,50,55,94]
c) Baseline apoptosis is the result of activation of the $P2X_7$ receptor by ATP [38-42,50,55,94]
d) ATP, the natural ligand of the $P2X_7$ receptor, is present in extracellular fluids at concentrations that suffice activation of the receptor [38,40,55]
e) ATP is constitutively secreted by cells, acting in a paracrine/autocrine manner [46-49]
f) Under normal physiological conditions other pro-apoptotic systems e.g. the Fas and the TNF mechanisms play a minor role in mediating baseline apoptosis [38]
g) In epithelial cells the $P2X_7$ receptor is expressed mainly in reserve cells that determine the proliferative capacity of the epithelium [39].

The expression profile of $P2X_7$ receptor in normal stratifying epithelia explains its fundamental role in the control of cell growth. In stratified epithelia, e.g. the uterine ectocervix [39,82] or the epidermis [55,76,105], cells proliferate from reserve cells that reside in the basal/parabasal layers. These cells rest on the basal membrane and continue to divide throughout life. In the skin, a large pool of reserve cells can be also found within hair shafts [105]. Superficial to the parabasal layer are layers of metabolically active cells (intermediate in the cervix, granular in the skin), and layers of cells undergoing terminal differentiation (superficial cells in the cervix, transitional cells in the skin). The skin, in contrast to non-keratinizing stratified epithelia (e.g. the cervix) also contains the superficial stratum corneum, composed of layer(s) of flat dead cells [105].

In normal stratifying epithelia, $P2X_7$ immunoreactivity is intense in basal/parabasal layers (and in hair shafts in the skin); lesser in the intermediate ectocervical layers of the epithelium and in the epidermal granular layers; and more intense in the superficial (ectocervix), and transitional and stratum corneum layers (skin) [39,76,82,104]. In contrast to the $P2X_7$ receptor protein, $P2X_7$ mRNA is found mainly in the basal/parabasal layers, but not in the more superficial layers [39]. Thus, the $P2X_7$ immunoreactivity in non-proliferating layers represents receptor trapped in dying cells that undergo terminal differentiation, and most likely it mediates the apoptosis that is associated with the terminal differentiation [105]. However, this function is secondary to its main role, which is regulation of growth of the proliferating reserve cells. Reserve cells are the target of carcinogenic stimuli and are at risk of undergoing neoplastic transformation; the intense expression of de-novo synthesized receptor in these cells suggests that the $P2X_7$ receptor controls directly the growth of the reserve cells [55].

2. Cancer Epithelial Cell-Growth

While $P2X_7$ receptor activation may augment apoptosis in both normal and cancer epithelial cells, some types of cancerous epithelial cells have a decreased apoptotic effect than in the respective normal cells. For instance, treatment with the P2X$_7$ receptor specific agonist BzATP of cancer ectocervical, endocervical, endometrial cells and cancer keratinocytes resulted in 2-5 fold lesser apoptosis than in the respective normal cells [38,40,55]. Baseline apoptosis, which in those cells is determined mainly by the P2X$_7$ system [38,40,55], was also smaller in the cancer cells than in the normal cells [38,40,55]. Recent data indicate that the attenuated P2X$_7$-mediated apoptosis in the cancer cells is due mainly to reduced cellular levels of the P2X$_7$ receptor (mRNA and protein) in the cancer cells [41,42,44,50,55,94].

Differences in P2X$_7$ receptor expression in cancer versus normal epithelial cells were described [82]. Recent studies using well-characterized immune methods to detect the functional full-length P2X$_7$ receptor reported that epithelia can be grouped relative to P2X$_7$ receptor expression as follows:

a) Epithelia with similar trend of expression in normal and cancer cells, e.g. the colon [82].
b) Epithelia with higher expression of the P2X$_7$ in cancer cells than in normal cells, e.g. thyroid [82,106].
c) Epithelia with lesser expression of the P2X$_7$ in cancer cells than in normal cells. These include epithelia derived from the ectoderm (skin and breast), the urogenital sinus (bladder and ectocervix), and the distal paramesonephric (Müllerian) duct (endocervix and endometrium) [39,50,55,76,82,104]. In those tissues P2X$_7$ expression is decreased already in early phases of the neoplasia.

Thus, early embryonic events may imprint the type of P2X$_7$ regulation of expression in later stages of life.

P2X$_7$ polymorphisms have been described and point-mutations have been identified in lymphocytes and monocytes, causing either loss-of-function, e.g. 1513A>C (E496A), 1729T>A (1568N), 946G>A (R307Q), 1068G>A (A348T), 1096C>G (T357S), and 1405A>G (Q460R); or gain of function, e.g. 489C>T (H155Y). A 1352T>C(P451L) change impairs cell death in murine thymocytes. Polymorphisms in the promoter region of the P2X$_7$ receptor has also been reported, and one variant was associated with protection against tuberculosis. Additional P2X$_7$ gene variants were included in the Single Nucleotide Polymorphism Consortium database, but their functional implications remain to be determined [50]. Numerous point-mutations were found in cancer epithelial cells, [data not shown], but there is no evidence that genetic mutations of P2X$_7$ influence the development of cancer in these tissues.

In contrast to genetic mutations, studies found that differences in the epigenetic control of transcription, mRNA stability, glycosylation, and oligomerization can explain the attenuated expression of the functional P2X$_7$ receptor in the cancer epithelial cells, for example:

Hypermethylation

Hypermethylation of genes can induce repression of tumor suppressor genes and lead to cancer development [107]. In uterine cervical cells CpG sites +193/+194 (and/or +211/+212), +330/+331, and +461/+462 (and/or +463/+464), in regions that co-localize with enhancers' sites, are direction-dependent inhibitory cis elements of P2X$_7$ transcription [44]. Data in cultured cervical cells and in cervix epithelial tissues in vivo showed that cytosines within these CpG sites are hypermethylated in the cancer cells [44]. Moreover, the hypermethylation of cytosines in CpG sites downstream of the P2X$_7$ promoter correlated with reduced expression of P2X$_7$ mRNA and protein in the cancer cervical cells [44], suggesting that decreased transcription of P2X$_7$ through hypermethylation of cis-regulatory elements plays a role in cancer development.

Steady State Levels

Low steady state levels of P2X$_7$ in cancer epithelial cells can be the result of enhanced degradation of the transcript through the action of micro-RNAs [94] miRNAs reside in genomic regions that are involved in the regulation of cell growth, and abnormally expressed miRNAs in human cancers can modulate the stability of transcripts of protein-coding genes involved in tumorigenesis or apoptosis [94]. Sequences within the human 3'UTR-P2X$_7$ express target sites for miR-186 and miR-150 that confer instability to the P2X$_7$ transcript [94]. Cancer epithelial cells express higher levels of micro-RNAs miR-186 and miR-150 than normal cells [94], and the increased expression of miR-186 and miR-150 stimulates degradation of the P2X$_7$ transcript preferentially in cancer cells.

Glycosylation

Glycosylation of the P2X$_7$ receptor is important for receptor function. In epithelial cells glycosylation of the P2X$_7$ receptor is controlled by the EGFR/PI3K/β2-AR/PKA systems, and activation of PKA by the β2-AR mechanism induces de-glycosylation of the P2X$_7$ receptor [41]. The β2-AR effect is facilitated by co-activation of the EGFR. which is often overexpressed in cancer epithelial cells. See, FIGS. 21D and 22, [41] and [108], respectively. Therefore, overexpression of the EGFR could contribute to neoplasia by two groups of mechanisms: via its pro-mitogenic influence; and by abrogation of P2X$_7$-mediated apoptosis (reduced expression of the P2X$_7$ receptor through PKA-mediated de-glycosylation of the receptor).

Splicing Variants

Nine splice variants of the human P2X$_7$ resulting from alternative splicing were previously reported, of which the P2X$_{7-j}$ is the most prevalent in epithelial cells. The P2X$_{7-j}$ can hetero-oligomerize with the full-length receptor, and lead to the formation of inactive complexes. In contrast to the full length P2X$_7$, which is reduced in some types of cancer cells, the expression of the P2X$_{7-j}$ in those cells is relatively stable. This imbalance would favor the formation of inactive P2X$_{7-j}$/P2X$_7$ hetero-oligomers leading to defective apoptosis and augmented growth of the cancer cells. See, FIG. 21E, [50].

III. Cancer Treatment

Some reports suggest that pro-apoptotic activity mediated by the P2X$_7$ receptor could be potentially used as a cancer treatment and cancer prevention in humans [110]. Until the present invention, however, the development of such an anti-neoplastic modality was not clinically relevant because target tissue specificity and an understanding of the pharmacological properties of an effective therapeutic was not understood.

It is currently believed that a P2X$_7$ receptor is member of the family of ATP-dependent P2 nucleotide purinergic receptors. Early data on the anti-neoplastic properties of P2 receptors agonists prompted in vivo studies using systemic or intraperitoneal treatments with ATP, the natural ligand of P2 receptors. [111]

Cancer treatments using intravenous infusions of ATP in patients with advanced cancers have been reported. For example, a randomized clinical trial in patients with advanced non-small-cell lung cancer has shown beneficial effects of ATP treatment on fatigue, appetite, body weight, muscle strength, functional status, quality of life, and serum albumin concentrations, with marked effects in cachectic patients [112]. ATP treatment was associated with increased survival in the subgroup of weight-losing patients (9.3 months in ATP-treated patients versus 3.5 months in control patients); however, ATP had no effect on tumor stage and survival within the entire study group [113]. The data suggested that the beneficial effects of ATP on body fat, fat-free and body cell mass, and on energy intake were due to the maintenance of energy intake by restoration of hepatic energy levels. [114], [115], respectively.

Although the above studies suggest that palliative care of terminally ill cancer patients might be useful using intravenous ATP, it is evident in retrospect that the use of systemic ATP as an-anti cancer modality was likely to fail. Systemic administration of ATP will target P2 receptors throughout the body. Cells express more than one type of P2 receptors, and responses to ATP depend on the type of P2 receptors that are activated. Also, depending on cell type, activation of some receptor subtypes (i.e., for example, $P2Y_1$, $P2X_5$, and $P2X_7$) leads to a decrease in cell number, whereas activation of other receptor subtypes (i.e., for example, $P2Y_2$) can lead to an increase in cell number [116]. In addition, in some cell types e.g. peripheral T lymphocytes, activation of the $P2X_7$ receptor can produce mitogenic response [117].

ATP instability is another factor that could negatively affect ATP's efficacy such as by ectoATPase degradation in extracellular fluids [118]. For example, anti-cachectic effects could have occurred by a breakdown product of ATP, adenosine, which is effective at reducing weight loss [119]. Ecto-ATPases are known in the plasma and extracellular fluids [61]. Further, it is unlikely that ATP reached a concentration range that is required for pharmacological activation of the $P2X_7$ receptor [38,40,42,55].

Thus, the lack of tissue specificity and the poor understanding of ATP pharmacology following the systemic administration of ATP at the time of these studies provide a rationale for their clinical failure.

Recent studies have examined the effects of intraperitoneal administration of ATP on tumors resulting from implanted prostate and bladder carcinomas cells in nude mice [120], [121], respectively. The data showed a 44-69% reduction in the growth of freshly implanted cancer cells, with no adverse effects on the host mice. The growth reduction of the implanted bladder and prostate cancers provides proof-of-concept for the anti-neoplastic effect of ATP. [119]. Based on these considerations, the art suggests that the use of ATP as an anti-neoplastic modality could produce non-specific responses, and that ATP should not be used as an anti-neoplastic treatment modality in humans. Instead, one should focus on the use of P2 receptor modulators (i.e., for example, agonists or antagonists) that are selective for mediating the growth of cancer cells [116].

In one embodiment, the present invention contemplates a composition comprising BzATP as one such ATP agonist. BzATP was used to activate $P2X_7$-mediated apoptosis and modulate growth of epidermal neoplasia. [55} BzATP was synthesized and used initially as a photoactivatable, covalently binding affinity probe to study site-specific adenine nucleotide binding to the ATPase of submitochondrial particles [122]. In contrast to ATP which behaves in aqueous solutions as a weak acid ($ATP^{4-}$), BzATP has lipophilic characteristics that are contributed by the benzoyl-benzoyl ring, and which could explain its penetration through the epidermis. See, FIG. 21C. BzATP is a relatively stable compound in biological solutions and across a broad range of temperatures and pH, although serum albumin and various plasma lipids can bind BzATP and reduce its potency at $P2X_7$ receptors [123]. BzATP is commercially available in the form of either 2'(3')-O-(4-benzoyl-benzoyl)adenosine-5'-triphosphate ($C_{24}H_{24}N_5O_{15}P_3$, MW=715.39) or the tri-triethylammonium salt, $C_{24}H_{24}N_5O_{15}P_3 \cdot C_{18}H_{45}N_3$, MW=1018.97). Both BzATP forms have been shown to exert similar anti-apoptotic effects. (data not shown)

BzATP is a potent and efficacious ligand of the $P2X_7$ receptor, with a 5-10 fold greater potency than ATP [42,50]. Activation of the $P2X_7$ receptor requires the continued presence of the ligand, and treatment with BzATP exerts a prolonged $P2X_7$ effect [124]. In most studied cell types BzATP has been showed to be a specific $P2X_7$ receptor agonist [46-48], but in some cell types BzATP can act as a weak agonist, or a weak antagonist, depending upon the particular P2 receptor subtype: i) $P2Y_1$ [125-127]; ii) P2Y2 [128], and iii) $P2X_1$, $P2X_2$, and $P2X_3$ receptors [48,129]. A study in hippocampal mossy fibers suggested that BzATP can be catabolized extracellularly by ecto-nucleotidases to Bz-adenosine, which can then be transported intracellularly via nucleoside transporters. [130]. Once transported intracellularly, the benzoyl-benzoyl group can be removed by intracellular esterases and the adenosine is released into the extracellular space thereby activating adenosine receptors.

Despite those isolated reports, most studies using BzATP concur that the predominant observed effects are the result of activation of the $P2X_7$ receptor [131]. Various epithelial cell types, including human and rodents' keratinocytes, have indicated that BzATP effects are not mediated by degradation products of BzATP (e.g. Bz-adenosine 5'-diphosphate ADP [BzADP], adenosine 5'-monophosphate [AMP], or adenine). In addition, treatments with adenosine 5'-diphosphate (ADP), AMP, adenosine, or adenine had no pro-apoptotic effects on the cells. (data not shown).

The data presented herein demonstrates that BzATP applied locally on the skin, at areas at risk for developing skin papillomas and cancers, showed 50% inhibition of papillomas and skin cancers in animals that were treated with BzATP. It is further shown that a main target of BzATP treatment are $P2X_7$-receptor-expressing reserve cells. In the normal skin, BzATP augmented apoptosis of the reserve cells without evoking inflammatory or atrophic changes, which potentially could have been induced by activation of the $P2X_7$ receptor [46-49]. Specifically, BzATP did not induce tissue loss, thinning, or ulceration. In contrast, treatment with BzATP inhibited papilloma formation, and it inhibited the transformation of papillomas to skin cancers. In the DMBA/TPA mouse model, most early papillomas are histologically benign, but some will progress to squamous cell carcinoma [132,133]. Papillomas at risk for developing into cancer are characterized by increased proliferative capacity of epidermal reserve cells [132]. $P2X_7$-mediated apoptosis has little effect on slow growing normal cells, but it controls the proliferation of rapidly growing cells, while BzATP has the potential for skin chemoprevention by controlling the development of precancerous cells and their transformation into skin cancers. [55] BzATP also induced apoptosis of advanced cancer cells in vivo, but the effect was limited by the low expression of the $P2X_7$ receptor in these cells. See, FIGS. 26T,26V and FIGS. 26S,26U, respectively. $P2X_7$ receptor levels can be increased in normal and in cancer cells by inducing de-methylation of cytosines at CpG sites that control $P2X_7$ transcription. See, FIG. 22; [44].

Collectively, these data suggest that the pharmacological augmentation of $P2X_7$-mediated apoptosis are prophylatic for skin cancers, and therapeutic for early skin cancerous lesions.

The initial studies utilized a low BzATP dose of the BzATP and did not result in any local or systemic adverse events. This implies that when administered locally on the skin, BzATP may be a candidate chemotherapeutic growth-preventive drug with high therapeutic and low toxic pharmacological profile. Other epithelia could be considered as potential targets for local treatment with BzATP as well, including the oral mucosa, the vulvar and vaginal epithelia, and the ectocervix. These squamous stratified epithelia are phenotypically similar to the skin; their reserve cells express the $P2X_7$ receptor, and activation of the receptor induces apoptosis. Cancers of these tissues usually develop from premalignant lesions, and similar to the skin the cancer risk can vary from 0.1% to 20% [134-136]. Although it is not necessary to understand the mechanism of an invention, it is believed that activation of $P2X_7$-dependent apoptosis with BzATP could be a novel chemotherapeutic growth-preventive modality for precancerous and early cancerous epithelial lesions.

In one embodiment, the present invention contemplates a method for treating and preventing cancer comprising activating a $P2X_7$ receptor. For example, the data presented herein show that $P2X_7$-mediated apoptosis controls the growth of skin epithelial cells. In particular, a local application of a $P2X_7$-specific agonist ligand (i.e., for example, BzATP) inhibits formation of DMBA/TPA-induced papillomas in mice in vivo. Although it is not necessary to understand the mechanism of an invention, it is believed that the observed inhibition may be mediated by a mechanism associated with activation of $P2X_7$-induced apoptosis.

The data presented herein also show that a $P2X_7$ receptor is both necessary and sufficient to mediate the BzATP pro-apoptotic effect. ATP concentrations in the high nanomolar range of conditioned media of both normal human keratinocytes and human SCC-9 cells support the suggests that a $P2X_7$ receptor mechanism may play a role in in vivo cell regulation of apoptosis and growth. Accordingly, ATP may be secreted by cells into the extracellular milieu, wherein the resultant steady-state ATP levels are sufficient to activate the $P2X_7$ receptor and induce apoptosis. Since steady-state extracellular levels of ATP are similar between normal keratinocytes and SCC-9 cells (infra), it is suspected that $P2X_7$-mediated apoptosis may depend primarily on the expression of the receptor. (Wang et al, 2004a; Feng et al, 2005). In other types of epithelial cells, a lower cellular expression of $P2X_7$ mRNA and receptor levels appear in cancer cells versus normal epithelial cells. This decreased expression was associated with a decreased $P2X_7$-mediated baseline apoptosis rate and/or ligand-induced apoptosis in cancer cells as compared to normal cells. (Wang et al, 2004a; Li et al, 2006; Li et al, 2007). These data may be biologically and clinically important because defective apoptosis could lead to cancer. Gasser and Raulet, 2006; Kujoth et al, 2006; Rodriguez-Nieto and Zhivotovsky, 2006. Further, decreased cellular expression of $P2X_7$ receptor could be causally related to the development of epithelial cancers.

In one embodiment, the present invention contemplates a method for modulating the growth of epidermal cells by controlling $P2X_7$-mediated apoptosis. In one embodiment, the epidermal cells comprise germinative epidermal cells. In one embodiment, the controlling comprises drugs which activate the $P2X_7$ receptor, wherein formation of a skin neoplasia is inhibited.

A. Anti-Cancer Agent Screening

Potential effective drugs may be screened by using a DMBA/TPA mouse skin chemical carcinogenesis model system that is capable of inducing skin squamous cell carcinoma within 20 weeks of treatment. In the course of cancer development, skin papillomas usually arise first (i.e., within 6-15 weeks after initial DMBA/TPA exposure. Glick et al, 2007. The data discussed below using this model showed for the first time that pharmacological stimulation of the $P2X_7$ receptor can inhibit development of epidermal papillomas. Specifically, when DMBA/TPA-treated mice were co-treated with BzATP the incidence of papilloma formation was decreased.

In one embodiment, the mean number of papillomas per animal decreased by about 25%. In one embodiment, the mean papilloma size decreased by about 45%. In one embodiment, treated papillomas involuted more frequently. Although it is not necessary to understand the mechanism of an invention, it is believed that a pharmacological activation of the $P2X_7$ receptor in vivo can inhibit formation of DMBA/TPA-induced skin papillomas and stimulate involution of formed papillomas.

It is further believed that BzATP treatment effects do not induce any inflammatory skin changes that could potentially be related to $P2X_7$ actions. Dubyak and el-Moatassim, 1993; Ralevic and Burnstock, 1998. Also, BzATP treatment did not produce other gross or microscopic effects on the skin, and there were no abnormal changes that could be the result of excessive apoptosis such as thinning or ulcerations. It should be noted that Ki67 levels did not change during BzATP treatment, thereby supporting the conclusion that BaATP effects are primarily due to $P2X_7$ receptor mediated effects.

Until the present invention, the mechanism by which BzATP-augmented $P2X_7$-apoptosis inhibited DMBA/TPA-induced papilloma formation was unknown. While it is generally believed that carcinogens (e.g. DMBA/TPA) may stimulate uncontrolled growth of proliferating (germinative) cells, the underlying biochemical control of cell growth may be controlled by $P2X_7$-mediated apoptosis (infra). It is therefore possible that the growth and development of papillomas induced by DMBA/TPA was balanced by the apoptotic activity of BzATP-$P2X_7$. One possibility is that these two effects are independent of each other and that the development and rate of growth of papillomas depend on the contributions to regulation of cellular growth made by these two opposing stimuli. An alternative hypothesis, is that activation of the $P2X_7$ receptor inhibits DMBA/TPA cellular and molecular proliferative effects. The signaling pathway and molecular mechanism by which activation of the $P2X_7$ receptor induces apoptosis in keratinocytes has not been clearly characterized.

In one embodiment, the present invention contemplates a method for treating cancer comprising at least a partial inhibition of papilloma formation. In one embodiment, the inhibition is a result of treatment with a $P2X_7$ receptor agonist. In one embodiment, the $P2X_7$ agonist comprises BzATP. In one embodiment, the agonist is provided as a local application. In one embodiment, the local application comprises a concentration of approximately 1 µg/cm$^2$ BzATP. Although it is not necessary to understand the mechanism of an invention, it is believed that these inhibitory effects are dose-related such that higher doses have a greater effect in inhibiting papilloma formation.

In the DMBA/TPA mouse model, most early papillomas are histologically benign, but some progress to a squamous cell carcinoma stage. Glick et al, 2007. The potential for malignant conversion in this model is largely cell autonomous, independent of microenvironmental influences. Woodworth et al, 2004. Papillomas at risk for developing into cancer are usually characterized by increased proliferation of keratinocytes in the basal and suprabasal layers. Glick et al, 2007. This characteristic is relevant because (a) the $P2X_7$ receptor is expressed in basal/parabasal layers of normal stratifying epithelia (Li et al, 2006) including the epidermis (Greig et al, 2003a; and the data presented herein); (b) decreased expression of the $P2X_7$ receptor in basal/parabasal layers can be identified already in premalignant lesions of stratifying epithelia (Li et al, 2006); (c) treatment with BzATP induced activation of the $P2X_7$ receptor in basal/parabasal layers (data presented herein); and (d) BzATP treatment stimulated apoptosis also in basal/parabasal layers of keratinocytes outgrowths at the base of already developed papillomas. See, FIG. 5B(d). Therefore, BzATP may have both preventive and therapeutic effects on the growth of papillomas.

In one embodiment, the present invention contemplates a method for treating human epithelial cancers. In one embodiment, a $P2X_7$ receptor is expressed by most types of epithelial cells. Surprenant et al, 1996; Ralevic and Burnstock, 1998; Khakh et al, 2001; Wang et al, 2004b; Feng et al, 2006; Li et al, 2006; Li et al, 2007. It is believed that epithelial cancers usually develop from premalignant lesions, and decreased expression of the $P2X_7$ receptor occurs already in early premalignant lesions. Li et al, 2006; Li et al, 2007. Cancer risks of premalignant lesions of stratifying epithelia, e.g. the oral mucosa (leukoplakia), cervix (dysplasia) and the epidermis (actinic keratosis) may vary form 0.1% to 20%, but at present it is difficult to predict which lesions will progress into cancer. Reibel, 2003; Fu and Cockerell, 2003; Lindeque, 2005.

In one embodiment, the present invention contemplates a composition comprising at least one compound capable of activating a $P2X_7$ receptor, wherein the growth and progression of epithelial lesions are inhibited in individuals at risk. In one embodiment, the compound comprises BzATP. The data described herein show that BzATP can be absorbed through the skin and may specifically target cells in the germinative layers of the epithelium at the site of drug application. Although it is not necessary to understand the mechanism of an invention, it is believed that pharmacological activation of the $P2X_7$ receptor may control the growth and progression of premalignant lesions through apoptosis without evoking necrosis and an inflammatory or immune response.

B. Intracellular $P2X_7$ Expression

In one embodiment, the present invention contemplates a method for treating cancer comprising increasing $P2X_7$ receptor gene expression. Although it is not necessary to understand the mechanism of an invention, it is believed that the reduced pro-apoptotic effect of BzATP in mouse cancer keratinocytes is possibly the result of low expression of the $P2X_7$ receptor.

1. Normal Cells

Figure 1:
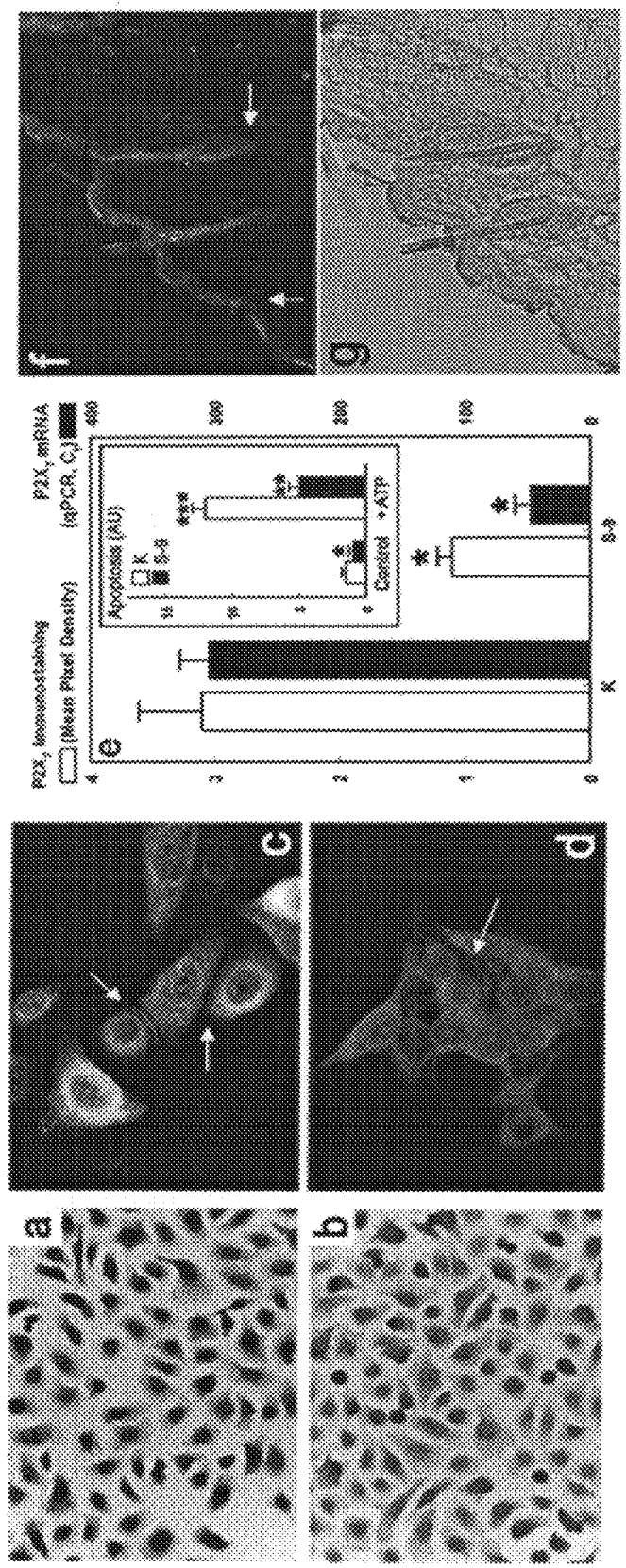
FIG. 1 presents exemplary data showing $P2X_7$ expression in epidermal cells. Panels a-d are representative of 2-6 repeats.

The data presented herein confirmed that $P2X_7$ receptor is expressed in epidermal cells. In situ hybridization assays in cultured human normal keratinocytes detected binding of an anti-sense full length $P2X_7$ cDNA probe in perinuclear/cytoplasmic regions, with no reaction to the sense $P2X_7$ cDNA probe. See, FIG. 1A and FIG. 1B, respectively. Similarly, in cultured human normal keratinocytes, $P2X_7$ immunoreactivity was found in the cytoplasm and in the plasma membrane. See, FIG. 1C.

2. Human Epidermal Squamous Cell Carcinoma-9 Cells

Previous studies in uterine epithelia showed that $P2X_7$ mRNA and $P2X_7$ receptor levels are lower in cancer cells as compared to corresponding normal epithelial cells. Li et al, 2006; Li et al, 2007. The data presented herein show similar trends in epidermal cells. See, FIGS. 1C and 1D. $P2X_7$ immunoreactivity was 3 fold lower in SCC-9 cells than in normal keratinocytes. See, FIGS. 1C and 1D. Likewise, $P2X_7$ mRNA levels were 6 fold lower in SCC-9 cells than in normal keratinocytes. See, FIG. 1E. The decreased $P2X_7$ receptor expression correlated with decreased apoptosis in these cells. For example, both baseline apoptosis and ATP-induced apoptosis were lower in SCC-9 cells than in normal keratinocytes. See, FIG. 1E, insert.

3. Mouse Skin Cancer Cells

Cellular effects of BzATP are believed to be mediated by the $P2X_7$ receptor. Dubyak et al., "Signal transduction via P2-purinergic receptors for extracellular ATP and other nucleotides" *Am J Physiol* 1993, 265:C577-C606; and Ralevic et al., "Receptors for purines and pyrimidines" *Pharmacol Rev* 1998, 50:413-492.

The data presented herein show that normal cells, papilloma cells, and cancer skin cells in the mouse express the $P2X_7$ receptor, but cancer skin cell levels were significantly lower than either normal skin cells or papilloma cells. See, FIG. 12. Immunostaining with the anti-$P2X_7$ receptor antibody of tissue cross sections containing normal skin revealed intense immunoreactivity that localized predominantly in the epidermis within proliferating keratinocytes and epidermal hair shafts. See, FIGS. 12A and 12B.

In papillomas, $P2X_7$ immunoreactivity was intense, similar to normal tissues, and it localized predominantly within proliferating keratinocytes at the base of the developing papillomas. See, FIGS. 12C and 12D, respectively. In contrast, $P2X_7$ immunoreactivity in cancer tissues was significantly lower than in normal epidermal or papilloma tissues. See, FIGS. 12E and 12F, respectively. However, $P2X_7$ immunoreactivity was four-fold less in cancer than in normal tissues. See, FIG. 12G.

This immunostaining data were confirmed by Western blot experiments. Quantitative assay of a $P2X_7$-specific band (i.e., for example, 75 KDa) revealed a five-fold lower density in cancer tissues than in normal tissues. See, FIG. 12H. Further confirmation was obtained by $P2X_7$ mRNA experiments where quantitative polymerase chain reaction (qPCR) assays revealed a five-fold lower $P2X_7$ mRNA/GAPDH mRNA ratio in normal tissues than in cancer tissues. See, FIG. 12I. Collectively, these data indicate that $P2X_7$ receptor expression levels in mouse skin cancer tissues are four-five fold lower than in mouse normal skin tissues.

The effects of BzATP on $P2X_7$ expression and apoptosis (determined by TUNEL) in was determined in art accepted tissue models for papilloma and cancer tissues. In these studies, $P2X_7$ immunoreactivities in cross sections of DMBA/TPA-induced papillomas did not differ from normal cells in either baseline intensity or after BzATP treatment. See, FIG. 15A and FIG. 15B. In contrast, however, the baseline intensity of $P2X_7$ immunoreactivity in cross sections of skin cancers was significantly lower than in normal and in papilloma tissues. See, FIG. 12A and FIGS. 15A & 15B, respectively. However, as with the papillomas, treatment with BzATP did not effect $P2X_7$ receptor expression in cancer cells. See, FIGS. 15E and 15F, respectively.

TUNEL staining was weak in cross sections of papillomas and cancer tissues from the DMBA/TPA group. See, FIGS. 15C and 15G, respectively. Similar findings were observed in cross sections of normal skin. See, FIGS. 13F and 14G. In contrast, TUNEL staining was more intense in cross sections of papillomas and cancer tissues from the DMBA/TPA+BzATP group. See, FIG. 15D and FIG. 15H. In papillomas obtained from mice of the DMBA/TPA+BzATP group, enhanced TUNEL staining decorated basal/parabasal layers of keratinocytes outgrowing at the base of the developing papilloma. See, FIG. 15D. These data suggest that although BzATP does not effect $P2X_7$ receptor expression, $P2X_7$-mediated apoptosis is, nevertheless, increased.

Morphologically, BzATP delayed formation of DMBA/TPA-induced papillomas, and resulted in fewer and smaller papillomas. Although it is not necessary to understand the mechanism of an invention, it is believed that some papillomas may have spontaneously regressed and involuted. Glick et al., "The high-risk benign tumor: evidence from the two stage skin cancer model and relevance for human cancer" *Mol Carcinogenesis* 2007, 46:605-610.

However, the majority (i.e., for example, about two thirds) of papillomas either progressed into squamous spindle-cell carcinomas or persisted as non-cancerous lesions. Persistence as non-cancerous lesions was increased after BzATP treatment. For example, in mice co-treated with BzATP the proportion of animals with cancers at week 14 was lower than in the DMBA/TPA+BzATP group (50% versus 80%) and remained relatively stable. In contrast, the proportion of animals with cancers increased steadily in the DMBA/TPA group, reaching 100% at week 24. These data suggest that local treatment with BzATP inhibits formation of DMBA/TPA-induced skin papilloma, and it can also inhibit papilloma cell transformation into cancer cells.

BzATP had little effect on the number of cancerous lesions per animal at weeks 14-28, and on the proportion of animals with cancerous lesions >10 mm$^3$ at weeks 14-22. In contrast, after week 23 the proportion of living animals with cancerous lesions >10 mm$^3$ increased in the DMBA/TPA group while it had decreased in the DMBA/TPA+BzATP group. These data suggest that local treatment with BzATP exerts an inhibitory effect on the development on skin neoplasia.

Interestingly, at weeks 15-24, among animals with cancerous lesions, the proportion of living animals with lesions larger than 200 mm$^3$ tended to be higher in the DMBA/TPA+BzATP group than in the DMBA/TPA group. This effect cannot be explained by augmented proliferation since BzATP did not stimulate DNA synthesis in cultured normal keratinocytes. Instead, the effect could be explained by comparing the survival curves (See, FIG. 11B) and the proportions of animals with smaller and larger size cancerous lesions. See, FIGS. 10B & 10C. Thus, cancer-related deaths in the DMBA/TPA group were associated more often with smaller lesions while cancer-related deaths in the DMBA/TPA+BzATP group were associated with relatively larger lesions. This suggests that treatment with BzATP also prolonged the life of animals with developed cancers.

B. P2X$_7$-Mediated Cell Apoptosis

In one embodiment, the present invention contemplates a method for treating cancer comprising inducing P2X$_7$-mediated cellular apoptosis. Although it is not necessary to understand the mechanism of an invention, it is believed that P2X$_7$-dependent apoptosis plays a role in controlling the development and progression of cancers including, but not limited to, epidermal neoplasias.

It was previously suggested that the P2X$_7$ mechanism controls growth of epithelial cells through activation and modulation of apoptosis, Wang et al, 2004a. To better understand the cellular effects of BzATP in vivo, experiments investigated the effects of BzATP in the normal mouse on skin morphology and histology, immunoreactivities of P2X$_7$ antibody, and apoptosis.

1. In Vitro Effects of Exogenous BzATP

First, the apoptosis dose-requirements of ATP and of the P2X$_7$-specific agonist BzATP were determined. Treatment of keratinocytes and SCC-9 cells with ATP, or with the P2X$_7$-specific agonist BzATP, augmented apoptosis in a dose-related manner. See, FIG. 2A. It can be observed that ATP was effective at inducing apoptosis at a 100 nM concentration. The data also showed that the combined pro-apoptotic effects of BzATP (100 µM) with ATP, at either 1 µM or 250 µM were non-additive. In contrast, induction of apoptosis with TNFα in combination with BzATP was additive. See, FIG. 2A, Insert a). These data suggest that ATP, but not TNFα, induce apoptosis via the same mechanism of BzATP, i.e. the P2X$_7$ receptor mechanism. Intracellular ATP levels were observed to be 610±50 nM and 460±250 nM, respectively. These data indicate that ATP is maintained within a concentration range sufficient to activate P2X$_7$-mediated apoptosis. See, FIG. 2A, Insert b.

It has been suggested that keratinocytes express different types of purinergic receptors and that it might be possible that, in addition to the P2X$_7$ receptor, ATP-related apoptosis was mediated by other types of purinergic receptors. Burnstock, 2006. The above data does not support this speculation. First, the ATP concentration threshold for inducing apoptosis is consistent with a P2X$_7$-mediated effect. Dubyak and el-Moatassim, 1993; and Ralevic and Burnstock, 1998. Second, the combined pro-apoptotic effects of a low (1 µM) or a high concentration of ATP (250 µM) with a high concentration of BzATP (100 µM) did not produce additive responses, suggesting that ATP and BzATP act via a common mechanism (presumably the P2X$_7$ receptor). In contrast, the combined pro-apoptotic effects of BzATP and TNFα did produce an additive response, suggesting that BzATP and TNFα act via different mechanisms (i.e., for example, the P2X$_7$ receptor versus the TNFα-TRAIL pathway, respectively). Aggarwal and Rath, 1999. Third, the present data ruled out the possibility that the ATP/BzATP pro-apoptotic response was non-additive due to limited capacity of the cells to undergo apoptosis, because the pro-apoptotic effect of BzATP plus TNFα was greater than the BzATP only effect.

2. In Vitro Recombinant P2X$_7$ Expression

MDCK cells heterologously expressing the human full-length P2X$_7$ receptor tagged with N-Myc at the N-terminus (N-Myc-hP2X$_7$-MDCK) have been used to study the P2X$_7$ receptor pathway. MDCK are epithelial cells that lack endogenous expression of the P2X$_7$ receptor. Feng et al, 2006; and Li et al, 2006.

Laser-confocal microscopy of N-Myc-hP2X$_7$-MDCK cells showed P2X$_7$-immunoreactivity decorating the plasma membrane. See, FIG. 2B, Insert: Panels a and b. Western blots of N-Myc-hP2X$_7$-MDCK cells lysates revealed co-immunoreactivity of a 75 kDa form with anti-Myc and anti-P2X$_7$ antibodies. See, FIG. 2B, Insert: Panels c-e. These data are consistent with earlier reports suggesting expression of a functional P2X$_7$ receptor. Feng et al, 2006. Confirmation of such expression was determined by treatment of N-Myc-hP2X$_7$-MDCK cells with anti-sense P2X$_7$ oligonucleotides that inhibited expression of the 75 kDa P2X$_7$ receptor. Treatment with random-control P2X$_7$ oligonucleotides had no such effect. See, FIG. 2B, Insert: Panels c and d).

To test the effect of heterologous expression of the human full-length P2X$_7$ receptor in MDCK cells on baseline and agonist-induced apoptosis, N-Myc-hP2X$_7$-MDCK cells were treated with BzATP. Wild-type (WT) MDCK cells, which lack endogenous expression of P2X$_7$, were used as a control cell line. Feng et al, 2006. In WT-MDCK cells, treatment with BzATP did not induce apoptosis. See, FIG. 2B. In contrast, baseline apoptosis of N-Myc-hP2X$_7$-MDCK cells was 1.5-fold greater than of WT-MDCK cells and treatment with BzATP augmented the apoptosis 2.5-fold. See, FIG. 2C; Wang et al, 2004a. Treatments of WT-MDCK cells with anti-sense P2X$_7$ oligonucleotides or with random-control P2X$_7$ oligonucleotides had no effects on apoptosis. See, FIG. 2B. In contrast, treatment of N-Myc-hP2X$_7$-MDCK cells with anti-sense P2X$_7$ oligonucleotides, but not with random-control P2X$_7$ oligonucleotides, inhibited both the baseline apoptosis and the BzATP-augmented apoptosis. See, FIG. 2C. These data indicate that the P2X$_7$ receptor is both sufficient and necessary to mediate BzATP-dependent apoptosis.

3. In Vivo BzATP Effects on Normal Tissues

P2X$_7$ immunoreactivity in the mouse skin, that is morphologically and biochemically similar to human skin, was found predominantly in the germinative basal/parabasal epidermal cells and in the germinative basal cells of the hair shafts and hair roots. See, FIGS. 1F and 1G. Moreover, $P2X_7$ receptor expression levels in normal epidermal cells, cultured cells, and in in vivo mouse skin were similar to those reported in other types of normal human epithelia. See, FIGS. 1C and 1F; Li et al, 2006; and Li et al, 2007. Also, in human uterine epithelia the growth of epithelial cells has been reported to be controlled by $P2X_7$-mediated apoptosis. Wang et al, 2004a; Li et al, 2006; and Li et al, 2007.

a. In Vivo Tolerability and Short-Term Effects of BzATP

BzATP (100 μM in 200 μl [20 nmol, 14.3 μg, 1.0 μg/cm$^2$]), was applied twice weekly for 4 weeks on the posterior region of the shaved dorsal skin. The concentration/dose of BzATP and frequency of treatments were chosen based on the above discussed cell culture data. Each animal served as its own control by having vehicle-containing solution applied twice weekly for 4 weeks on the anterior region of the shaved dorsal skin.

Animals tolerated the treatments uneventfully, and there were no noticeable changes in physical characteristics, animals' behavior, feeding habits or in animals' weights (not shown). Treatments with BzATP or the vehicle solution also had no visible effect on the dorsal skin. See, FIG. 13A. Histological H&E evaluation showed no differences in cross sections obtained from the posterior (BzATP) or anterior (Control) skin dorsal areas. See, FIGS. 13B and 13C. In cross sections of the posterior (BzATP-treated) region of the dorsal skin, there was an increased number of epidermal basal/parabasal $P2X_7$-positive cells with nuclei at different stages condensation, fragmentation and pyknosis. See, FIG. 3D, arrows. These data suggested that treatment with BzATP augmented apoptosis of epidermal cells.

Also studied were the effects of local treatment with BzATP on skin apoptosis in vivo by TUNEL staining. The negative control experiment showed minimal auto-fluorescence in cross sections of the mouse skin. See, FIGS. 13D and 13E. In skin cross sections of non-treated mice, only faint TUNEL staining decorated the epidermis. See, FIG. 13F. In contrast, in skin cross sections of BzATP-treated mice, numerous epidermal basal/parabasal cells and epidermal hair shaft cells stained TUNEL positive. See, FIG. 13G. Additionally, DAPI stains of cross sections of BzATP-treated skin revealed greater proportion of nuclei at advanced stages of condensation, fragmentation and pyknosis as compared to controls. See, FIG. 13I and FIG. 13H, respectively.

b. In Vivo Long-Term Effects of BzATP

BzATP was applied locally twice a week on the surface of the shaved dorsal skin for a total of 16 weeks. The control group included mice that had their back shaved and were treated only with the vehicle. Long-term BzATP treatment had no noticeable effect on animals' gross appearance of the treated skin. See, FIGS. 14A & 14C versus FIGS. 14B & 14D, respectively. Further, no effects were observed on behavior, feeding habits, or body weights (data not shown). Mean serum levels of ALT (SGPT) and AST (SGOT) were similar among the four groups, and were in the normal range for the mouse (not shown).

Histological evaluation of cross sections of dorsal skin showed no differences in specimens obtained from animals in the control and BzATP groups. See, FIGS. 3G and 3H, and FIGS. 14E and 14F. Also, there were no significant differences in Ki67 immunoreactivity in cross sections obtained from the control and BzATP groups. See, FIGS. 3I and 3J. In contrast, in the BzATP group TUNEL staining was significantly enhanced in epidermal and in hair shaft keratinocytes as compared to the control group, and TUNEL staining co-localized with $P2X_7$ immunoreactivity. See, FIGS. 3K-3X.

In the epidermis of BzATP-treated mice, the TUNEL staining was found mainly in basal/parabasal layers. See, FIGS. 3L and 3R, horizontal arrows; FIGS. 3V and 3X, and FIGS. 14G and 14H. Furthermore, enhanced TUNEL staining co-localization with $P2X_7$ immunoreactivity was primarily confined to the basal/parabasal layers. See, FIGS. 3T-3X, FIGS. 14I and 14J (low magnification) and FIGS. 14K and 14L. (high magnification). Image analysis of TUNEL staining in the epidermis in cross sections from the BzATP group revealed mean pixel density (±SD) of 5.2±0.3 versus 0.8±0.2 in epidermal cross sections from the control group (p<0.01, n=3).

In the skin of BzATP-treated mice, TUNEL staining was also significantly enhanced in hair shaft keratinocytes compared to the control group. See, FIGS. 3L and 3R, vertical arrows; and FIGS. 3V and 3X. TUNEL staining also was co-localized with $P2X_7$ immunoreactivity. See, FIGS. 3T-3X. Image analysis of TUNEL pixel density in hair-shaft cross sections from the BzATP group was 6.1±0.8 versus 1.1±0.3 in hair-shaft cross sections from the control group (p<0.01, n=3).

Collectively, these data indicate that treatment with BzATP up-regulated apoptosis in proliferating epidermal and hair shaft keratinocytes. However, in the normal mouse skin, the BzATP treatment and the augmented apoptosis did not affect morphology or histology of the skin.

4. In Vivo BzATP on Cancerous Tissue Development

Experiments were performed to test the hypothesis that activation of the $P2X_7$ receptor could inhibit development of epidermal neoplasia. These experiments utilized the mouse two-step DMBA/TPA skin neoplasia model, which involves tumor initiation by local treatment with DMBA, followed by tumor promotion by local treatment with TPA. Agarwal et al, 2005; and Guo et al, 2006. Mice had their dorsal skin shaved, and DMBA was applied once by topical application onto the shaved dorsal skin. TPA treatment by topical application onto the shaved dorsal skin was started one week later and continued twice a week for 12 weeks.

Epithelial cancers usually develop from a premalignant lesions, e.g., a papilloma, and the cancer risk of premalignant epithelial lesions may vary from 0.1% to 20%. 48. Reibel J, "Prognosis of oral pre-malignant lesions: Significance of clinical, histopathological, and molecular biological characteristics" *Crit Rev Oral Biol Med* 2003, 14:47-62; Fu et al., "The actinic (solar) keratosis: A 21st century perspective" *Arch Dermatol* 2003, 139:66-70; and Lindeque B G, "Management of cervical premalignant lesions" *Best Pract Res Clin Obstet Gynaecol* 2005, 19:545-561.

Animals were divided into three groups: Control mice (n=15) that had their back shaved and were treated only with the vehicle; DMBA/TPA-treated mice (n=15); and DMBA/TPA-treated mice that were co-treated with BzATP twice a week from week-2 (i.e. two weeks prior to DMBA) (n=14). All treatments were applied locally on the shaved dorsal skin. Papilloma development was monitored weekly from week 5 to 12 after the DMBA. Endpoints were percent animals with at least one papilloma; number of papilloma per animal; and mean papilloma size (mm [largest lesion dimension]). None of the animals in the control group had developed papillomas, and they will not be further discussed.

Fourteen (14) out of the fifteen (15) animals in the DMBA/TPA group (93%) and twelve (12) out of the fourteen (14) (78%) animals in the DMBA/TPA+BzATP group developed at least one skin papilloma at week 12. See, FIG. 5A. Using time-to-event data (i.e., for example, a Kaplan-Meier analysis for "papilloma-free" states) the log-rank test between the DMBA/TPA and DMBA/TPA+BzATP groups was not significant (p=0.273). However, analysis of the proportion having a papilloma at weeks 5-12 separately gave a borderline (p=0.055) result at week 6 of treatment. Specifically there were 13/15 (86.7%) in the DMBA/TPA group versus 7/13 (53.8%) in the DMBA/TPA+BzATP group having at least one papilloma.

In the DMBA/TPA and DMBA/TPA+BzATP groups the mean number of papillomas per animal increased over the 12 week study period, but the increase in papillomas in the DMBA/TPA+BzATP group was smaller than in the DMBA/TPA group. See, FIG. 5B. An independent samples t-test for weeks 5-12 for the DMBA/TPA and DMBA/TPA+BzATP groups revealed borderline significant difference at weeks 8 and 9 (p=0.051, 0.057) and a significant difference at week 10 (2.3±0.34 and 1.23±0.34 papillomas per animal [mean±SEM], respectively, p=0.033). Repeated measures analysis of variance (ANOVA) yielded a significant time effect ($p<0.01$), a borderline group effect (p=0.067) and a non-significant time*group interaction effect (p=0.290), for the DMBA/TPA and DMBA/TPA+BzATP curves. The latter indicates parallel non-interacting trends for the DMBA/TPA and DMBA/TPA+BzATP curves.

In the DMBA/TPA and DMBA/TPA+BzATP groups, the mean papilloma size per animal increased over the 12 weeks study period, but the increase in the DMBA/TPA+BzATP group was smaller than in the DMBA/TPA group. See, FIG. 5C. An independent samples t-test for weeks 5-12 for the DMBA/TPA and DMBA/TPA+BzATP groups revealed significant differences at all weeks for the mean size (with respective p values ranging from 0.005 to 0.029). Thus, for example, at week 12 mean papilloma size (mm) per animal was 5.86±0.91 versus 3.46 ±0.73 (mean±SEM), respectively (p=0.01). Likewise, repeated measures ANOVA yielded a significant time effect ($p<0.01$), a significant group effect (p=0.011) and a non-significant time*group interaction effect (p=0.113), for the DMBA/TPA and DMBA/TPA+BzATP curves. The latter indicates, again, parallel non-interacting trends for the DMBA/TPA and DMBA/TPA+BzATP curves.

Interestingly, papillomas induced by DMBA/TPA treatment in mice co-treated with BzATP were less hypertrophic and displayed less frequently ulceration and necrosis. See, FIG. 5A(c). Also, in these mice the formed papillomas frequently showed various degrees of involution. See, FIG. 5A(c), arrows.

Collectively, these data show that in DMBA/TPA-treated mice, co-treatment with BzATP applied locally on the skin tended to decrease the incidence of papilloma formation; it decreased the mean number of papillomas per animal by about 25% and the mean papilloma size by about 45%. In addition, in mice co-treated with BzATP, formed papillomas underwent more frequently involution.

Large papillomas (i.e., for example, greater than 5 mm in diameter) were biopsied at week 10 from one animal of each of the two treatment groups. These tissues were assayed for microscopic H&E evaluation, Ki67 immunostaining, and TUNEL. There were no differences among the two groups in tissue architecture or histology or Ki67 immunoreactivity. See, FIG. 5B(a,b); and not shown, respectively. Papilloma tissues from animals in the DMBA/TPA group showed weak TUNEL staining. See, FIG. 5B(c). In contrast, papilloma tissues from animals in the DMBA/TPA+BzATP group showed intense TUNEL staining in basal/parabasal regions of the papilloma epithelial regions. See, FIG. 5B(d), arrow).

After twenty-eight (28) weeks, lesions induced by the local administration of DMBA/TPA progressed into formation of squamous spindle-cell carcinomas. See, FIGS. 6 and 7. As the data presented below show, about one-third of the papillomas involuted after week 14 and the remaining persisted either as non-cancerous papillomas, or transformed to cancerous lesions. All cancerous lesions arose from pre-existing papillomas, while none of the animals in the control group had developed skin lesions. See, FIG. 6A. There were no significant differences in the morphological or histological characteristics of the unaffected normal skin in the DMBA/TPA and the DMBA/TPA+BzATP groups. See, FIGS. 6A-I and FIGS. 7A-B, respectively. Similarly, there were no significant differences in the morphological and histological characteristics of papillomas in the DMBA/TPA and DMBA/TPA+BzATP groups. See, FIGS. 6B-E and FIGS. 7C-D, respectively.

After week 14, some papillomas remained intact while other started to involute in both the DMBA/TPA and DMBA/TPA+BzATP groups. See, FIGS. 6D-E, and FIG. 7E. However, in both groups most papillomas (i.e., for example, about two-thirds) underwent cancerous transformation to squamous cell carcinomas with spindle-cell changes. See, FIGS. 7F-I. There were no significant changes in the morphological and histological characteristics of cancers in the two groups. See, FIGS. 6F-I and not shown, respectively.

Overall, the data show that co-treatment with BzATP, applied locally on skin areas exposed to DMBA/TPA altered the incidence and pattern of skin lesions having progression to skin cancer. To evaluate the effects of BzATP, changes in skin lesions in the DMBA/TPA and DMBA/TPA+BzATP groups were compared relative to the length of treatment. Since formation of papillomas and cancerous lesions was time-related (i.e., for example, a marked cut-off occurs between weeks 13-14; see, FIG. 8A), data were analyzed separately for weeks 0-12 and weeks 14-28.

During weeks 0-12, the proportion of living animals with papillomas tended to be lower in the DMBA/TPA+BzATP group than in the DMBA/TPA group, and analysis of the proportion of living animals having a papilloma separately was significant at week 5 of treatment (($p<0.05$): 48±12% versus 80±10%, respectively). The proportion of living animals with any skin lesion between weeks 14-21 was similar in the two groups. Nonetheless, the proportion of living animals with any skin lesion differed significantly among the groups in weeks 22-28. See, FIG. 8A.

During the 28 week time period, the proportion of living animals with non-cancerous lesions (i.e., for example, existing and involuting papillomas) decreased in both groups. In contrast, the proportion of living animals with cancerous lesions in the DMBA/TPA group increased steadily, while in the DMBA/TPA+BzATP group the proportion of living animals with cancerous lesions decreased over time. For example, in week 28 the proportions of living animals with cancerous lesions in the DMBA/TPA and the DMBA/TPA+BzATP groups were 100% and 43±9%, respectively. See, FIG. 8B.

In both groups, the mean number of papillomas per living animal increased between weeks 0-12, but the increase in the DMBA/TPA+BzATP group tended to be smaller than in the DMBA/TPA group. See, FIG. 9A. An independent samples t-test revealed a significant difference at week 10 (i.e., for example, 2.3±0.5 and 1.2±0.4 papillomas per animal [mean±SD], respectively, p<0.04). Also, a repeated measures analysis of variance yielded a significant time effect for the DMBA/TPA and DMBA/TPA+BzATP curves between weeks 0-12 ($p<0.01$). See, FIG. 9A. Between weeks 14-28, the mean number of total lesions per living animal was not significantly different between the two groups. See, FIG. 9A. In both groups, the mean number of non-cancerous lesions decreased over the 14-28 weeks period. See, FIG. 9B. The mean number of cancerous lesions, however, remained the same. See, FIG. 9C.

Animals in both groups were compared relative to the total size of lesions (in mm$^3$) per animal. In both groups, the mean total papillomas size per living animal increased between weeks 0-12, but the increase in the DMBA/TPA+BzATP group was smaller than in the DMBA/TPA group. See, FIGS. 6B, 6C, and 10A. An independent samples t-test revealed significant differences at all weeks for mean total papillomas size (p<0.01-0.03). See, FIG. 10A. For example, in week 12 mean total papillomas size (in mm$^3$) per animal was 5.8±1.1 versus 3.4±1.0 (mean±SD), respectively (p<0.01). Likewise, a repeated measures analysis of variance yielded a significant time effect (p<0.01); a significant group effect (p<0.02); and a non-significant time*group interaction effect (p>0.1), for both DMBA/TPA and DMBA/TPA+BzATP data sets. The non-significant time*group interaction term, indicates non-interacting trends between the DMBA/TPA and DMBA/TPA+BzATP groups.

Between weeks 14-28, the variability of the lesion sizes among the two groups was large. Although it is not necessary to understand the mechanism of an invention, it is believed that this variability was due to an unproportional excessive growth of some lesions relative to others. See, FIGS. 6D-6I. This precluded a comparison of the means of lesion size among the two groups. However, since most non-cancerous lesions in both groups tended to be smaller than 10 mm$^3$ and the proportion of animals with non-cancerous lesions of >10 mm$^3$ was low in both groups (i.e., for example, <10%). See, FIG. 10B, triangles. Data representing the proportion of living animals with cancerous lesions >10 mm$^3$ were compared among the two groups. After week 28, a significantly smaller proportion of living animals was observed in the DMBA/TPA+BzATP group with cancerous lesions >10 mm$^3$ than in the DMBA/TPA group. For example, in week 28 the proportion of living animals with cancerous lesions >10 mm$^3$ were 81%±8% as compared to 16±4% in the DMBA/TPA and the DMBA/TPA+BzATP groups, respectively. See, FIG. 10B.

Five (5) mice in the DMBA/TPA+BzATP group survived despite having developed relatively large cancerous lesions, while maintaining normal weight and exhibiting normal behavior. See, FIG. 6I. In contrast, most mice in the DMBA/TPA group with smaller cancerous lesions met IACUC euthanization requirements due to poor general condition and excessive tumor burden. See, FIG. 6H. Analysis of the proportion of living animals with cancerous lesions >200 mm$^3$ showed a tendency for higher proportion of animals in the DMBA/TPA+BzATP group than in the DMBA/TPA group, but the differences did not reach statistical significance. See, FIG. 10C.

Using time-to-event data analysis it was found that development of cancerous lesions was significantly slower and lower in the DMBA/TPA+BzATP group than in the DMBA/TPA group. See, FIG. 11A. Survival curves for the DMBA/TPA and DMBA/TPA+BzATP groups were generated based on event (i.e., for example, death from cancer) and time-to-event (in weeks) for each group. A log-rank test was used to compare the survival curves based on group. The overall survival rates among the two groups did not differ statistically, although there was a tendency for earlier death in the DMBA/TPA group as compared to the DMBA/TPA+BzATP group. See, FIG. 11B.

5. Mechanism of BzATP-Augmented Apoptosis a. P2X$_7$ Receptor Expression

To better understand the mechanism of BzATP pro-apoptotic skin effects, experiments utilized cultured primary mouse keratinocytes that were obtained from wild-type mice, and from the P2X$_7$-receptor-deficient P2X$_7$$^{-/-}$Pfizer (PO mice and P2X$_7$$^{-/-}$GSK mice.

In wild-type mouse keratinocytes, BzATP augmented apoptosis in a dose-related manner. Effects began at BzATP levels as low as 50 nM, reaching maximal effect at 100-250 μM with an estimated BzATP EC$_{50}$ of about 10 μM. See, FIG. 16A. Pre-treatment with P2X$_7$-receptor anti-sense oligonucleotide decreased expression of the P2X$_7$-receptor. See, FIG. 16B, insert. The P2X$_7$-receptor antisense oligonucleotide also inhibited baseline apoptosis and blocked the pro-apoptotic effect of BzATP. See, FIG. 16B. Although it is not necessary to understand the mechanism of an invention, it is believed that the pro-apoptotic effect is likely induced paracrinologically by ATP secreted by the cells. Pre-treatment with random-control oligonucleotides had no effect on P2X$_7$-receptor expression. See, FIG. 16B, insert. Baseline apoptosis or apoptosis induced by BzATP was also unaffected by random-control oligonucleotides. See, FIG. 16B.

The dependence of the pro-apoptotic effect of BzATP on the expression of the P2X$_7$ receptor was further demonstrated in experiments using keratinocytes obtained from P2X$_7$-receptor-deficient mice. Compared to wild-type mouse keratinocytes, in both the P2X$_7$$^{-/-}$Pf and P2X$_7$$^{-/-}$GSK keratinocytes, treatment with 100 μM BzATP failed to induce apoptosis. See, FIG. 16C.

b. Calcium Pore Formation

In one embodiment, the present invention contemplates a method for treating cancer comprising activation of a P2X$_7$-mediated calcium pore (i.e., for example, a calcium channel). Although it is not necessary to understand the mechanism of an invention, it is believed that P2X$_7$-dependent apoptosis may be mediated by calcium influx via P2X$_7$-controlled pores, and involves the mitochondrial caspase-9 pathway.

In uterine epithelial cells, as well as in other types of cells, P2X$_7$-receptor-dependent apoptosis involves agonist-induced acute calcium influx via P2X$_7$ pores. To understand whether BzATP-induced apoptosis in mouse keratinocytes involves formation of P2X$_7$ pores, experiments compared activation by BzATP of the P2X$_7$ receptor by measuring cytosolic calcium levels and the formation of P2X$_7$ pores by measuring ethidium bromide influx. Feng et al., "A truncated P2X$_7$ receptor variant (P2X7-j) endogenously expressed in cervical cancer cells antagonizes the full-length P2X$_7$ receptor through hetero-oligomerization" *J Biol Chem* 2006, 281: 17228-17237.

In mouse wild-type keratinocytes, treatment with 100 μM BzATP in a 1.2 mM Ca$^{2+}$ solution, induced an acute increase in cytosolic calcium, which lasted at least 6 minutes. Conversely, when 1.2 mM EGTA was added to the solution (i.e., a low calcium solution), BzATP induced a short term spike in cytosolic calcium that quickly returned to normal levels (i.e., the prolonged, sustained, increase in cytosolic calcium was abolished). See, FIG. 17A. Although it is not necessary to understand the mechanism of an invention, it is believed that the short-term spike increase in cytosolic calcium most likely represents calcium release from intracellular stores. It is further believed that the lack of prolonged increase in cytosolic calcium in cells bathed in a low calcium extracellular medium low indicates that the BzATP-induced prolonged increase in cytosolic calcium involves calcium influx.

Experiments using mouse wild-type keratinocytes also revealed that treatment with BzATP induced an acute increase in the influx of ethidium bromide with a time-course similar to the increase in cytosolic calcium. See, FIG. 17B. Comparing the profiles of cytosolic calcium and ethidium bromide demonstrated a similar dose-dependence for BzATP. See, FIG. 17C. Further, these profiles resemble the dose dependence of apoptosis on BzATP with threshold effects at 50-100 nM and pre-maximal responses at 100-250 μM. See, FIG. 16A.

c. Cytosolic Calcium And Influx

Similar to the effects of BzATP on apoptosis, pre-treatment with the $P2X_7$-receptor anti-sense oligonucleotide blocked the BzATP-induced increase in cytosolic calcium and the BzATP-induced increase in ethidium bromide. See, FIGS. 18A and 18B, respectively. Pre-treatment with the random-control oligonucleotides had no effect on the responses to BzATP.

d. Extracellular Calcium Dependence

In mouse wild-type keratinocytes, lowering extracellular calcium attenuated baseline apoptosis and blocked the BzATP-induced apoptosis in a dose-related manner. See, FIG. 19A. Although it is not necessary to understand the mechanism of an invention, it is believed that the BzATP-augmented apoptosis involves caspase-9 and caspase-3. For example, treatment of mouse wild-type keratinocytes with a caspase-9 inhibitor (i.e., for example, LEHD-FMK) blocked BzATP-induced apoptosis while a caspase-8 inhibitor (i.e., for example, IETD-FMK) did not have a significant effect. See, FIG. 19B. Positive controls including, but not limited to, a specific inhibitor of terminal caspase-3 (i.e., for example, DEVD-FMK) or a non-specific pan-caspase inhibitor (i.e., for example, zVAD-FMK) similarly blocked BzATP-induced apoptosis. See, FIG. 19B.

e. Effects on Cellular Proliferation

To determine if the development of the large cancerous lesions in some animals in the DMBA/TPA+BzATP group was the result of a pro-mitogenic effect of BzATP, rates of DNA synthesis (in terms of [$^3$H]-thymidine incorporation) in response to BzATP were measured in mouse wild-type normal keratinocytes. Pre-treatments with the $P2X_7$-receptor anti-sense $P2X_7$ oligonucleotides or the random-control oligonucleotides, and treatments with BzATP had no significant effect on [$^3$]-thymidine incorporation. See, FIG. 20.

The data showed that the main targets of BzATP in the normal skin are proliferating keratinocytes of the epidermal basal/parabasal layers and hair shafts. In these $P2X_7$-receptor expressing cells, BzATP augmented apoptosis without evoking inflammatory changes. Experiments in $P2X_7$-deficient normal keratinocytes and in normal keratinocytes treated with antisense $P2X_7$ oligonucleotides showed that the $P2X_7$ receptor is a necessary mediator of the pro-apoptotic effect of BzATP, suggesting that the effect of BzATP is mediated by augmentation of $P2X_7$-mediated apoptosis. Similar to normal skin, the main targets of BzATP in papilloma tissues were $P2X_7$-receptor expressing proliferating keratinocytes at the base of developing papillomas. This finding relates to the fact that in the mouse DMBA/TPA model, papillomas at risk for developing into cancer are characterized by rapidly proliferating keratinocytes in the basal and parabasal layers of the papilloma. Glick et al., "The high-risk benign tumor: evidence from the two stage skin cancer model and relevance for human cancer" *Mol Carcinogenesis* 2007, 46:605-610.

Since treatment with BzATP decreased the incidence of DMBA/TPA-induced papillomas and their transformation into cancer, it is likely that the cellular mechanism of BzATP action involved augmented apoptosis of proliferating papilloma keratinocytes bearing the potential of malignant transformation. One of the differences between BzATP effects in the normal skin and in papilloma tissues was the lack of macroscopic effects in the former, while inhibiting the development and growth of papillomas. Thus, treatment with BzATP for 16 weeks in normal mice increased apoptosis in proliferating keratinocytes but it did not produce a thinning or ulceration of the skin, as would be expected of a potent pro-apoptotic drug.

Similarly, there were no significant differences in the morphological and histological characteristics of unaffected normal skin between animals in the DMBA/TPA+BzATP group (BzATP treatment for 30 weeks) and the DMBA/TPA group. However, in the DMBA/TPA+BzATP group, enhanced apoptosis was associated with inhibition of papilloma development. The disparity between BzATP effects between normal and papilloma tissues could be related to differences in the growth rate of the respective keratinocytes. Normal skin cells are slow growing and their overall growth rate is apparently not affected by BzATP. In contrast, in the fast growing papilloma keratinocytes BzATP-induced apoptosis slows and inhibits growth. The data in normal mice also showed that local treatment with BzATP had no adverse systemic effects, suggesting a relatively safe profile for the drug when applied locally on the skin. These data indicate that BzATP is absorbed from the skin into the basal/parabasal epidermal regions and hair shafts. The data also suggest that the predominant effect of BzATP is induction of apoptosis at the site of application, targeting rapidly growing proliferating keratinocytes.

In contrast to papillomas, the expression level of $P2X_7$ receptors in DMBA/TPA-induced cancer cells was low, as was evident by three assays: in-situ immunoreactivity, Western blots, and qPCR. These findings are similar to those reported in non-melanoma skin cancer cells, uterine, bladder and breast epithelial cancers. Greig et al., "Expression of purinergic receptors in non-melanoma skin cancers and their functional roles in A431 cells" *J Invest Dermatol* 2003, 121: 315-327; Li et al., "The $P2X_7$ Receptor: A novel biomarker of uterine epithelial cancers" *Cancer Epidemiol Biomarkers Preven* 2006, 15:1-8; Li et al., "Decreased expression of $P2X_7$ in endometrial epithelial pre-cancerous and cancer cells" *Gynecol Oncology* 2007, 106:233-243; Zhou et al., "MicroRNAs miR-186 and miR-150 downregulate expression of the pro-apoptotic purinergic $P2X_7$ receptor by activation of instability sites at the 3'-untranslated region of the gene that decrease steady-state levels of the transcript" *J Biol Chem* 2008, 283:28274-28286; and Li et al., "$P2X_7$ receptor expression is decreased in epithelial cancer cells of ectodermal, urogenital sinus, and distal paramesonephric-duct origin" (submitted, 2009). These findings suggest that the rapid proliferation of cancer cells could be in part due to the low expression of the $P2X_7$ receptor and to attenuated $P2X_7$-mediated apoptosis. Treatment with BzATP augmented apoptosis even in cancer cells expressing low levels of the $P2X_7$ receptor, but the effect was smaller than in normal or papilloma cells.

Until recently, little was known about the relationship between $P2X_7$-receptor and cellular apoptosis. The data presented herein suggest that $P2X_7$-receptor induced apoptosis may depend on enhanced calcium influx via $P2X_7$ pores, and possibly mediated by the caspase-9-mitochondrial pathway.

The following experimental findings in the present study support this hypothesis:

(a) Treatment with BzATP induced formation of pores and enhanced calcium influx;

(b) the BzATP-induced apoptosis, pore formation and the augmented and prolonged calcium influx were critically dependent on the expression of the $P2X_7$ receptor;

(c) the BzATP-induced apoptosis, pore formation and the augmented calcium influx had similar dose-dependence on BzATP;

(d) the BzATP-induced pore formation and the augmented calcium influx began shortly (30-60 seconds) after adding BzATP. In contrast, the BzATP-induced apoptosis required hours of treatment with BzATP, commensurate with a gene-mediated effect;

(e) the BzATP-induced apoptosis depended on the presence of extracellular calcium at a physiological concentration of 1.2 mM, and on calcium influx; and (f) the BzATP-induced apoptosis could be blocked by co-treatment with inhibitors of caspase-9 and caspase-3, but not of caspase-8.

Since caspase-3 is a terminal step in the caspase cascade, a possible interpretation of the present results is that $P2X_7$-receptor-apoptosis is mediated by the caspase-9 (mitochondrial) pathway. Fawthrop et al.," Mechanisms of cell death" *Arch Toxicol* 1991, 65:437-444; and Soti et al., "Apoptosis, necrosis and cellular senescence: chaperone occupancy as a potential switch" *Aging Cell* 2003, 2:39-45. Collectively, the data presented herein suggest that BzATP-dependent activation of the $P2X_7$ receptor involves formation of pores in the plasma membrane, and that facilitated uncontrolled influx of $Ca^{2+}$ via the $P2X_7$ pores stimulates apoptosis by the mitochondrial-caspase-9 pathway. $P2X_7$ pores are believed to be formed of channels composed of pannexins and ectodomains of the $P2X_7$ molecule, whose formation is dependent upon a $P2X_7$ receptor/agonist interaction. Feng et al., "A truncated $P2X_7$ receptor variant ($P2X_{7-j}$) endogenously expressed in cervical cancer cells antagonizes the full-length $P2X_7$ receptor through hetero-oligomerization" *J Biol Chem* 2006, 281: 17228-17237; Locovei et al., "Pannexin1 is part of the pore forming unit of the $P2X_7R$ death complex" *FEBS Lett* 2007, 581:483-488; and Iglesias et al., "$P2X_7$ receptor-Pannexin1 complex: Pharmacology and signaling" *Am J Physiol Cell* 2008, 295:C752-C760.

Papilloma keratinocytes are shown herein to express the $P2X_7$ receptor; therefore, the high expression levels of the $P2X_7$ receptor in in vivo papilloma cells, and the significant apoptotic effects in response to BzATP, could explain the inhibitory effect of BzATP on papilloma development. In contrast, the lesser effect of BzATP in skin cancer cells could be explained by the low expression level of the $P2X_7$ receptor in the cancer cells. At present, little is known whether neoplastic transformation decreases $P2X_7$-receptor expression, or whether neoplastic transformation is triggered preferentially in cells already expressing low levels of $P2X_7$ receptor. The former possibility is supported by data in endometrial and bladder cells where low expression of the $P2X_7$ receptor was found already in pre-cancerous and early cancerous cells but not in hyperplastic benign cells. Li et al., "Decreased expression of P2X7 in endometrial epithelial pre-cancerous and cancer cells" *Gynecol Oncology* 2007, 106:233-243. Accordingly, the carcinogenic process could have reduced $P2X_7$ expression during early stages of cancer development. On the other hand, the possibility that the neoplastic transformation is triggered preferentially in cells expressing low levels of the receptor is supported by data in uterine cervical epithelia, wherein low expression of the $P2X_7$ receptor was found already in dysplastic cells. Li et al., "The $P2X_7$ Receptor: A novel biomarker of uterine epithelial cancers" *Cancer Epidemiol Biomarkers Preven* 2006 15:1-8. Since only a small fraction of cervical dysplasia cases progresses to cancer, it is possible that low expression of the $P2X_7$ receptor in the cervix precedes the neoplastic transformation. Walboomers et al., "Human papillomavirus is a necessary cause of invasive cervical cancer worldwide" *J Pathol* 1999, 189: 12-19: Raab et al., "Long-term outcome and relative risk in women with atypical squamous cells of undetermined significance" *Am J Clin Pathol* 1999, 112:57-62; and Song et al., "Risk factors for the progression or persistence of untreated mild dysplasia of the uterine cervix" *Int J Gynecol Cancer* 2006, 16:1608-1613. Accordingly, abrogation of $P2X_7$-mediated apoptosis could be responsible for the preservation of genetically aberrant cells that are susceptible to carcinogenic stimuli, favoring neoplastic transformation. Staibano et al., "Prognostic value of apoptotic index in cutaneous basal cell carcinomas of head and neck" *Oral Oncol* 1999, 35:541-547.

The present data showed only partial inhibition (i.e., for example, ~50%) of papilloma and cancer formation in BzATP-treated mice. A relatively low dose (i.e., 1 µg/cm$^2$ BzATP) was used in the in vitro experiments. Therefore, it would be expected that higher doses, and/or more frequent applications, could produce greater inhibition papillomas and cancers, both in size and frequency.

IV. $P2X_7$ Receptor Expression Regulation

In one embodiment, the present invention contemplates a method for upregulating $P2X_7$ receptor expression. Although it is not necessary to understand the mechanism of an invention, it is believed that such receptor expression upregulation increases the cell surface density of $P2X_7$ receptors.

In one embodiment, the present invention contemplates a method for treating and/or preventing cancer by increasing $P2X_7$ receptor cell surface density. In one embodiment, the cell surface comprises a cancer cell surface. In one embodiment, the cell surface comprises a papilloma cell surface. In one embodiment, the increased $P2X_7$ receptor cell density induces apoptosis.

A. Elucidation of the Active Promoter Region

To define the active promoter region and the Transcription Initiation Start Site (TpIS), a series of cDNA fragments were generated encompassing a 1.7 kb DNA segment at the 5' region of the human $P2X_7$ gene. Nucleotides were numbered relative to the subsequently elucidated TpIS (+1), which corresponds with nt 1683 of the human $P2X_7$ gene (GenBank Y12851). Initial experiments included cDNA fragments ranging from −1664/+32 to −53/+32 nt. See, FIG. 28 and FIG. 29A. The cDNA fragments were inserted into a luciferase vector, and the $P2X_7$-luciferase reporter was transfected into HEK293 cells which lack endogenous expression of the $P2X_7$. Significant promoter activity was found in fragments ranging from −1664/+32 to −158/+32 nt, while shorter fragments lacked significant promoter activity. A cDNA fragment of −1179/−380 nt lacked significant promoter activity, suggesting that there is little promoter activity upstream of nt −380. Since maximal promoter activity was found in experiments using the −158/+32 nt fragment, the data suggested location of the active promoter of the human P2X7 gene in the −158/+32 nt region. See, FIG. 29A.

The TpIS was elucidated using the modified 5' RACE method. By sequencing, two possible TpISs were found upstream of the subsequently defined TpIS: Adenine bases at +1 nt and −73 nt. See, FIG. 28. To differentiate between the two, the TpIS-corresponding regions were mutated as (−1) CATT to GTAA, and (−73) AGGG to TATA. Fragments carrying the mutated regions were inserted into the luciferase vector and transfected into HEK293 cells. The results showed 70% luciferase activity in the (−73)AGGG→TATA construct but only 30% luciferase activity in the (−1)CATT→GTAA construct. See, FIG. 29B.

Sequence analysis also suggested two TATA-like sequences located upstream of the subsequently defined TpIS: TTAAA at −32 nt, and TTATC at −102 nt. See, FIG. 28. Mutation analysis revealed 50% luciferase activity in the (−32)TTAAA→TCCAA construct and no change in luciferase activity in the (−102)TTATC→CCATC construct.

See, FIG. 29B. Collectively these data suggest a TpIS at site +1 nt and a TATA-like sequence TTAAA at site −32 nt.

B. Regions Distal to the TpIS Inhibit Transcription

Sequence analysis of the human P2X7 gene (GenBank Y12851) downstream of the active promoter revealed an unusually high concentration of cytosine-phosphodiester-guanosine (CpG) dinucleotides sites in the +26 to +573 nt region. This region of 547 nt contains 20 CpG sites, in contrast to the −158/+32 190 by active promoter region, which contains only 4 CpG sites. Changes in methylation of cytosines within CpG sites have been reported to modulate gene function. Chen et al., (2006) "Establishment and maintenance of DNA methylation patterns in mammals" *Curr Top Microbiol Immunol* 301:179-201. Consequently, changes in the methylation status of CpG sites in the region downstream of the active promoter might regulate $P2X_7$ transcription. See, FIG. 28.

A construct containing the fragment −158/+573 resulted in less transcription compared to the −158/+32 construct as measured using Fluc/Rluc. See, FIG. 29C (upper panel). The data was replicated by measuring Fluc/GPDH mRNA as an endpoint. See, FIG. 29C (lower panel). It can be seen that data between the two different methods are similar, thereby indicating that cis regulatory elements contained within the +33 to +573 nt region downstream of the active $P2X_7$ promoter may inhibit transcription.

C. Demethylation Increases $P2X_7$ Receptor Expression And Apoptosis

1. Aza-dC Increases $P2X_7$ mRNA Levels

To determine whether changes in DNA methylation modulate $P2X_7$ gene transcription, cultured cervical cells were treated with the de-methylation agent 5-aza-2'-deoxycytidine (Aza-dC), and effects on $P2X_7$ mRNA steady state levels were measured. For experiments, cells were treated with 1 µM Aza-dC, which in preliminary experiments exerted near maximal effects (not shown).

Baseline levels of $P2X_7$ mRNA steady state levels (relative to CK-18) were higher in the normal hEVEC than in the HeLa cancer cervical epithelial cells wherein treatment with Aza-dC increased $P2X_7$ mRNA both in hEVEC and in HeLa cells. See, FIG. 30A. The effect was time-dependent, and increases in $P2X_7$ mRNA were observed already 18-24 hours after treatment. In hEVEC cells, levels of $P2X_7$ mRNA continued to increase, while in HeLa cells $P2X_7$ mRNA levels leveled off after 24 hrs and began to decrease afterwards, but remained elevated as compared to baseline for at least 72 hours after the start of treatment.

2. Aza-dC Increases $P2X_7$ Protein Levels

Aza-dC effects on $P2X_7$ protein were determined in terms of changes in cellular immunoreactivity to the anti $P2X_7$ antibody. In non-treated hEVEC cells, staining with the anti $P2X_7$ receptor antibody revealed homogenous $P2X_7$ immunoreactivity. See FIG. 30B, insert. Furthermore, treatment with 1 µM Aza-dC for 48 hours increased the $P2X_7$ immunoreactivity significantly. A similar effect was seen in HeLa cells (data not shown). Image analysis of $P2X_7$ immunofluorescence density in Aza-dC-treated cells revealed a 2 fold increase after 48 hours of treatment in P2X7 immunoreactivity for both the hEVEC and HeLa cells. See, FIG. 30B.

3. Aza-dC Increases $P2X_7$-Mediated Apoptosis

Baseline apoptosis was 2 fold higher in hEVEC cells than in HeLa cells. Treatment with the $P2X_7$-receptor specific agonist BzATP increased apoptosis 2.5 fold in hEVEC cells but it had no significant effect in HeLa cells. Treatment with Aza-dC increased mildly baseline apoptosis in hEVEC cells, and significantly (2 fold) baseline apoptosis in HeLa cells. In hEVEC cells pretreated with Aza-dC, co-treatment with BzATP resulted in greater apoptosis than in cells treated only with BzATP, but the effect was mild. See, FIG. 30C.

In contrast, in Aza-dC-pretreated HeLa cells co-treatment with BzATP resulted in 2.5 fold greater apoptosis than in cells treated only with BzATP, and the degree of apoptosis was nearly that observed in hEVEC cells under similar conditions. See, FIG. 30C. Although it is not necessary to understand the mechanism of an invention, it is believed that Aza-dC sensitized normal and cancer cervical cells to the pro-apoptotic effect of BzATP, probably by upregulating the expression of $P2X_7$ mRNA and protein receptor levels.

To determine whether apoptosis per se can stimulate an increase in $P2X_7$ mRNA, hEVEC and HeLa cells were incubated in serum-free medium for 14 hours. Wang et al., (2005) "EGF facilitates epinephrine inhibition of $P2X_7$-receptor mediated pore formation and apoptosis: a novel signaling network" *Endocrinology* 146:164-174. The results (not shown) indicated that $P2X_7$ mRNA steady state levels in hEVEC and in HeLa cells were similar in serum-deprived and in serum-exposed cells.

D. $P2X_7$ Gene Methylation Status

Effects of changes in the methylation status on $P2X_7$ transcription were evaluated in HEK293 cells transfected with the luciferase $P2X_7$ −158/+32 and/or −158/+573 reporter constructs. Hypermethylation assays involved incubation of the test plasmids with the CpG-Methylase M.SssI prior to transfections, and de-methylation assays were done by treating transfected cells with Aza-dC.

Hypermethylation had no significant effects on luciferase mRNA levels in HEK293 cells transfected either with the luciferase $P2X_7$ −158/+32 or luciferase −158/+573 reporter constructs. See, FIG. 31. De-methylation, induced by treatment with Aza-dC also had no significant effect on luciferase mRNA levels in cells expressing the −158/+32 nt construct. In contrast, Aza-dC increased luciferase mRNA levels two fold in cells expressing the −158/+573 nt construct. See, FIG. 31.

Methylation status may not be a non-specific promoter regulator. For example, measuring effects of de-methylation and hypermethylation on CK-18 and GAPDH mRNA steady-state levels following treatment with Aza-dC had no significant effects on the steady-state levels (data not shown). Also, in HEK293 cells transfected with either the luciferase P2 $X_7$ −158/+32 or the −158/+573 reporters, de-methylation and hypermethylation assays did not affect significantly steady-state levels of GAPDH mRNA (data not shown).

Collectively, these data suggest that regions downstream of the active $P2X_7$ promoter may regulate transcription by modulating DNA methylation.

E. CpG Sites and $P2X_7$ Gene Methylation Status

1. Downstream CpG sites Inhibit $P2X_7$ Transcription

CpG sites in a 547 nt region downstream of an active $P2X_7$ promoter (nt −158/+32) were evaluated using cDNA fragments were inserted into a luciferase vector. For example, a $P2X_7$-luciferase reporter was transfected into HEK293 cells, and $P2X_7$ transcription was determined in terms of luciferase activity. See FIG. 32.

Luciferase activity in the fragment −158/+221 was low, about 10% compared to that of the active promoter alone (nt −158/+32). Luciferase activity in the fragment −158/+232 was higher, about 75% compared to the active promoter. Luciferase activities in fragments −158/+337 and −158/+402 were lower by 25% and 50%, respectively than in fragment −158/+232. Luciferase activity in fragments −158/+470 and −158/+503 was similar to that in fragment −158/+32. Luciferase activity in fragment −158/+573 was low, about 10% of that in fragment −158/+32 (the active promoter). See, FIG. 32A.

To determine if CpG sites in the 547 nt region downstream of the promoter affect $P2X_7$ transcription, selected CpG sites were mutated. See, FIG. 32B. The following mutations resulted in a significant increase in luciferase activity: +211/+212 (CG/AA), +257/+258 (CG/TT), +278/+279 (CG/TT), +319/+320 (CG/AT), +330/+331 (CG/AT), +424/+425 (CG/TT), +453/+454 (CG/TT), and +461/+464 (CGCG/ATTA). These data suggest that CpGs +211/+212, +257/+258, +278/+279, +319/+320, +330/+331, +424/+425, +453/+454, and a bi-CpG complex +461/+464 inhibit $P2X_7$ transcription.

2. Constitutive Hypermethylation of Downstream $P2X_7$ CpG Sites

A CpG-rich 547 nt region downstream of an active $P2X_7$ promoter may modulate transcription based upon changes in methylation status. Methylation status of cytosines within selected CpG sites in the 547 nt region was measured in: i) normal cultured human uterine cervical epithelial cells; ii) cancerous cultured human uterine cervical epithelial cells; iii) normal biopsied human cervix epithelial tissues; and iv) cancerous biopsied human cervix epithelial tissues.

cDNA segments of interest (i.e., for example, Segments 1-3) were generated from Aza-dC-treated HeLa cells and analyzed by the genomic DNA bisulfite conversion method followed by gene specific PCR and restriction enzyme cutting. The amplified segments were cut with restriction enzymes to detect potential methylation-sensitive cytosines at CpG sites. Sites +193/+194 and or +211/+212 (Segment-1), and +330/+331 (Segment-2) were cut with MaeII; sites +461/+462 and or +463/+464 (Segment-3) were cut with BstUI. See, FIG. 28.

Demethylation with Aza-dC decreased restriction enzyme cleavage at CpG sites in all three segments. Densitometry scans showed that the degree of cleavage at CpG sites (defined in terms of the ratio of densitometry of the cleaved band, relative to the uncleaved plus cleaved bands [%]) decreased in Segment-1 from 22% to 5%; in Segment-2 from 65% to 43%; and in Segment-3 from 48% to 22%. These data suggest that Aza-dC induced de-methylation of cytosines within CpG sites at the 547 by region, and confirmed the validity of the method that was used. See, FIG. 33A.

Human placental genomic DNA treated in vitro with the CpG methylase SssI was used as a positive control. See, FIG. 33B. Aliquots of placental DNA were mixed with different amounts of SssI and the degree of methylation was determined in terms of cleavage at CpG sites. The degree of methylation in the absence of methylase SssI was small, but it increased in a dose-related manner relative to the amount of Sss1 versus placental DNA in the reaction mixture. Compare, FIG. 33A and FIG. 33B.

Methylation status of cytosines within those CpG sites was compared between in vitro cultured normal and cancer human cervical cells and in vivo normal and cancer human cervix epithelial tissues. See, FIGS. 33C-E, and FIGS. 33F-I, respectively. The results revealed a greater degree of cleavage in cultured cancer cells than in cultured normal epithelial cervical cells. Similar experiments were done on human cervix epithelial tissues using specimens obtained by microdissection from uterine tissue cross-sections. Experiments utilized paired specimens from ten patients, including in each case normal and squamous cell carcinoma tissues. Sufficient amounts of tissues were available in nine cases for Segments 1 and 3 and in eight cases for Segment 2. These results also showed a greater degree of cleavage in cancer tissues than in normal tissues. See, FIGS. 33F-H.

Semi-quantitative analysis of the data in cultured cervical cells showed a 5-10 fold higher degree of cleaved fractions in all three segments in cancer cells than in normal cells. See, Table 6.

TABLE 6

The degree of the cleaved fractions (in terms of the ratio of densitometry of the cleaved versus the uncleaved plus cleaved bands [%]) at CpG sites +193/+194 (and/or +211/+212) (Segment 1); +330/+331 (Segment 2); and +461/+462 (and/or +463 +464) (Segment-3) downstream the P2X7 active promoter in cultured cancer and normal cervical cells (means ± SD of 3-4 experiments).

| | Segment-1 | Segment-2 | Segment-3 |
|---|---|---|---|
| Cancer Cells | | | |
| HeLa | 24 ± 63 | 23 ± 4 | 23 ± 2 |
| CaSki | 55 ± 23 | 38 ± 13 | 20 ± 4 |
| HT3 | 53 ± 17 | 35 ± 10 | 22 ± 4 |
| SiHa | 7 ± 3 | 12 ± 5 | 25 ± 5 |
| Normal Cells (hEVEC) | 2 ± 1* | 1 ± 2* | 13 ± 3* |

*P < 0.01.

These data suggest a greater degree of hypermethylation of cytosines at the tested CpG sites in the cancer cervical cells than in the normal cervical cells. Similar trends were obtained in cervix epithelial tissues in vivo. Densitometry ratios of [cleaved]/[uncleaved plus cleaved] fractions in normal and cancer tissues were obtained from the same patient. The results showed greater degree of cleaved fractions in cancer cases than in the corresponding normal tissues in 8/9 cases of Segment-1 (p<0.05); in 7/8 cases of segment-2 (p<0.01), and in 8/9 cases of Segment-3 (p<0.05). See, FIG. 33I.

Collectively, these data suggest that in cultured cervical cells and in the cervix in vivo cytosines within CpG sites +193/+194 (and or +211/+212), +330/+331, and +461/+462 (and or +463/+464) in the 547 by region downstream of the active $P2X_7$ promoter are hypermethylated to a greater degree in cancer cells than in normal epithelial cells.

F. Enhancer Region DNA-Protein Binding Sites

The data presented herein demonstrate that P2X7 promoter enhancer regions may bind transcription modulating factors. Further, CpG site hypermethylation status mediation of transcription activity may be explained by enhancer region proximity. Putative $P2X_7$ enhancer regions including, but not limited to, nt +222/+232 and +401/+573 in the 547 by region downstream of the active P2X7 promoter were shown to contain protein binding sites by using electrophoretic mobility shift assays (EMSA) using four amplified fragments, as described herein. See, Table 4 (infra). EMSA identified a first shifted band in the +217/+237 fragment; a second shifted band in the +401/+530 fragment; and a third, fourth, fifth and sixth shifted bands in the +401/+573 fragment. See, FIG. 34. (FIG. 7). These data indicate the presence of DNA-protein complexes in the +217/+237 and the +476/+573 regions.

G. $P2X_7$ Expression Regulator Proteins Bind to Methylated CpG Regions

In one embodiment, the present invention contemplates a method of treating and/or preventing cancer by administering compounds capable of binding to a $P2X_7$ receptor gene enhancer region, wherein the enhancer region increases $P2X_7$ receptor expression. In one embodiment, the $P2X_7$ gene comprises an enhancer region (i.e., for example, +222/+232). In one embodiment, the compounds modulate $P2X_7$ receptor expression regulator proteins. In one embodiment, the regulator proteins may be selected from the group including, but not limited to, p300, Elk-1, E47, E11aE, E2F, or p53. In one embodiment, a sequence of the putative enhancer region +222/+232 comprises binding sites for regulator proteins selected from the group including, but not limited to, p300, Elk-1, E47, EIIaE, E2F, or p53.

p300 has been reported to promote transcription by acetylating histones and integrating signaling from enhancer and promoter regions. Li et al., (2002) "Acetylation of p53 inhibits its ubiquitination by Mdm2" *J Biol Chem* 277:50607-50611. Elk-1 has been reported to regulate transcription by phosphorylation in response to activation of mitogen-activated protein kinase (MAPK) pathways. Yang et al., (2006) "Convergence of the SUMO and MAPK pathways on the ETS-domain transcription factor Elk-1" *Biochem Soc Symp* 73:121-129. E47 has been reported to be a member of the E2 protein family encoded by the E2A gene and may regulate cell development and differentiation. For example, a repression or absence of E47 activity have been implicated in cancer development. Yang et al., (2008) "E47 controls the developmental integrity and cell cycle quiescence of multipotential hematopoietic progenitors" *J Immunol* 181:5885-5894. Bioinformatics analysis of a sequence of the putative $P2X_7$ enhancer region +401/+573 revealed putative binding sites for p300, Elk-1 and E47, as well for EIIaE, E2F, and p53. EIIaE and E2F are also members of the E protein family; both control cell cycle progression and over-expression of E2F-1 can activate apoptosis. Mathis et al., (1981) "Specific in vitro initiation of transcription on the adenovirus type 2 early and late EII transcription units" *Proc Natl Acad Sci USA* 78:7383-7387; Hamel et al., (1992) "Transcriptional repression of the E2-containing promoters EIIaE, c-myc, and RB1 by the product of the RB1 gene" *Mol Cell Biol* 12:3431-3438; Zheng et al., (1999) "Structural basis of DNA recognition by the heterodimeric cell cycle transcription factor E2F-DP" *Genes Dev* 13:666-674; and Pardee et al., (2004) "Regulation in S phase by E2F" *Cell Cycle* 3:1091-1094.

The p53 tumor suppressor transcription factor is believed to play a role in the expression of genes involved in the regulation of cell cycle progression and cell death. Laptenko et al., (2006) "Transcriptional regulation by p53: one protein, many possibilities" *Cell Death and Differentiation* 13:951-961. Further, there may be an association between activation of the $P2X_7$ receptor and the p53 apoptotic pathway and/or between increased expression of the $P2X_7$ receptor and p53 protein levels. Schulze-Lohoff et al., (1998) "Extracellular ATP causes apoptosis and necrosis of cultured mesangial cells via $P2Z/P2X_7$ receptors" *Am J Physiol* 275:F962-F971; and Turner et al., (2007) "Increased expression of the pro-apoptotic ATP-sensitive P2X7 receptor in experimental and human glomerulonephritis" *Nephrol Dial Transplant* 22:386-395.

The data presented herein show that the putative enhancer +222/+232 and +401/+573 regions co-localize with, or are flanked by, constitutively methylated CpGs. Although it is not necessary to understand the mechanism of an invention, it is believed that the association of inhibitory CpGs with binding sites of putative enhancers suggests a gene expression regulatory mechanism, such that hypermethylated CpGs inhibit $P2X_7$ transcription by modulating the interaction of enhancer transcription factors with their cognate DNA binding domains. Consequently, it is further believed that demethylation of these CpGs would increase $P2X_7$ transcription.

In one embodiment, the present invention contemplates a method for treating and preventing cancer by modulating $P2X_7$ transcription regulation. See, FIG. 27. Transcription of the $P2X_7$ receptor may be regulated by cis-enhancer elements located in nt +222/+232 and +401/+573 downstream of an active $P2X_7$ promoter, which contain binding sites for transcription factors. Transcription of the $P2X_7$ receptor is negatively controlled by methylated CpG sites +193/+194 (and/or +211/+212), +330/+331, and +461/+462 (and/or +463+464) that flank the enhancers. Since transcription in cells expressing the −158/+573 nt construct was lower compared to that in cells expressing an active promoter (nt −158/+32), the data suggest that, under baseline conditions, the effect of the putative inhibitors surpasses that of the putative enhancer(s).

The present data demonstrate that cells may have devised mechanisms to regulate expression and activity of the $P2X_7$ receptor to avoid unneeded apoptosis. For example, enhancers of transcription downstream of an $P2X_7$ promoter may be controlled by neighboring hypermethylated CpG sites. Further, it has been reported that $P2X_7$ transcripts can be degraded post-transcriptionally by the actions of micro-RNAs. Zhou et al., (2008) "Micro-RNAs miR-186 and miR-150 downregulate expression of the pro-apoptotic purinergic $P2X_7$ receptor by activation of instability sites at the 3'-untranslated region of the gene that decrease steady-state levels of the transcript" *J Biol Chem* 283:28274-28286. Although it is not necessary to understand the mechanism of an invention, it is believed that hypotheses explaining reduced expression of the $P2X_7$ receptor, by hypermethylation of the CpGs in cancer cells may: i) be secondary to the cancer process; or ii) precede the carcinogenic stimuli such that the abrogated apoptosis predisposes cells to the development of cancer.

In summary, the data presented herein suggest that $P2X_7$ transcription may be regulated by two groups of direction-dependent cis regulatory enhancers located within a 547 nt region downstream of the active promoter (i.e, for example, segments +222/+232 and +403/+573). In one embodiment, the regulatory enhancers comprise co-localized or clustered CpG sites. In one embodiment, the CpG site comprises an inhibitory cis elements. Although it is not necessary to understand the mechanism of an invention, it is believed that an inhibitory cis element may be regulated by the amount of cytosine hypermethylation. In one embodiment, cervical cell CpG sites within the $P2X_7$ gene include, but are not limited to +211/+212+330/+331 and +461/+464. In one embodiment, the cervical cell CpG sites are hypermethylated to a greater degree in cancer cells than in the normal cervical cells. Although it is not necessary to understand the mechanism of an invention, it is believed that such increased CpG hypermethylation results in decreased $P2X_7$ receptor expression, thereby decreasing cell apoptosis.

In summary, the above data suggest that:
Reduced expression of the $P2X_7$ receptor may be associated with a reduced rate of apoptosis, thereby predisposing cells to the development of cancer.
$P2X_7$ transcription may be regulated by enhancer regions located within a 547 nt region (+26/+573) downstream of an active promoter.
$P2X_7$ transcription may be controlled by the hypermethylation status of cytosines at CpG sites that cluster and/or co-localize with an enhancers' sites.
Low expression of the $P2X_7$ receptor in epithelial cancer cells, e.g. uterine cervical cancer cells may be determined, in part, by an inhibition of transcription enhancers (i.e., for example, those enhancers located within a 547 nt region downstream of a promoter) increasing the hypermethylation status of flanking CpG sites.

V. Administration of $P2X_7$ Receptor Agonists $P2X_7$ receptor agonists can be administered to a subject by any means suitable for delivering these compounds to a subject. For example, $P2X_7$ receptor agonists can be administered by methods suitable enteral or parenteral administration route. Suitable enteral administration routes for the present methods include, but are not limited to, oral, rectal, or intranasal delivery. Suitable parenteral administration routes include, but are not limited to, intravascular administration (i.e., for example, intravenous bolus injection, intravenous infusion, intra-arterial bolus injection, intra-arterial infusion and catheter installation into the vasculature); peri- and intra-tissue injection (i.e., for example, peri-tumoral and intra-tumoral injection, intra-retinal injection, or subretinal injection); subcutaneous injection or deposition, including, but not limited to, subcutaneous infusion (i.e., for example, by osmotic pumps); direct application to the tissue of interest, for example by a catheter or other placement device (i.e., for example, a retinal pellet or a suppository or an implant comprising a porous, non-porous, or gelatinous material); and inhalation. Another administration route includes, but is not limited to, injection and/or infusion directly into a tumor.

Liposomes are used to deliver $P2X_7$ receptor agonists to a subject. Liposomes can also increase the blood half-life of the gene products or nucleic acids. Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods can be used for preparing liposomes. Szoka et al., *Ann. Rev. Biophys. Bioeng.* 9:467 (1980); and U.S. Pat. Nos. 4,235,871, 4,501,728, 4,837,028, and 5,019,369, the entire disclosures of which are herein incorporated by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES. U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include, but are not limited to, polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to a liposome membrane. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes. Gabizon, et al., *Proc. Natl. Acad. Sci., USA*, 18:6949-6953 (1988). In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miRNA gene products or miRNA gene expression inhibition compounds (or nucleic acids comprising sequences encoding them) to tumor cells.

VI. $P2X_7$ Receptor Agonist Pharmaceutical Formulations $P2X_7$ receptor agonists compounds are preferably formulated as pharmaceutical compositions, sometimes called "medicaments," prior to administering to a subject. Pharmaceutical compositions of the present invention are characterized as being at least sterile and pyrogen-free. As used herein, "pharmaceutical formulations" include, but are not limited to, formulations for human and veterinary use. Methods for preparing pharmaceutical compositions of the invention are described. In: Remington's Pharmaceutical Science, 17th ed., Mack Publishing Company, Easton, Pa. (1985), the entire disclosure of which is herein incorporated by reference.

Pharmaceutical formulations contemplated by the present invention comprise at least one $P2X_7$ receptor agonist (e.g., 0.1 to 90% by weight), or a physiologically acceptable salt thereof, mixed with a pharmaceutically-acceptable carrier. Pharmaceutical formulations of the invention may also comprise at least one $P2X_7$ receptor agonist which may be encapsulated by liposomes and/or a pharmaceutically-acceptable carrier. In one embodiment, a pharmaceutical composition comprises an $P2X_7$ receptor agonists including, but not limited to, BzATP. Preferred pharmaceutically-acceptable carriers are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include, but are not limited to, stabilizers, antioxidants, osmolality adjusting agents, buffers, and pH adjusting agents. Suitable additives include, but are not limited to, physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used including, but not limited to, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one $P2X_7$ receptor agonist. A pharmaceutical composition for aerosol (inhalational) administration can comprise 0.01-20% by weight, preferably 1%-10% by weight, of the at least one $P2X_7$ receptor agonist encapsulated in a liposome as described above, and a propellant. A carrier can also be included as desired; e.g., lecithin for intranasal delivery.

EXPERIMENTAL

All chemicals, unless specified otherwise, were obtained from Sigma Chemical (St. Louis, Mo.). Primary antibodies for the immunostaining and Western blots were as follows: Rabbit polyclonal anti-$P2X_7$ receptor antibody, which recognizes the functional full length $P2X_7$ receptor was from Alomone Laboratories (Jerusalem, Israel); rabbit anti-GAPDH antibody was from BD Transduction Laboratories (Lexington, Ky.). The secondary antibody was goat anti-rabbit Alexa Fluoro antibody (Invitrogen). Leu-Glu-His-Asp-O-methyl-fluoromethylketone (LEHD-FMK; SEQ ID NO:1), Ile-Glu-Thr-Asp-O-methyl-fluoromethylketone (IETD-FMK: SEQ ID NO: 2), Benzyloxy-valine-alanine-aspartate-O-methyl-fluoromethylketone (zVAD-FMK: SEQ ID NO: 3), and Asp-Glu-Val-Asp-O-methylfluoromethylketone (DEVD-FMK: SEQ ID NO: 4) were from Calbiochem La Jolla, Calif.), and were used at a concentration of 50 µM.

Example I

Human Keratinocyte Cell Cultures and Transfections

Primary cultures of human normal keratinocytes were generated from discarded foreskins. Tissues were obtained following non-ritual circumcision of newborn males at the nursery of the Department of Obstetrics and Gynecology, University Hospital CASE Medical Center according to approved IRB protocol 08-06-28. Human epidermal squamous cell carcinoma-9 (SCC-9) cells and Madin Darby canine kidney cells (MDCK, strain II) were obtained from the ATCC. MDCK cells lack endogenous expression of $P2X_7$ receptor, and MDCK cells expressing tetracycline-regulated repressor (Feng et al, 2006) were used for heterologous transfection expression experiments.

For inducible expression of $P2X_7$ receptors in MDCK cells, the human $P2X_7$ gene (NM_002562), including a Myc tag attached to the N-terminus was subcloned into pcDNA4/TO vector (Invitrogen) with Hind III and Not I sites. Primers, the method of transfections, and the generation of stable MDCK clones were described (Feng et al, 2006). Stable clones were maintained in tetracycline-free medium and 100 µg/ml zeocin. Expression of Myc-$P2X_7$ genes was induced by 100 ng/ml doxycycline, and expression of Myc-$P2X_7$ protein in stable MDCK cells was confirmed by RT-PCR (Feng et al, 2006). Cell cultures were maintained as described (Wang et al, 2005; Feng et al, 2006; Li et al, 2006; Li et al, 2007).

Example II

Protein Assays

Immunostaining and Western blots were described (Wang et al, 2005; Feng et al, 2006; Li et al, 2006; Li et al, 2007). Assays using human-derived cells (keratinocytes and SCC-9) and MDCK cells utilized the rabbit polyclonal anti-$P2X_7$ receptor antibody (Alomone Laboratories, Jerusalem, Israel); mouse anti-c-Myc antibody (Santa Cruz Biotechnology, Santa Cruz, Calif.); mouse anti-E-Cadherin antibody (Invitrogen, http://www.invitrogen.com); and the anti-tubulin antibody (From the Developmental Studies Hybridoma Bank, University of Iowa, Iowa City, Iowa). Assays using mouse tissues utilized the rabbit anti-$P2X_7$ receptor antibody, the rabbit polyclonal anti Ki67 antibody (Dako, http://www.dako.com), and goat anti-rabbit Alex Fluoro 546 secondary antibody (Invitrogen).

Image-analysis of immunofluorescence data was described (Li et al, 2007). Representative fields were captured and saved in Adobe Photoshop. Pictures were scanned using UN-SCAN-IT (Silk Scientific, Orem Utah) by choosing 3-5 representative fields for each picture. Light intensity in each field was digitized and average pixel density per field was determined using the program software.

Confocal laser microscopy was described (Feng et al, 2005). Briefly, MDCK cells were plated on 35-mm glass-bottom culture dishes (MatTek Corporation, Ashland, Mass.). Cells were immunostained with the anti-$P2X_7$ receptor antibody, and planar and vertical images were obtained in-situ.

Example III $P2X_7$ mRNA In-Situ Hybridization

Primers for the anti-sense and sense probes of the full length $P2X_7$ cDNA template were described (Li et al, 2006). For assays, cultured cells were plated on Poly-lysine-coated coverslips and grown in culture medium to subconfluence. Staining was evaluated using Nikon Eclipse 80i microscope (Melville, N.Y.).

Example IV

Real-Time PCR

Total RNA was extracted by RNeasy mini kit (QIAGEN, Valencia, Calif.) and one-step Real-time qPCR was carried out as described (Li et al, 2006; Li et al, 2007). Primers for the $P2X_7$, E-Cadherin and cytokeratin-18 (CK-18) (used for data normalization) and PCR conditions were described (Li et al, 2006; Li et al, 2007). Relative quantification (RQ) was calculated in terms of $C_t$ as described (Li et al, 2006; Li et al, 2007).

Example V

ATP Assays

Cells were grown on plates and maintained in a volume of 300 µl of Ringer's Solution. Twenty minutes after stabilization 50 µl aliquots of conditioned medium were collected and assayed by a chemiluminescent method linked to Firefly luciferase-luciferin as described (Wang et al, 2004a). Bubbled Ringer's solution was used as blank to determine background ATP, and ATP in the medium was determined from a standard curve of samples with known ATP concentrations. The lower limit of detection for ATP was 0.25 nM.

Example VI

Apoptosis Assays

Apoptosis may be quantified in terms of percent solubilized DNA (Wang et al, 2004a), or by using the commercial cell-death detection ELISA kit (Roche Applied Science, Nutley, N.J.) (Feng et al, 2006).

TUNEL assays in tissues cross sections were performed using DeadEnd™ Fluorometric TUNEL System (Promega, Madison, Wis.) according to the manufacturer's protocol. For TUNEL-$P2X_7$ co-staining, tissue cross sections were first assayed for TUNEL, followed by $P2X_7$ immunostaining. The modified combined method resulted in only negligible cross fluorescence interference.

Apoptosis of cultured mouse keratinocytes was quantified in terms of percent solubilized DNA, or by using the commercial cell-death detection ELISA kit (Roche Applied Science, Nutley, N.J.). Wang et al., "$P2X_7$-receptor mediated apoptosis of human cervical epithelial cells" *Am J Physiol* 2004, 287:C1349-C1358; and Feng et al., "A truncated $P2X_7$ receptor variant ($P2X_{7-j}$) endogenously expressed in cervical cancer cells antagonizes the full-length $P2X_7$ receptor through hetero-oligomerization" *J Biol Chem* 2006, 281: 17228-17237, respectively.

Example VII $P2X_7$-Antisense Oligonucleotides $P2X_7$-specific antisense oligonucleotides (ASO) and random control oligonucleotides (RCO) were designed from the published sequence of the human $P2X_7$ gene (NM_002562) using a previously described method. Zhu et al, 2006. The sequences of the 20-mer ASO that would hybridize to the coding region of exon 7 (nt 724-741), and the RCO were as follows: ASO-TTT CAG ATG TGG CAA TTC AG (SEQ ID NO: 5); RCO-TAT CAC ATC TCG CAA TAG AC (SEQ ID NO:6). In the RCO, the antisense sequence was randomly replaced with adenine and thymine residues so that the oligonucleotides had the same length (20-mer) and GC content (33%) as the ASO. The RCO was designed such that no cross-hybridization against the $P2X_7$ gene would occur. To assess the effects of the ASO and RCO on $P2X_7$ mRNA expression, cultured cells were treated with or without ASO or RCO at concentrations of 10 µM. qPCR assays were carried out after 2 days, and Western blots and apoptosis determinations were made after 3 days.

Example VIII

Animal Experiments

This example evaluates to what degree pharmacological activation of $P2X_7$-mediated apoptosis could inhibit cancer development in vivo. [55]

The experimental system was the mouse skin cancer model, based on the rationale that both in rodents and in humans the $P2X_7$ system plays an important role in the control of growth of keratinocytes [45-49,55]. Skin lesions were induced by the Two-Step procedure, which involves tumor initiation with 7,12-dimethyl-benz(a)anthracene (DMBA), and tumor promotion with 12-O-tetradecanoylphorbol-13-acetate (TPA). See, FIG. 23A. DMBA and TPA were applied locally on the shaved dorsal skin of mice. Control animals were treated either with DMBA/TPA or with BzATP alone. Data were evaluated after 28 weeks of treatment (for the DMBA/TPA and DMBA/TPA+BzATP groups) or after 4 and 16 weeks (for the BzATP group alone).

Experiments using mice were done according to an approved CWRU IACUC IRB protocol [2006-0141]. Experiments utilized 6-8 weeks old FVB female mice (obtained from Charles River, Wilmington, Mass.). The animal's dorsal skin (about 3×5 cm) was shaved using Oster animal clipper (Mountain Home, Ark.) followed by weekly application of Nair® hair remover lotion. Treatments included the application of one or more of the following drugs, directly onto the shaved dorsal skin: DMBA (50 µg/200 µl acetone [950 µM, 190 nmol, 3.3 µg/cm$^2$]); TPA (3 µg/200 µl acetone [20 µM, 4 nmol, 0.2 µg/cm$^2$]); BzATP (14.3 µg/200 µl of 2.3/1 vol/vol solution of propylene-glycol [PG]/ethanol [EtOH][100 µM, 20 nmol, 1.0 µg/cm$^2$]); or the BzATP vehicle only (200 µl of PG/EtOH). DMBA was applied once, while TPA and BzATP were applied twice a week. Skin neoplasia in the mice were induced by the "Two-Step" method, which involved tumor initiation by local treatment with 7,12-dimethylbenz(a)anthracene (DMBA), followed by tumor promotion with local treatment of 12-O-tetradecanoylphorbol-13-acetate (TPA). Guo et al., "Disruption of EphA2 receptor tyrosine kinase leads to increased susceptibility to carcinogenesis in mouse skin" *Cancer Res* 2006, 66:7050-7058. The concentration/dose of BzATP and frequency of treatments were chosen based on data in cultured cells (supra).

The shaved dorsal skin was divided into two equal anterior and posterior areas. Each animal was treated with BzATP applied locally twice a week for between 4-16 weeks on the anterior skin area; vehicle only was applied in parallel twice a week for 4 weeks on the posterior skin area. At the end of the experiment animals were euthanized by cervical dislocation and dorsal skin strips were obtained from each animal from the anterior and posterior skin areas for microscopic H&E tissue evaluation and $P2X_7$ immunostaining.

From each animal blood samples were obtained from the retro-bulbar venous complex for ALT (SGPT) and AST (SGOT) assays. In addition, dorsal skin strips were obtained from each animal for microscopic H&E tissue evaluation, Ki67 immunostaining, and in-situ detection of DNA fragmentation by the TUNEL method.

In some groups of animals, cancerous lesions were generated by using a DMBA/TPA treatment, both with and without the concurrent administration of BzATP. Control, no treatment; DMBA plus TPA; and DMBA/TPA plus BzATP. Treatments with BzATP began two weeks prior to the DMBA/TPA treatments. Endpoints were determined after 7-16 weeks. Endpoints were percent animals with at least one papilloma; number of papillomas per animal; and mean papilloma size (mm's determined at the largest lesion dimension). Some animals underwent biopsy of papillomas using mini rotary ElliptiPunch blade (HUOT, Menomonee Falls, Wis.). The biopsy tissues were assayed for microscopic H&E tissue evaluation, Ki67 immunostaining, and TUNEL.

Biopsy of skin papilloma was done on one living animal using mini rotary ElliptiPunch blade (HUOT, Menomonee Falls, Wis.). Criteria for euthanasia (by cervical dislocation) prior to week 28 were according to Montgomery guidelines, including animals with excessive tumor burden, or with ulcerated lesions regardless of size that were bleeding, necrosed, or infected. Hetherington et al., "Mouse care and husbandry" In: Mouse Genetics and Transgenics: A Practical Approach Edited by: Jackson I J, Abbott C M. Oxford University Press; 2000:1-25. The experiment was terminated at week 28, when all remaining living animals were euthanized. After death, representative samples were obtained from all skin lesions as follows: i) DMBA/TPA group—4 papillomas and 26 cancer samples; and ii) DMBA/TPA-BzATP group—2 papillomas and 12 cancer samples. All animals underwent postmortem exam for the presence of metastases and non-epidermal tumors (none were found).

Most lesions were defined as papillomas based on the actual histological diagnosis in one case, the typical morphological appearance, and the extensive experience gained by others using this model and methodology. Guo et al., "Disruption of EphA2 receptor tyrosine kinase leads to increased susceptibility to carcinogenesis in mouse skin" *Cancer Res* 2006, 66:7050-7058; and Glick et al., "The high-risk benign tumor: evidence from the two stage skin cancer model and relevance for human cancer" *Mol Carcinogenesis* 2007, 46:605-610. Lesions biopsied during 14-28 weeks were defined either as cancers (as diagnosed in each case at the time of death), or as non-cancerous lesions, including existing or involuting papillomas (diagnosed at the time of death) or lesions that disappeared prior to death.

The main results were as follows:
(a) Local administration of DMBA/TPA induced skin papillomas at weeks 5-12, and squamous spindle-cell carcinomas afterwards. See, FIG. 23B-I.
(b) At weeks 0-12 the incidence of papillomas was lower by about 50% in animals co-treated with BzATP.
(c) The development of cancerous lesions was significantly slower and lesser in the DMBA/TPA+BzATP group than in the DMBA/TPA group. At week 28 the incidence of cancerous lesions was lower by about 50% in animals co-treated with BzATP. See, FIG. 24A.
(d) The survival rates showed a tendency for earlier deaths in the DMBA/TPA group than in the DMBA/TPA+BzATP group. See, FIG. 24B.
(e) In the normal skin, $P2X_7$ immunoreactivity localized predominantly within proliferating keratinocytes at the basal/parabasal layers, and in hair shafts. See, FIG. 25A and FIG. 25B.
(f) In papillomas, $P2X_7$ immunoreactivity was similar to normal tissues, and it localized predominantly within proliferating keratinocytes at the base of the developing papillomas. See, FIGS. 25C and 25D.
(g) In cancer cells, $P2X_7$ immunoreactivity and $P2X_7$ mRNA levels were 4-5 fold lower than in normal epidermal or papilloma cells. See, FIGS. 25E-H.
(h) Treatment with BzATP up-regulated apoptosis of $P2X_7$ receptor expressing cells in:
  i) normal skin (See, FIGS. 26A-N);
  ii) DMBA/TPA-induced papilloma keratinocytes (See, FIGS. 26O-R), and
  iii) DMBA/TPA-induced cancer cells (See, FIGS. 26S-V).
The effect in cancer cells was smaller than in normal or papilloma keratinocytes. See, FIG. 26.
(i) Treatment with BzATP had no significant effect on the morphology and histological characteristics of the skin. See, FIGS. 6A and 6B.
(j) The local treatment with BzATP had no significant effect on the behavior of the animals, feeding habits, body weight, and liver functions.

In summary, local treatment with the $P2X_7$-receptor-specific ligand BzATP decreased the development of DMBA/TPA-induced skin papillomas and skin cancers in mice by 50%. BzATP was observed to augment apoptosis in proliferating keratinocytes. Local treatment with BzATP did not produce local or systemic adverse effects.

Example IX

ALT (SGPT) and AST (SGOT) Assays

Assays used Liquid ALT and Liquid AST reagent sets (Cat # A7526-150a and A7561-150, respectively) obtained from Pointe Scientific (Canton Mich.), and were performed according to the supplier instructions.

Example X

Data Analysis

The proportion of living animals with papillomas or cancerous lesions was calculated at each week throughout the study period and compared between groups by chi-square or Fisher's exact test. Time-to-event data were used to assess differences in the formation of cancerous lesions and the Kaplan-Meier method (with log-rank test) was used to compare differences between groups.

Mean number of lesions per animal was calculated at each week and compared between groups by independent samples t-test. In addition, repeated-measure ANOVA was used to examine the effect of time and number of lesions between groups.

Mean lesion size was compared similarly for weeks 0-12. For weeks 14-28, non-cancerous and cancerous lesions were categorized as $\leq 10$ mm$^3$ versus $>10$ mm$^3$ and the proportion of lesions $>10$ mm$^3$ in living animals was compared between groups by $\chi$2-square or Fisher's exact test. Cancerous lesions were also categorized as $\leq 200$ mm$^3$ versus $>200$ mm$^3$.

Cancer development (for weeks 14-28) and survival rates (for weeks 0-28) were evaluated using the Kaplan-Meier method and compared between groups by log rank test. For cultured cells data, significance of differences between groups was estimated by t-test, or by one-way or two-way ANOVA with Tukey-Kramer Multiple Comparisons post test analysis.

Example XI

Mouse Keratinocyte Cell Culture

The experiments utilized primary cultures of epidermal keratinocytes generated from 6-8 weeks old wild-type C57B1 mice (Charles River, Wilmington, Mass.); from $P2X_7^{-/-}$ Pfizer mice constructed by deletion of amino acids 506-532 of the C-terminus (Solle et al., "Altered cytokine production in mice lacking P2X(7) receptors" *J Biol Chem* 2001, 276: 125-32), or from $P2X_7^{-/-}$GSK mice, which have a lacZ gene inserted at the beginning of exon 1, resulting knockout of the receptor. Sikora et al., "Purinergic signaling regulates radical-mediated bacterial killing mechanisms in macrophages through a $P2X_7$-independent mechanism" *J Immunol* 1999, 163:558-61. The $P2X_7^{-/-}$Pfizer and $P2X_7^{-/-}$GSK mice were generated on the C57B1 background.

Primary cultures of mouse keratinocytes were generated by a modified collagenase-EDTA method. Li et al., "Decreased expression of P2X7 in endometrial epithelial pre-cancerous and cancer cells" *Gynecol Oncology* 2007, 106:

233-243. Ventral superficial skin areas involving the full epidermis and part of the dermis were scraped and the cell suspension was washed by PBS and filtered through a 40-μm cell strainer. Following repeated washes and spinning cells were plated at a density of $1\times10^5$ cells per $cm^2$ on type-I collagen-coated filters and used for experiments after 24-48 hours.

P2X$_7$-specific antisense oligonucleotides (ASO) and random control oligonucleotides (RCO) were designed from the published sequence of the mouse P2X$_7$ gene (Accession Number AJ009823), using a previously described method. Chessell et al., "Cloning and functional characterisation of the mouse P2X$_7$ receptor" *FEBS Lett* 1998, 439:26-30; and Zhu et al., "Changes in Tight Junctional Resistance of the Cervical Epithelium are Associated with Modulation of Content and Phosphorylation of Occludin 65 KDa and 50 KDa forms" *Endocrinology* 2006, 147:977-989.

The sequences of the 20-mer ASO that would hybridize to the coding region of exon 13 (nt 1467-1486), and the RCO were as follows: ASO-GGC GTA CCG CAG CAA CGT (SEQ ID NO: 1): AG; RCO-TAA GTA CTG CAG CTA CGT AC (SEQ ID NO: 2) These sequences were designed such that no cross-hybridization against the P2X$_7$ gene occurs. To assess the effects of the ASO and RCO on P2X$_7$ mRNA expression, cultured cells were treated for 14 hours with or without 100 μM ASO or RCO.

Example XII

Cytosolic Calcium ($Ca^{2+}_i$) and Ethidium-Bromide Assays

Changes in $Ca^{2+i}$ in cultured cells were determined in terms of changes in intracellular Fluo-4 fluorescence using dynamic confocal laser scanning microscopy. Cultured mouse keratinocytes were loaded with 5 μM Fluo-4/AM, and imaged with a Zeiss LSM 510 inverted real-time confocal microscope. Images were collected at 488 nm/505 nm (exc/emi) at intervals of 10 to 15 seconds after treatment with 100 μM BzATP, added to the perfusate. For ethidium bromide influx experiments, glass-bottomed dishes cultured with mouse keratinocytes were placed in the microscope. Images (collected at 488 nm/505 nm [exc/emi]) were taken before, and at intervals of 30 seconds after adding 5 μM ethidium bromide to the perfusate as described. Average fluorescence intensity was quantified from collated images using MetaVue software (Fryer Company Inc., Huntley, Ill.) by subtracting the basal intensity value.

Example XIII

DNA Synthesis Assay

Changes in DNA synthesis were determined in terms of [$^3$H]-thymidine incorporation as described Wang et al., "EGF facilitates epinephrine inhibition of P2X7-receptor mediated pore formation and apoptosis: a novel signaling network" *Endocrinology* 2005, 146:164-174. The radioactivity (dpm/mg Protein, determined by Bio-Rad Protein Assay solution [Hercules, Calif.]) of triplicated samples was determined by beta scintillation counting (Beckman LS1801 scintillation counter).

Example IVX

BzATP Effects on P2X$_7$ Receptor Activation

BzATP treatment was reported to augment apoptosis in vivo in mouse papilloma and in mouse cancer cells. See, FIGS. 26P, 26R and FIGS. 26T,26V, respectively, as reported in [55].

The effect in papilloma cells was greater than in cancer cells. Compare, FIGS. 26R and 26V. In papilloma and in cancer cells, baseline apoptosis and the BzATP-induced augmented apoptosis correlated with receptor expression. See, FIGS. 26P,26T and FIGS. 26R,26V, respectively. High densities of the receptor in papilloma keratinocytes was associated with high baseline apoptosis and with high degree of BzATP-augmented apoptosis. See, FIG. 26O and FIG. 26Q. In contrast, low densities of the receptor in cancer cells was associated with low baseline apoptosis and with low degree of BzATP-augmented apoptosis. See, FIG. 26S and FIG. 26U. Steady-state levels of ATP in extracellular fluid of normal and cancer epithelial cells are reported to be similar [38,40,42, 55]. Therefore, the above mouse data suggest that in vivo the degree of receptor activation and apoptosis is determined mainly by the level of receptor expression, rather than by its affinity to ATP. See, FIG. 26.

In vivo treatment of mice with BzATP resulted in 50% inhibition of papilloma and cancer formation. The experiments used a relatively low dose of 1 μg/cm$^2$ BzATP, calculated based on the pre-maximal concentration of 100 μM required for apoptosis in cultured cells [38,40-42,50,55]. The BzATP treatment involved twice weekly applications of the drug on the skin, with the anticipation that BzATP is absorbed from the application site and will reach a sufficiently high concentration at its destined target of P2X$_7$-receptor-expressing reserve cells. The results showed that BzATP up-regulated apoptosis of P2X$_7$-receptor-expressing cells in the basal/parabasal layers and in hair shafts. However, it is unknown whether tissue levels reached the anticipated 100 μM concentration of BzATP, and it is possible that the effect was induced by lower tissue levels of BzATP. Theoretically, it could be possible to produce greater inhibition of skin papillomas and cancers by providing higher concentrations of BzATP at the target skin reserve cells.

In addition to drug pharmacokinetics, the data also raise the question which types of keratinocytic reserve cells have responded to BzATP. In the normal skin treatment with BzATP induced apoptosis in most, but not in all proliferating P2X$_7$-receptor-expressing cells. See, FIG. 26N.

Example XV

Identification of P2X$_7$ Gene Promoter Enhancer Sites

Cell Cultures

Primary cultures of human ectocervical-vaginal epithelial cells (hEVEC), a well-characterized model of the normal human ectocervical epithelium, were generated from discarded normal ectocervical-vaginal tissues. Wang et al., (2004) "P2X$_7$-receptor mediated apoptosis of human cervical epithelial cells" *Am J Physiol* 287:C1349-C1358. Human cervical epithelial cancer cell lines (Caski, Hela, Siha, and HT3), and human embryonic kidney 293 cells (HEK293), which lack endogenous expression of P2X$_7$, were obtained from the ATCC. Cell culture conditions have been described. Feng et al., (2006) "A truncated P2X$_7$ receptor variant (P2X$_{7-j}$) endogenously expressed in cervical cancer cells antagonizes the full-length P2X$_7$ receptor through hetero-oligomerization" *J Biol Chem* 281:17228-17237.

Elucidation of the Promoter Region

HindIII-tailed sense primers and the NcoI-tailed antisense primers (InVitrogen, Carlsbad Calif.) were used for the elucidation of the promoter region of the human P2X$_7$ gene (GenBank Y12851). See, Table 1.

TABLE 1

Primers for elucidation of the promoter region.
Segments are numbered relative to the
Transcription Initiation Start Site.

HindIII-tailed sense

-1664 TTT TTA AGC TTA AGA TGT GAA GCC AGG ATC G
(SEQ ID NO: 7)

-1179 TTT TTA AGC TTG GAT CAA GCC AGC TGTA
(SEQ ID NO: 8)

-698 TTT TTA AGC TTG GTG GTG TCC CTC ACT GAA T
(SEQ ID NO: 9)

-399 TTT TTA AGC TTG GGG CTG AAT AAA GGG TTG T
(SEQ ID NO: 10)

-204 TTT TTA AGC TTA ATG CCC ATC CTC TGA ACA C
(SEQ ID NO: 11)

-158 TTT TTA AGC TTG CCA GCT GGG GTG AGG TCA TCT G
(SEQ ID NO: 12)

-122 TTT TTA AGC TTT AGG ACT TGG CGC TTC TTG T
(SEQ ID NO: 13)

-73 TTT TTA AGC TTA GGG CCC GCC CCA ACT CTG GAG
(SEQ ID NO: 14)

-53 TTT TTA AGC TTA GTC ATT GGA GGA GCT TGA AGT TA
(SEQ ID NO: 15)

NcoI-tailed antisense

-380 TTT TTC CAT GGA CAA CCC TTT ATT CAG CCC C
(SEQ ID NO: 16)

+32 TTT TTC CAT GGC ACA GCA AGC CCC CTC CCA GTA
(SEQ ID NO: 17)

+91 TTT TTC CAT GGG GTG ACA GCC TCC CTC CCT GCG CG
(SEQ ID NO: 18)

+221 TTT TTC CAT GGC TTA CCA AAC GTA GGA AAA
(SEQ ID NO: 19)

+232 TTT TTC CAT GGC CCA GAT CCC ACT TAC CAA A
(SEQ ID NO: 20)

+337 TTT TTC CAT GGA GAG CAC GTC TCA GAT TCG AA
(SEQ ID NO: 21)

+402 TTT TTC CAT GGG CTG CAG CCT GGC ACC GTT TC
(SEQ ID NO: 22)

+470 TTT TTC CAT GG TGC GCG CCC TGG CGG GC
(SEQ ID NO: 23)

+503 TTT TTC CAT GGC CTG CGC TTT CCT ACC TTC CC
(SEQ ID NO: 24)

+573 TTT TTC CAT GGT CAG ATG CCA GCA TGA TCA CCA GGC
(SEQ ID NO: 25)

Corresponding cDNA fragments were synthesized by PCR using human genomic DNA. The PCR fragments were digested with HindIII and NcoI and ligated into pGL3 enhancer vector (Promega, Madison, Wis.) with HindIII and NcoI sites using Rapid DNA Ligation Kit (Roche, Indianapolis, Ind.). Reporters in this experiment and in all the experiments described below were confirmed by sequencing.

Control plasmids containing the pGL3 luciferase enhancer vector (5064 nt) or test plasmids (P2X$_7$-luciferase) were transfected into subconfluent cultured HEK293 cells that were plated 14 hours earlier in 6-well plates at a density of 2.5×10$^5$ cells per well. The culture medium was replaced with fresh medium plus 100 µl serum free medium per well, containing 2.5 µl Fugene 6 (Roche) and 750 ng DNA of the control or test vectors. For luciferase activity determinations cells were cotransfected with Renilla luciferase and 30 ng of the pRL-CMV vector (Promega). Zhou et al., (supra). At the completion of incubations cells were harvested and maintained in lyses buffer for 24 hours (Promega); Firefly and Renilla luciferase activities were measured consecutively by using Dual-Luciferase Reporter Assay System (Promega), and luciferase activity was determined in terms of Fluc/Rluc. For determinations of changes in P2X$_7$ and Firefly luciferase (Flue) mRNA, cells were lysed followed by RNA extraction. P2X$_7$ and Fluc mRNA levels were determined by Real-Time PCR (qPCR) relative to cytokeratin-18 (CK-18) or GAPDH, and expressed in terms of the threshold cycle of fluorescence (Ct). Primers for P2X$_7$, Fluc, CK-18 and GAPDH were described. Li et al., (2006) "The P2X$_7$ Receptor: A novel biomarker of uterine epithelial cancers" *Cancer Epidemiol Biomarkers Preven* 15:1-8, Feng et al., (2006) "A truncated P2X$_7$ receptor variant (P2X$_{7-j}$) endogenously expressed in cervical cancer cells antagonizes the full-length P2X$_7$ receptor through hetero-oligomerization" *J Biol Chem* 281:17228-17237: Li et al., (2007) "Decreased expression of P2X7 in endometrial epithelial pre-cancerous and cancer cells" *Gynecol Oncology* 106:233-243; Zhou et al., (2008) "Micro-RNAs miR-186 and miR-150 downregulate expression of the pro-apoptotic purinergic P2X$_7$ receptor by activation of instability sites at the 3'-untranslated region of the gene that decrease steady-state levels of the transcript" *J Biol Chem* 283:28274-28286.

Elucidation of the Transcription Initiation Start Site (TpIS)

A modified 5' Rapid Amplification of cDNA Ends method (5'-RACE) was used with primers (InVitrogen) as shown. See, Table 2.

TABLE 2

A. Primers for elucidation of the Transcription Initiation Start Site (TpIS).
B. Primers for elucidation of TATA-like Sites.

A

Anchor Hindu-tailed dT
GGA CCA AGC TTA TCG ATG TCG ACT TTT TTT TTT TTT TTT V
(SEQ ID NO: 26)

HindIII-including anchor
GGA CCA AGC TTA TCG ATG TCG AC
(SEQ ID NO: 27)

Anti-sense primers
Biotin-labeled (located at Exon-3)
GCT CTT GGC CTT CTG TTT TG
(SEQ ID NO: 28)
Nested (located at Exon-2)
GGT GTA GTC TGC GGT GTC AA
(SEQ ID NO: 29)
nested HIndIII-tailed (located at Exon-2)
CCG CTA AGC TTG CTT GTC ACT CAC CAG AGC A
(SEQ ID NO: 30)

| Mutation | Primers |
|---|---|
| B | |
| CATT/GTAA (nt -1 to +3) | Forward - CAG TAC GTT TGT AAT TGC AGT TAC TG (SEQ ID NO: 31) Reverse - CAG TAA CTG CAA TTA CAA ACG TAC TG (SEQ ID NO: 32) |

TABLE 2-continued

A. Primers for elucidation of the Transcription Initiation Start Site (TpIS).
B. Primers for elucidation of TATA-like Sites.

| | |
|---|---|
| TA/CC<br>(nt −31 to −30) | Forward - GAG CTT GAA GTC AAA GAC TCC TG<br>(SEQ ID NO: 33)<br>Reverse - CAG GAG TCT TGG ACT TCA AGC TC<br>(SEQ ID NO: 34) |
| AGGG/TATA<br>(nt −73 to −70) | Forward - GCC ACT GCC TAT ACC CGC CCC A<br>(SEQ ID NO: 35)<br>Reverse - TGG GGC GGG TAT AGG CAG TGG C<br>(SEQ ID NO: 36) |
| TT/CC<br>(nt −102 to −101) | Forward - TGG CGC TTC TTG TCC ATC ACA GC<br>(SEQ ID NO: 37)<br>Reverse - GCT GTG ATG GAC AAG AAG CGC CA<br>(SEQ ID NO: 38) |

Cloning, by reverse transcription (RT), was carried out at 55° C. (total of 20 μg RNA per reaction), using Invitrogen SuperScript™ III Reverse Transcriptase (InVitrogen). Biotin-labeled primers were used for RT to produce cDNA, and the biotin-labeled cDNA was combined with Dynabeads in order to concentrate the cDNA product and facilitate its purification. To this aim, the RT reaction was mixed with 40 μl Dynabeads M-280 streptavidin (Invitrogen) at 25° C. for 30 min; beads were washed in buffer containing 10 mM Tris pH 7.5, 1 mM EDTA, and 2M NaCl, and the beads-attached cDNA was tailed using Terminal Transferase (Promega) with dATP at 37° C. for 20 min and at 70° C. for 10 min. PCR was done with a primer pair of anchor TTT and the gene specific nested primers. A second PCR was done with the anchor primer and the nested HindIII antisense primer using the first PCR products diluted 100 fold. The resulting cDNA fragment was cloned into pGL3 enhancer vector with HindIII site, and confirmed by sequencing. The primary TpIS was identified from the sequence, beginning with adenine, and designated as site +1 (nt 1683 of the published human P2X7 gene sequence [GenBank Y12851]).

Oligonucleotide-directed mutagenesis of regions of interest within the promoter region utilized the pGL3 enhancer vector reporter containing fragment −158 to +32 and the PCR method. Regions of interest and mutations were as follows: nt −1 to +3 (CATT/GTAA); nt −31 to −30 (TA/CC); nt −73 to −70 (AGGG/TATA); and nt −102 to −101 (TT/CC). Primers are shown in Table 2 (supra).

Mutagenesis of CpG Sites

Mutations in the CpG sites within the 547 nt region downstream of the $P2X_7$ promoter were as follows: +211/+212 (CG/AA), +257/+258 (CG/TT), +278/+279 (CG/TT), +319/+320 (CG/AT), +330/+331 (CG/AT), +424/+425 (CG/TT), +461/+464 (CGCG/ATTA), +453/+454 (CG/TT), +475/+476 (CG/TT), +498/+499 (CG/TT), and +548/+549 (CG/TT). using the following primers. See, Table 3.

TABLE 3

Primers for CpG Mutagenesis Experiments

| Segment<br>(CpG site) | Mutation | Primers | |
|---|---|---|---|
| −158/+221<br>(+211/+212) | CG/AA | Reverse - TTT TTC CAT GGC TTA CCA AAT TTA GGA AAA G | (SEQ ID NO: 39) |
| −158/+337<br>(+257/+258)<br>(+278/+279)<br>(+319/+320)<br>(+330/+331) | CG/TT<br>CG/TT<br>CG/AT<br>CG/AT | Forward - ATC TCT GCA GTG GCT TAC AGC ACA<br>Reverse - TGT GCT GTA AGC CAC TGC AGA GAT<br>Forward - AAG CCC GAG TTG GCA GCT TCA G<br>Reverse - CTG AAG CTG CCA ACT GGG GCT T<br>Reverse - TTT TTC CAT GGA GAG CAC GTC TCA GAT TAT AAA<br>Reverse - TTT TTC CAT GGA GAG CAA TTC TCA GAT TCG AA | (SEQ ID NO: 40)<br>(SEQ ID NO: 41)<br>(SEQ ID NO: 42)<br>(SEQ ID NO: 43)<br>(SEQ ID NO: 44)<br>(SEQ ID NO: 45) |
| −158/+470<br>(+424/+425)<br>(+453/+454)<br>(+461/+464) | CG/TT<br>CG/TT<br>CGCG/ATTA | Forward - CAC AGG ACA AGT TGG ATT CCT<br>Reverse - AGG AAT CCA ACT TGT CCT GTG<br>Reverse - Nco)TTT TTC CAT GGC CCT GCG CGC CCT GGA AGG C<br>Reverse - TTT TCC CAT GGC CCT GTA ATC CCT GGC GGG C | (SEQ ID NO: 46)<br>(SEQ ID NO: 47)<br>(SEQ ID NO: 48)<br>(SEQ ID NO: 49) |
| −158/+573<br>(+475/+476)<br>(+498/+499)<br>(+548/+549) | CG/TT<br>CG/TT<br>CG/TT | Forward - GCA GGG TTT GCC TGG GGA AGG TAG<br>Reverse - CTA CCT TCC CCA GGC AAA CCC TGC<br>Forward - GTA GGA AAG TT AGG GCA ACA C<br>Reverse - GTG TTG CCC TGA ACT TTC CTA C<br>Reverse - Nco)TTT TCC ATG GTC AGA TGC GAG CAT GAT CAC CAG GAA TGG C | (SEQ ID NO: 50)<br>(SEQ ID NO: 51)<br>(SEQ ID NO: 52)<br>(SEQ ID NO: 53)<br>(SEQ ID NO:54) | cDNA fragments composed of the $P2X_7$ active promoter attached with the downstream 547 nt region containing the wild-type or mutant sequences were inserted into a luciferase vector and transfected into HEK293 cells. Promoter activity was determined in terms of luciferase activity.

$P2X_7$-Receptor Immunostaining

Rabbit polyclonal anti-$P2X_7$ receptor antibody (primary, from Alomone Laboratories, Jerusalem, Israel) [9] and goat anti-rabbit Alexa Fluoro 594 (secondary, from Invitrogen)

were used in a previously described method. Li et al., (2006) "The P2X$_7$ Receptor: A novel biomarker of uterine epithelial cancers" *Cancer Epidemiol Biomarkers Preven* 15:1-8; Fu et al., (2009) "Activation of P2X$_7$-mediated apoptosis inhibits DMBA/TPA-induced formation of skin papillomas and cancer in mice. *BMC Cancer* 9:114; and Li et al., (2007) "Decreased expression of P2X7 in endometrial epithelial precancerous and cancer cells" *Gynecol Oncology* 106:233-243.

Immunofluorescence was captured in a fluorescence microscope Nikon Eclipse 80i (Nikon, Melville N.Y.). Image analysis of the immunofluorescence data was performed and expressed in terms of average pixel density per cell. Feng et al., (2006) "A truncated P2X$_7$ receptor variant (P2X$_{7-j}$) endogenously expressed in cervical cancer cells antagonizes the full-length P2X$_7$ receptor through hetero-oligomerization" *J Biol Chem* 281:17228-17237.

Apoptosis Assays

Apoptosis was quantified by using Roche Cell Death Detection ELISA Kit (Roche). Feng et al., (2006) "A truncated P2X$_7$ receptor variant (P2X$_{7-j}$) endogenously expressed in cervical cancer cells antagonizes the full-length P2X$_7$ receptor through hetero-oligomerization" *J Biol Chem* 281: 17228-17237.

In Vitro Methylation Assays

Control (pGL3 luciferase enhancer vector) or test plasmids (P2X$_7$-promoter-luciferase) were methylated in vitro prior to transfections by incubations with the CpG-Methylase M.SssI (which adds a methyl group in cytosine residues) according to the manufacturer's protocol (New England Biolabs, Ipswich, Mass.).

Electrophoretic Mobility Shift Assay (EMSA)

A pGL3 enhancer Vector with an insert of the P2X$_7$ promoter was used as the template, and assays were performed using LightShift® Chemiluminescent EMSA Kit (Pierce, Rockford, Ill.). Briefly, biotin-labeled fragments were amplified by PCR with at least one primers as shown, See, Table 4 (includes SEQ ID NOs: 55-61 and 69).

luminator. Streptavidin-horseradish peroxidase conjugate and the LightShift Chemiluminescent Substrate (Pierce) were used to detect the biotin end-labeled DNA, and the nylon membranes were exposed to x-ray film for 3 minutes for detection of possible DNA-protein binding reactions.

Human Tissues

Discarded human uterine tissues were used for DNA methylation analysis. Tissues were obtained from the Human Tissue Procurement Facility of University Hospital CASE Medical Center, Case Western Reserve University, Cleveland Ohio, according to approved research protocols 12-03-50 and 03-90-300 by the Institutional Review Board. Cross sections of cervical segments were obtained from paraffin embedded blocks that were prepared by the Department of Pathology initially to establish the patient's diagnosis. For the assays, additional parallel 10 µm sections were cut and slides were made according to standard procedures. For each case an H&E stained slide was used to identify normal or cancerous cervical epithelial regions. Tissue epithelial fragments were obtained from parallel regions of non-stained slides by microdissection. The tissue material was dispersed into 100 µl digestion buffer (50 mM Tris pH 8.5, 0.5% Tween 20, 200 µg/ml proteinase-K), incubated at 42° C. overnight, and proteinase-K was inactivated by incubation at 80° C. for 10 min.

DNA Methylation Analysis

Assays used the method of combined bisulfite restriction analysis (COBRA) which employs restriction enzyme digestion to reveal methylation-dependent sequence differences in PCR products of sodium bisulfite-treated DNA. Xiong et al., (1997) "COBRA: a sensitive and quantitative DNA methylation assay" *Nucleic Acid Research* 25:2532-2534. Briefly, bisulfite-treated, genomic DNA unmethylated cytosines are converted to thymidines whereas methylated cytosine residuals are retained as cytosines. DNA segments of interest are amplified using PCR primers that do not contain CpG dinucleotides so that the amplification step does not discriminate between templates by their original methylation status.

TABLE 4

Primers for the electrophoretic mobility shift assays

| Fragment | Forward (Biotin-labeled at 5') | Reverse | Product Size |
|---|---|---|---|
| F401-475 | GCAGAGAGAAGCCACAGGA (SEQ ID NO: 69) | GCCCTGCGCGCCCTGGCG (SEQ ID NO: 55) | 75 bp |
| F401-530 | GCAGAGAGAAGCCACAGGA (SEQ ID NO: 56) | CCTGCGCTTTCCTACCTTCCC (SEQ ID NO: 57) | 103 bp |
| F401-573 | GCAGAGAGAAGCCACAGGA (SEQ ID NO: 58) | TCAGATGCCATCATGATCACC (SEQ ID NO: 59) | 173 bp |
| F217-237 | GTAAGTGGGATCTGGGGAGGA (SEQ ID NO: 60) | TCCTCCCCAGATCCCACTTAC (SEQ ID NO: 61) | 21 bp |

After amplification, P2X$_7$ promoter fragments were separated on 1.5% agarose gel and extracted using the Agarose Gel Extraction Kit (QIAGEN). The binding reaction was performed for 30 min at room temperature using the EMSA kit system in a total volume of 20 µL containing 2 µl binding buffer, 0.5 µg of HeLaScribe Nuclear Extract (Promega), 40 fmol biotin-labeled oligonucleotide, and 1 µl poly (dI-dC). DNA-protein complexes formed were fractionated by electrophoresis over 4% polyacrylamide gels in 1× Tris-boric acid-EDTA buffer. Gels were electrophoretically transferred at 100V for 1 hour on ice to a positively charged nylon membrane and immediately cross-linked with a UV transil- The PCR products are digested by restriction enzymes that recognize sequences containing CpG. Cleavage occurs if the CpG sequence has been retained during the bisulfite conversion according to the methylated status of the cytosine residue. The digested PCR products are resolved and separated by gel electrophoresis and stained with ethidium bromide.

Cloning of CpG-Rich Regions Downstream of the Promoter

Patterns of methylation were determined within a 547 by region of nt +26/+573 relative to a TpIS, nt +1. See, FIG. 28. The region of interest was arbitrarily divided to three segments with partial overlaps, designated Segment-1 (nt +26/+

247), Segment-2 (nt +223/+399), and Segment-3 (nt +352/+573) wherein the following primers were used. See, Table 5.

TABLE 5

Primers for experiments using Segments 1-3

| Segment-1 | Forward - TGT TGT GGT TTT GTT AGG AAG AGT A (SEQ ID NO: 63) Reverse - AAA AAT CTA AAT CCT CCC CAA ATC (SEQ ID NO: 64) |
|---|---|
| Segment-2 | Forward - GGA TTT GGG GAG GAT TTAGATT-3 (SEQ ID NO: 65) Reverse - CAA CCT AAC ACC GTT TCCTCTT-3 (SEQ ID NO: 66) |
| Segment-3 | Forward - GGG AGG GAG GAA GTA GTA GTA GGT A (SEQ ID NO: 67) Reverse - TCA AAT ACC AAC ATA ATC ACC AAA C (SEQ ID NO: 68) |

PCR conditions (annealing temperature) and the restriction enzyme used were as follows: Segment-1 560C (MaeII); Segment-2 560C (MaeII); Segment-3 590C (BstUI).

Evaluation of DNA Methylation

Genomic DNA was extracted from cultured cells and from human tissues using a DNA purification kit (Promega). To convert CpG non-associated cytosines to uracil (and thymidines), 1 mg of genomic DNA was denatured with 2 M NaOH at 37° C. for 10 min; 30 μl of 10 mM hydroquinone were added and the solution was incubated with 3M sodium bisulfite (pH 5) at 53° C. for 16 hours in darkness. After treatment, DNA was purified by DNA clean up kit (Promega). The solution was incubated with 2 M NaOH at room temperature and precipitated with 100% ethanol, washed with 70% ethanol, and resuspended in 20 μl of distilled water. The bisulfite treated DNA was amplified by PCR (95° C. 5 min/ 95° C. 30 sec/55-59° C. 45 sec/and 72° C. 45 sec, 37 cycles). PCR products were digested with restriction enzymes and separated in 6% polyacrylamide gel at 4 W for 3 hours and the amplified products were checked for accuracy by sequencing. Positive control for the DNA methylation experiments was human placental genomic DNA treated with the CpG-Methylase M.SssI and the negative control was water. DNA methylation was determined from the polyacrylamide gel pictures in terms of samples showing de-novo appearance of a low MW band, corresponding to a cleaved band at a previously methylated site. The degree of methylation was determined by densitometry in terms of the intensity of the cleaved fragment (lower MW band) relative to the density of the non-methylated plus the methylated bands (lower plus higher MW bands). Densitometry was done as described. Feng et al., (2006) "A truncated $P2X_7$ receptor variant ($P2X_{7-j}$) endogenously expressed in cervical cancer cells antagonizes the full-length $P2X_7$ receptor through hetero-oligomerization" *J Biol Chem* 281:17228-17237.

To confirm the efficacy of the bisulfate method for converting genomic DNA cytosines (but not methylcytosines) to uracils, bisulfate-treated genomic DNA was amplified with primers for Segments 1 and 2. PCR products were purified with PCR purification kit (QIAGEN) and cloned into vector pCR II-TOPO (Invitrogen). Subclones were transformed into *E-Coli* bacteria type BL21 and cultured overnight at 37° C. Plasmid-containing PCR products were extracted with mini-prep kit (Promega) and sequenced. The results (not shown) confirmed that all genomic DNA cytosines converted to uracils, except methylcytosines.

Data Analysis

Data were analyzed using GraphPad Instat (GraphPad Software Inc., San-Diego, Calif.). Significance of differences between groups was estimated by t-test, or by one-way or two-way ANOVA with Tukey-Kramer Multiple Comparisons post test analysis.

Supplies

All chemicals, unless specified otherwise, were obtained from Sigma Chemicals (St. Louis, Mo.).

ALPHABETIZED REFERENCES

Agarwal M K, Iqbal M, Athar M (2005). Inhibitory effect of 18beta-glycyrrhetinic acid on 12-O-tetradecanoyl phorbol-13-acetate-induced cutaneous oxidative stress and tumor promotion in mice. *Redox Rep* 10: 151-157.

Aggarwal B B, Rath P C (1999). TNF-induced signaling in apoptosis. *J Clin Immunol* 19: 350-364.

Bobanovic L K, Royle S J, Murrell-Lagnado R D (2002). P2X receptor trafficking in neurons is subunit specific. *J Neurosci* 22: 4814-4824.

Buell G, Collo G, Rassendren F (1996). P2X receptors: an emerging channel family. *Eur J Neurosci* 8: 2221-2228.

Burnstock G (2006). Purinergic signaling: an overview. *Novartis Found Symp* 276: 26-57.

Dubyak G R, el-Moatassim C (1993). Signal transduction via P2-purinergic receptors for extracellular ATP and other nucleotides. *Am J Physiol* 265: C577-C606.

Feng Y H, Wang L, Wang Q, Li X, Zeng R, Gorodeski G I (2005). ATP ligation stimulates GRK-3-mediated phosphorylation and β-arrestin-2- and dynamin-dependent internalization of the $P2X_7$-receptor. *Am J Physiol* 288: C1342-C1356.

Feng Y H, Li X, Wang L, Zhou L, Gorodeski G I (2006). A truncated $P2X_7$ receptor variant ($P2X_{7-j}$) endogenously expressed in cervical cancer cells antagonizes the full-length $P2X_7$ receptor through hetero-oligomerization. *J Biol Chem* 281: 17228-17237.

Ferrari D, Chiozzi P, Falzoni S, Dal Susino M, Melchiorri L, Baricordi O R, et al (1997a). Extracellular ATP triggers IL-1β release by activating the purinergic P2Z receptor of human macrophages. *J Immunol* 159: 1451-1458.

Ferrari D, Wesselborg S, Bauer M K, Schulze-Osthoff K (1997b). Extracellular ATP activates transcription factor NF-κB through the P2Z purinoreceptor by selectively targeting NF-κB p65. *J Cell Biol* 139: 1635-1643.

Fu W, Cockerell C J (2003). The actinic (solar) keratosis: A $21^{st}$ century perspective. *Arch Dermatol* 139: 66-70.

Gasser S, Raulet D (2006). The DNA damage response, immunity and cancer. *Semin Cancer Biol* 16: 344-347.

Georgiou J G, Skarratt K K, Fuller S J, Martin C J, Christopherson R I, Wiley J S, et al (2005). Human epidermal and monocyte-derived langerhans cells express functional P2X receptors. J Invest Dermatol 125: 482-490.

Glick A, Ryscavage A, Perez-Lorenzo R, Hennings H, Yuspa S, Darwiche N (2007). The high-risk benign tumor: evidence from the two-stage skin cancer model and relevance for human cancer. *Mol Carcinogenesis* 46: 605-610.

Grahames C B A, Michel A D, Chessell I P, Humphrey D P A (1999). Pharmacological characterization of ATP- and LPS-induced IL-1β release in human monocytes. *Br J Pharmacol* 127: 1915-1921.

Greig A V, Linge C, Terenghi G, McGrouther D A, Burnstock G (2003a). Purinergic receptors are part of a functional signaling system for proliferation and differentiation of human epidermal keratinocytes. *J Invest Dermatol* 120: 1007-1015.

Greig A V, Linge C, Healy V, Lim P, Clayton E, Rustin M H, et al (2003b). Expression of purinergic receptors in non-melanoma skin cancers and their functional roles in A431 cells. *J Invest Dermatol* 121: 315-327.

Greig A V, Linge C, Cambrey A, Burnstock G (2003c). Purinergic receptors are part of a signaling system for keratinocyte proliferation, differentiation, and apoptosis in human fetal epidermis. *J Invest Dermatol* 121: 1145-1149.

Gu B J, Zhang W Y, Bendall L J, Chessell I P, Buell G N, Wiley J S (2000). Expression of P2X7 purinoceptors on human lymphocytes and monocytes: evidence for nonfunctional P2X7 receptors. *Am J Physiol* 279: C1189-C1197.

Guerra A N, Fisette P L, Pfeiffer Z A, Quinchia-Rios B H, Prabhu U, Aga M, et al (2003). Purinergic receptor regulation of LPS-induced signaling and pathophysiology. *J Endotoxin Res* 9:256-263.

Guo H, Miao H, Gerber L, Singh J, Denning M F, Gilliam A C, et al (2006). Disruption of EphA2 receptor tyrosine kinase leads to increased susceptibility to carcinogenesis in mouse skin. *Cancer Res* 66: 7050-7058.

Henriksen K L, Novak I (2003). Effect of ATP on intracellular pH in pancreatic ducts involves P2X7 receptors. *Cell Physiol Biochem* 13: 93-102.

Humphreys B J, Rice J, Kertesy S B, Dubyak G R (2000). Stress-activated protein kinase/JNK activation and apoptotic induction by the macrophage P2X7 nucleotide receptor. *J Biol Chem* 275: 26792-26798.

Inoue K, Hosoi J, Denda M (2007). Extracellular ATP has stimulatory effects on the expression and release of IL-6 via purinergic receptors in normal human epidermal keratinocytes. *J Invest Dermatol* 127:362-371.

Khakh B S, Burnstock G, Kennedy C, King B F, North R A, Seguela P, et al (2001). Current status of the nomenclature and properties of P2X receptors and their subunits. *Pharmacol Rev* 53: 107-118.

Kujoth G C, Leeuwenburgh C, Prolla T A (2006). Mitochondrial DNA mutations and apoptosis in mammalian aging. *Cancer Res* 66: 7386-7389.

Li G H, Lee E M, Blair D, Holding C, Poronnik P, Cook D I, et al (2000). The distribution of P2X receptor clusters on individual neurons in sympathetic ganglia and their redistribution on agonist activation. *J Biol Chem* 275:29107-29112.

Li X, Zhou L, Feng Y H, Abdul-Karim F, Gorodeski G I (2006). The $P2X_7$ Receptor: A novel biomarker of uterine epithelial cancers. Cancer Epidemiol Biomarkers Prevention 15: 1-8.

Li X, Qi X, Zhou L, Catera D, Rote N S, Potashkin J, et al (2007). Decreased expression of $P2X_7$ in endometrial epithelial pre-cancerous and cancer cells. *Gynecol Oncology* 106: 233-243.

Lindeque B G (2005). Management of cervical premalignant lesions. *Best Pract Res Clin Obstet Gynaecol* 19: 545-561.

Loomis, W H., Namiki, S, Ostrom R S, Insel P A, Junger W G (2003). Hypertonic stress increases T-cell Interleukin-2 expression through a mechanism that involves ATP release, P2 Receptor, and p38 MAPK activation. *J Biol Chem* 278: 4590-4596.

Mutini C, Falzoni S, Ferrari D, Chiozzi P, Morelli A, Baricordi O R, et al (1999). Mouse dendritic cells express the P2X7 purinergic receptor: Characterization and possible participation in antigen presentation. *J Immunol* 163:1958-1965.

Pastore S, Mascia F, Gulinelli S, Forchap S, Dattilo C, Adinolfi E, et al (2007). Stimulation of purinergic receptors modulates chemokine expression in human keratinocytes. *J Invest Dermatol* 127:660-667.

Ralevic V, Burnstock G (1998). Receptors for purines and pyrimidines. *Pharmacol Rev* 50: 413-492.

Reibel J (2003). Prognosis of oral pre-malignant lesions: Significance of clinical, histopathological, and molecular biological characteristics. *Crit Rev Oral Biol Med* 14: 47-62.

Rodriguez-Nieto S, Zhivotovsky B (2006). Role of alterations in the apoptotic machinery in sensitivity of cancer cells to treatment. *Curr Pharm Des* 12: 4411-4425.

Slater M, Barden J A (2005). Differentiating keratoacanthoma from squamous cell carcinoma by the use of apoptotic and cell adhesion markers. *Histopathology* 47: 170-178.

Soto F, Garcia-Guzman M, Stuhmer W (1997). Cloned ligand-gated channels activated by extracellular ATP (P2X receptors). *J Membr Biol* 160: 91-100.

Sperlágh B, Haskó G, Németh Z, Vizi E S (1998). ATP released by LPS increases nitric oxide production in raw 264.7 macrophage cell line via P2Z/P2X7 receptors. *Neurochem Int* 33: 209-215.

Surprenant A, Rassendren F, Kawashima E, North R A, Buell G (1996). The cytolytic P2Z receptor for extracellular ATP identified as a P2X receptor (P2X7). *Science* 272: 735-738.

Virginio C, MacKenzie A, North R A, Surprenant A (1999). Kinetics of cell lysis, dye uptake and permeability changes in cells expressing the rat P2X7 receptor. *J Physiol* 519: 335-346.

Wang Q, Wang L, Feng Y H, Li X, Zeng R, Gorodeski G I (2004a). $P2X_7$-receptor mediated apoptosis of human cervical epithelial cells. *Am J Physiol* 287: C1349-C1358.

Wang Q, Li X, Wang L, Feng Y H, Zeng R, Gorodeski G I (2004b). Anti-apoptotic effects of estrogen in normal and in cancer human cervical epithelial cells. *Endocrinology* 145: 5568-5579.

Wang L, Feng Y H, Gorodeski G I (2005). EGF facilitates epinephrine inhibition of $P2X_7$-receptor mediated pore formation and apoptosis: a novel signaling network. *Endocrinology* 146: 164-174.

White N, Butler P E M, Burnstock G (2005). Human melanomas express functional P2X7 receptors. *Cell Tissue Res* 321: 411-418.

Woodworth C D, Michael E, Smith L, Vijayachandra K, Glick A, Hennings H, et al (2004). Strain-dependent differences in malignant conversion of mouse skin tumors is an inherent property of the epidermal keratinocyte. *Carcinogenesis* 25: 1771-1778.

Zhu L, Li X, Zeng R, Gorodeski G I (2006). Changes in Tight Junctional Resistance of the Cervical Epithelium are Associated with Modulation of Content and Phosphorylation of Occludin 65 KDa and 50 KDa forms. *Endocrinology* 147: 977-989.

NUMBERED REFERENCES

1. Croker A K, Allan A L: Cancer stem cells: implications for the progression and treatment of metastatic disease. J Cell Mol Med 2008; 12:374-90
2. Rodriguez-Nieto S, Zhivotovsky B: Role of alterations in the apoptotic machinery in sensitivity of cancer cells to treatment. Curr Pharm Des 2006; 12:4411-25
3. Wyllie A H, Kerr J F R, Currie A R. Cell death: the significance of apoptosis. Int Rev Cytol 1980; 68:251 306

4. Ellis H M, Yuan J, Horvitz H R. Mechanisms and functions of cell death. Annul Rev Cell Biol 1991; 7:663 98
5. Fawthrop D J, Boobis A R, Davies D S. Mechanisms of cell death. Arch Toxicol 1991; 65:437-44
6. Soti C, Sreedhar A S, Csermely P. Apoptosis, necrosis and cellular senescence: chaperone occupancy as a potential switch. Aging Cell 2003; 2:39-45
7. Gasser S, Raulet D. The DNA damage response, immunity and cancer. Semin Cancer Biol 2006; 16:344-7
8. Kujoth G C, Leeuwenburgh C, Prolla T A. Mitochondrial DNA mutations and apoptosis in mammalian aging. Cancer Res 2006; 66:7386-9
9. Rodriguez-Nieto S, Zhivotovsky B. Role of alterations in the apoptotic machinery in sensitivity of cancer cells to treatment. Curr Pharm Des 2006; 12:4411-25
10. Hanahan D, Weinberg R A. The hallmarks of cancer. Cell 2000; 100:57-70
11. Cummings J, Ward T H, Ranson M, et al. Apoptosis pathway-targeted drugs: from the bench to the clinic. Biochim Biophys Acta 2004; 1705:53-66
12. Schmitt C A. Senescence, apoptosis and therapy: cutting the lifelines of cancer. Nat Rev Cancer 2003; 3:286-95
13. Ziegler D S, Kung A L. Therapeutic targeting of apoptosis pathways in cancer. Curr Opin Oncol 2008; 20:97-103
14. Boatright K M, Salvesen G S. Mechanisms of caspase activation. Curr Opin Cell Biol 2003; 15:725-31
15. Klein S, McCormick F, Levitzki A. Killing time for cancer cells. Nat Rev Cancer 2005; 5:573-580
16. Lorenzo H K, Susin S A. Therapeutic potential of AIF-mediated caspase independent programmed cell death. Drug Resist Updates 2007; 10:235-55
17. Degterev A, Boyce M, Yuan J. A decade of caspases. Oncogene 2003; 22:8543-67
18. Guo B, Godzik A, Reed J C. Bcl-G, a novel pro-apoptotic member of the Bcl-2 family. J Biol Chem 2001; 276:2780-5
19. Antonsson B, Martinou J C. The Bcl-2 protein family. Exp Cell Res 2000; 256:50-7
20. Green D R. Apoptotic pathways: ten minutes to dead. Cell 2005; 121:671-4
21. Oliver L, Vallette F M. The role of caspases in cell death and differentiation. Drug Resist Updates 2005; 8:163-70
22. Iannolo G, Conticello C, Memeo L, De Maria R. Apoptosis in normal and cancer stem cells. Crit. Rev Oncol Hematol 2008; 66:42-51
23. Nachmias B, Ashhab Y, Ben-Yehuda D. The inhibitor of apoptosis protein family (IAPs): an emerging therapeutic target in cancer. Semin Cancer Biol 2004; 14:231-43
24. Reed J C. Drug Insight: cancer therapy strategies based on restoration of endogenous cell death mechanisms. Nature Clin Practice Oncol 2006; 3:388-98
25. Qiao L, Wong B C Y. Targeting apoptosis as an approach for gastrointestinal cancer therapy. Drug Resistance Updates 2009; 12:55-64
26. Thorburn A, Behbakht K, Ford H. TRAIL receptor-targeted therapeutics: resistance mechanisms and strategies to avoid them. Drug Resist Updates 2008; 11:17-24
27. Kucharczak J, Simmons M J, Fan Y, Gelinas C. To be, or not to be: NF-kB is the answer-role of Rel/NF-kB in the regulation of apoptosis. Oncogene 2003; 22:8961-82
28. Ghobrial I M, Witzig T E, Adjei A A. Targeting Apoptosis Pathways in Cancer Therapy. CA Cancer J Clin 2005; 55; 178-94
29. Li Q X, Yu D H, Liu G, et al. Selective anticancer strategies via intervention of the death pathways relevant to cell transformation Cell Death and Differentiation 2008; 15:1197-210
30. Gore S D, Jones C, Kirkpatrick P. Decitabine. Nat. Rev Drug Discov 2006; 5:891-2
31. Reu F J, Bae S I, Cherkassky L, et al. Overcoming resistance to interferon-induced apoptosis of renal carcinoma and melanoma cells by DNA demethylation. J Clin Oncol 2006; 24:3771-9
32. Gartel A L. Transcriptional inhibitors, p53 and apoptosis. Biochim Biophys Acta 2008; 1786:83-6
33. Cornett W R, McCall L M, Petersen R P, et al. Randomized multicenter trial of hyperthermic isolated limb perfusion with melphalan alone compared with melphalan plus tumor necrosis factor: American College of Surgeons Oncology Group Trial Z0020. J Clin Oncol 2006; 24:4196-201
34. Jo M, Kim T H, Seol D W, et al. Apoptosis induced in normal human hepatocytes by tumor necrosis factor-related apoptosis-inducing ligand. Nat Med 2000; 6:564-7
35. Wang S, El-Deiry W S. TRAIL and apoptosis induction by TNF-family death receptors. Oncogene 2003; 22:8628-33
36. Rigaud S, Fondaneche M C, Lambert N, et al. XIAP deficiency in humans causes an X-linked lymphoproliferative syndrome. Nature 2006; 444:110-4
37. Renvoize C, Biola A, Pallardy M, Breard J. Apoptosis: identification of dying cells. Cell Biol Toxicol 1998; 14:111-20
38. Wang Q, Wang L, Feng Y H, et al. P2X7-receptor mediated apoptosis of human cervical epithelial cells. Am J Physiol 2004; 287:C1349-58
39. Li X, Zhou L, Feng Y H, et al. The P2X7 Receptor: A novel biomarker of uterine epithelial cancers. Cancer Epidemiol Biomarkers Preven 2006; 15:1-8
40. Wang Q, Li X, Wang L, et al. Anti-apoptotic effects of estrogen in normal and in cancer human cervical epithelial cells. Endocrinology 2004; 145:5568-79
41. Wang L, Feng Y H, Gorodeski G I. Epidermal Growth factor facilitates epinephrine inhibition of P2X7-receptor mediated pore formation and apoptosis: a novel signaling network. Endocrinology 2005; 146:164-74
42. Feng Y H, Wang L, Wang Q, et al. ATP stimulates GRK-3 phosphorylation and b-arrestin-2-dependent internalization of P2X7-receptor. Am J Physiol 2005; 288:C1342-56
43. Buell G N, Talabot F, Gos A, et al. Gene structure and chromosomal localization of the human P2X7 receptor. Receptors Channels 1998; 5:347-54
44. Zhou L, Luo L, Qi X, et al. Regulation of P2X7 gene transcription. Purinergic Signal 2009; 5:409-426
45. Kim M, Jiang L H, Wilson H L, et al. Proteomic and functional evidence for a P2X7 receptor signalling complex. EMBO J. 2001; 20:6347-58
46. Dubyak G R, el-Moatassim C. Signal transduction via P2-purinergic receptors for extracellular ATP and other nucleotides. Am J Physiol 1993; 265:C577-606
47. Ralevic V, Burnstock G. Receptors for purines and pyrimidines. Pharmacol Rev 1998; 50:413-92
48. North R A. Molecular physiology of P2X receptors. Physiol Rev 2002; 82:1013-67
49. Surprenant A, North R A. Signaling at Purinergic P2X Receptors. Annu Rev Physiol 2009; 71:333-59
50. Feng Y H, Li X, Wang L, et al. A truncated P2X7 receptor variant (P2X7-j) endogenously expressed in cervical cancer cells antagonizes the full-length P2X7 receptor through hetero-oligomerization. J Biol Chem 2006; 281:17228-37
51. Boldt W, Klapperstuck M, Buttner C, et al. Glu496Ala polymorphism of human P2X7 receptor does not affect its electrophysiological phenotype. Am J Physiol 2003; 284:C749-56

52. Surprenant A, Rassendren F, Kawashima E, et al. The cytolytic P2Z receptor for extracellular ATP identified as a P2X receptor (P2X7). Science 1996; 272:735-8.
53. Denlinger L C, Sommer J A, Parker K, et al. Mutation of a dibasic amino acid motif within the C-terminus of the P2X7 nucleotide receptor results in trafficking defects and impaired function. J Immunol 2003; 171:1304-11
54. Cheewatrakoolpong B, Gilchrest H, Anthes J C, Greenfeder S. Identification and characterization of splice variants of the human P2X7 ATP channel. Biochem Biophys Res Comm 2005; 332:17-27
55. Fu W, McCormick T, Qi X, et al. Activation of P2X(7)-mediated apoptosis Inhibits DMBA/TPA-induced formation of skin papillomas and cancer in mice. BMC Cancer 2009; 9:114
56. Sperlágh B, Haskó G, Németh Z, Vizi E S. ATP released by LPS increases nitric oxide production in raw 264.7 macrophage cell line via P2Z/P2X7 receptors. Neurochem Int 1998; 33:209-15
57. Grahames C B A, Michel A D, Chessell I P, Humphrey D P A. Pharmacological characterization of ATP- and LPS-induced IL-1b release in human monocytes. Br J Pharmacol 1999; 127:1915-21
58. Henriksen K L, Novak I. Effect of ATP on intracellular pH in pancreatic ducts involves P2X7 receptors. Cell Physiol Biochem 2003; 13:93-102
59. Loomis W H, Namiki S, Ostrom R S, et al. Hypertonic stress increases T-cell Interleukin-2 expression through a mechanism that involves ATP release, P2 Receptor, and p38 MAPK activation. J Biol Chem 2003; 278:4590-6
60. Mitchell C H, Lu W, Hu H, et al. The P2X7 receptor in retinal ganglion cells: A neuronal model of pressure-induced damage and protection by a shifting purinergic balance. Purinergic Signal 2009; 5:241-9 (DOI 10.1007/s11302-009-9142-6)
61. Yegutkin G G. Nucleotide- and nucleoside-converting ectoenzymes: Important modulators of purinergic signalling cascade. Biochim Biophys Acta 2008; 1783:673-94
62. Hübschmann M V, Skladchikova G. The Role of ATP in the Regulation of NCAM Function. Neurochem Res Jul. 8, 2008 DOI 10.1007/s11064-008-9769-7
63. Ferrari D, Chiozzi P, Falzoni S, et al. Extracellular ATP triggers IL-1β release by activating the purinergic P2Z receptor of human macrophages. J Immunol 1997; 159: 1451-8
64. Aggarwal B B, Rath P C. TNF-induced signaling in apoptosis. J Clin Immunol 1999; 19:350-64
65. Humphreys B J, Rice J, Kertesy S B, Dubyak G R. Stress-activated protein kinase/JNK activation and apoptotic induction by the macrophage P2X7 nucleotide receptor. J Biol Chem 2000; 275:26792-8
66. Ferrari D, Wesselborg S, Bauer M K, Schulze-Osthoff K. Extracellular ATP activates transcription factor NF-κB through the P2Z purinoreceptor by selectively targeting NF-κB p65. J Cell Biol 1997; 139:1635-43
67. Petrou S, Ugur M, Drummond R M, et al. P2X7 purinoceptor expression in *Xenopus* oocytes is not sufficient to produce a pore-forming P2Z-like receptor. FEBS Lett 1997; 411:339-45
68. Schilling W P, Wasylyna T, Dubyak G R, et al. Maitotoxin and P2Z/P2X7 purinergic receptors stimulation activate a common cytolytic pore. Am J Physiol 1999; 277:C766-76
69. Klapperstuck M, Buttner C, Bohm T, et al. Characteristics of P2X7 receptors from human B lymphocytes expressed in *Xenopus* oocytes. Biochim Biophys Acta 2000; 1467:444-56
70. Locovei S, Scemes E, Qiu F, et al. Pannexin1 is part of the pore forming unit of the P2X7R death complex. FEBS Lett 2007; 581:483-8
71. Iglesias R, Locovei S, Roque A, et al. P2X7 receptor-Pannexin1 complex: Pharmacology and signaling. Am J Physiol 2008; 295:C752-60
72. Pelegrin P, Surprenant A. The P2X7 receptor-pannexin connection to dye uptake and IL-1β release. Purinergic Signal 2009; 5:129-37 (DOI 10.1007/s11302-009-9141-7).
73. Ma W, Korngreen A, Weil S, et al. Pore properties and pharmacological features of the P2X receptor channel in airway ciliated cells. J Physiol 2006; 571:503-17
74. Guo C, Masin M, Qureshi O S, Murrell-Lagnado R D. Evidence for Functional P2X4/P2X7 Heteromeric Receptors. Mol Pharmacol 2007; 72:1447-56
75. Boumechache M, Masin M, Edwardson J M, et al. Analysis of Assembly and Trafficking of Native P2X4 and P2X7 Receptor Complexes in Rodent Immune Cells. J Biol Chem 2009; 284:13446-54
76. Greig A V, Linge C, Healy V, et al. Expression of purinergic receptors in non-melanoma skin cancers and their functional roles in A431 cells. J Invest Dermatol 2003; 121:315-27
77. Lee H Y, Bardini M, Burnstock G. Distribution of P2X receptors in the urinary bladder and the ureter of the rat. J Urol 2000; 163:2002-7
78. Menzies J, Paul A, Kennedy C. P2X7 subunit-like immunoreactivity in the nucleus of visceral smooth muscle cells of the guinea pig. Autonomic Neuroscience: Basic and Clinical 2003; 106:103-9
79. Franke H, Gunther A, Grosche J, et al. P2X7 receptor expression after ischemia in the cerebral cortex of rats. J Neuropathol Exp Neurol 2004; 636:86-99
80. Jiang L H, Kim M, Spelta V, et al. Subunit Arrangement in P2X Receptors. J Neurosc 2003; 23:8903-10
81. Li X, Gorodeski G I. Apically sorted P2X7 receptors mediate purinergic-induced pore formation preferentially in apical domains of the plasma membrane. Nucleosides Nucleotides and Nucleic Acids 2006; 25:1045-9
82. Li X, Qi X, Zhou L, et al. P2X7 receptor expression is decreased in epithelial cancer cells of ectodermal, urogenital sinus, and distal paramesonephric-duct origin. Purinergic Signal 2009; 5:351-368
83. Li M, Luo J, Brooks C L, Gu W. Acetylation of p53 inhibits its ubiquitination by Mdm2. J Biol Chem 2002; 277:50607-11
84. Yang S H, Sharrocks A D. Convergence of the SUMO and MAPK pathways on the ETS-domain transcription factor Elk-1. Biochem Soc Symp 2006; 73:121-9
85. Yang Q, Kardava L, St Leger A, et al. E47 controls the developmental integrity and cell cycle quiescence of multipotential hematopoietic progenitors. J Immunol 2008; 181:5885-94
86. Mathis D J, Elkaim R, Kedinger C, et al. Specific in vitro initiation of transcription on the adenovirus type 2 early and late EII transcription units. Proc Natl Acad Sci USA 1981; 78:7383-7
87. Hamel P A, Gill R M, Phillips R A, Gallie B L. Transcriptional repression of the E2-containing promoters EIIaE, c-myc, and RB1 by the product of the RB1 gene. Mol Cell Biol 1992; 12:3431-8
88. Zheng N, Fraenkel E, Pabo C O, Pavletich N P. Structural basis of DNA recognition by the heterodimeric cell cycle transcription factor E2FDP. Genes Dev 1999; 13:666-74
89. Pardee A B, Li C J, Reddy G P. Regulation in S phase by E2F: Cell Cycle 2004; 3:1091-4

90. Laptenko O, Prives C. Transcriptional regulation by p53: one protein, many Possibilities. Cell Death and Differentiation 2006; 13:951-61
91. Turner C M, Tam F W K, Lai P C, et al. Increased expression of the pro-apoptotic ATP-sensitive P2X7 receptor in experimental and human glomerulonephritis. Nephrol Dial Transplant 2007; 22:386-95
92. Schulze-Lohoff E, Hugo C, Rost S, et al. Extracellular ATP causes apoptosis and necrosis of cultured mesangial cells via P2Z/P2X7 receptors. Am J Physiol 1998; 275: F962-71
93. Zhou L, Qi X, Luo L, et al. Poly(ADP-ribose) polymerase (PARP) decreases apoptosis and stimulates growth of HeLa cells by decreasing stability of P2X7 mRNA. The 99th AACR Annual Meeting, Apr. 12-16, 2008; San Diego, Calif. (Experimental Therapy 2: Abstract #2692). http://www.aacrmeetingabstracts.org/cgi/content/meeting_abstract/2008/1_Annual_Meeting/2692?maxtoshow=&HITS=10&hits=10&RESULTFORMAT=&author1=gorodeski&andorexactfulltext=and&searchid=1&FIRSTINDEX-0&sortspec=relevance&resourcetype=HWCIT
94. Zhou L, Qi X, Potashkin J A, et al. Micro-RNAs miR-186 and miR-150 down-regulate expression of the pro-apoptotic purinergic P2X7 receptor by activation of instability sites at the 3'-untranslated region of the gene that decrease steady-state levels of the transcript. J Biol Chem 2008; 283:28274-86
95. Lu J, Getz G, Miska E A, et al. MicroRNA expression profiles classify human cancers. Nature 2005; 435:834-8
96. Cheng A M, Byrom M W, Shelton J, Ford L P. Antisense inhibition of human miRNAs and indications for an involvement of miRNA in cell growth and apoptosis. Nucleic Acids Res 2005; 33: 1290-7
97. Georgiou J G, Skarratt K K, Fuller S J, et al. Human epidermal and monocyte-derived langerhans cells express functional P2X receptors. J Invest Dermatol 2005; 125: 482-90
98. Chen L, Brosnan C F. Regulation of immune response by P2X7 receptor. Crit. Rev Immunol 2006; 26:499-513
99. Lenertz L Y, Gavala M L, Hill L M, Bertics P J. Cell signaling via the P2X7 nucleotide receptor: linkage to ROS production, gene transcription, and receptor trafficking. Purinergic Signal 2009; 5:175-87 (DOI 10.1007/s11302-009-9133-7)
100. Sperlágh B, Vizi E S, Wirkner K, Illes P. P2X7 receptors in the nervous system. Prog Neurobiol 2006; 78:327-46
101. Li J, Meyer R, Duncan R L, Turner C H. P2X7 nucleotide receptor plays an important role in callus remodeling during fracture repair. Calcified Tissue International 2009; 84:405-12
102. Nakamoto T, Brown D A, Catalan M A, et al. Purinergic P2X7 receptors mediate ATP-induced saliva secretion by the mouse submandibular gland. J Biol Chem 2009; 284: 4815-22
103. Qu Y, Dubyak G R. P2X7 receptors regulate multiple types of membrane trafficking responses and non-classical secretion pathways. Purinergic Signal. 2009; 5:163-7 DOI 10.1007/s11302-009-9132-8
104. Li X, Qi X, Zhou L, et al. Decreased expression of P2X7 in endometrial epithelial pre-cancerous and cancer cells. Gynecol Oncology 2007; 106:233-43
105. Eckert R L, Crish J F, Robinson N A. The epidermal keratinocyte as a model for the study of gene regulation and cell differentiation. Physiol Rev 1997; 77:397-424
106. Solini A, Cuccato S, Ferrari D, et al. Increased P2X7 receptor expression and function in thyroid papillary cancer: A new potential marker of the disease? Endocrinology 2008; 149:389-96
107. Tryndyak V, Kovalchuk O, Pogribny I P. Identification of differentially methylated sites within unmethylated DNA domains in normal and cancer cells. Anal Biochem 2006; 356:202-7
108. Sibilia M, Kroismayr R, Lichtenberger B M, et al. The epidermal growth factor receptor: from development to tumorigenesis. Differentiation 2007; 75:770-87
109. Song S H, Lee J K, Oh M J, et al. Risk factors for the progression or persistence of untreated mild dysplasia of the uterine cervix. Int J Gynecol Cancer 2006; 16:1608-13
110. Romagnoli R, Baraldi P G, Cruz-Lopez O, et al. The P2X7 receptor as a therapeutic target. Expert Opin Ther Targets 2008; 12:647-61
111. Rapaport E. Treatment of human tumor cells with ADP or ATP yields arrest of growth in the S phase of the cell cycle. J Cell Physiol 1983; 114:279-83
112. Agteresch H J, Dagnelie P C, van der Gaast A, et al. Randomized clinical trial of adenosine 5'-triphosphate in patients with advanced non-small-cell lung cancer. J Natl Cancer Inst 2000; 92: 321-8
113. Agteresch H J, Burgers S A, van der Gaast A, et al. Randomized clinical trial of adenosine 5'-triphosphate on tumor growth and survival in advanced lung cancer patients. Anticancer Drugs 2003; 14:639-44
114. Agteresch H J, Rietveld T, Kerkhofs L G, et al. Beneficial effects of adenosine triphosphate on nutritional status in advanced lung cancer patients: a randomized clinical trial. J Clin Oncol 2002; 20:371-8
115. Leij-Halfwerk S, Agteresch H J, Sijens P E, Dagnelie P C. Adenosine triphosphate infusion increases liver energy status in advanced lung cancer patients: an in vivo 31P magnetic resonance spectroscopy. Hepatology 2002; 35:421-4
116. White N, Burnstock G. P2 receptors and cancer. Trends Pharmacol Sci 2006; 27:211-7
117. Di Virgilio F, Ferrari D, Adinolfi E. P2X7: a growth-promoting receptor—implications for cancer. Purinergic Signal 2009; 5:251-256 (DOI 10.1007/s11302-009-9145-3)
118. Matsuoka I, Ohkubo S. ATP- and adenosine-mediated signaling in the central nervous system: adenosine receptor activation by ATP through rapid and localized generation of adenosine by ecto-nucleotidases. J Pharmacol Sci 2004; 94:95-9
119. Shabbir M, Burnstock G. Purinergic receptor-mediated effects of adenosine 5'-triphosphate in urological malignant diseases. Int J Urol 2009; 16:143-50
120. Shabbir M, Thompson C, Jarmulowiczc M, et al. Effect of extracellular ATP on the growth of hormone-refractory prostate cancer in vivo. BJU Int 2008; 102:108-12
121. Shabbir M, Ryten M, Thompson C, et al. Purinergic receptor-mediated effects of ATP in high-grade bladder cancer. BJU Int 2008; 101:106-12
122. Williams N, Coleman P S. Exploring the adenine nucleotide binding sites on mitochondrial F1-ATPase with a new photoaffinity probe, 3'-O-(4-Benzoyl)benzoyl Adenosine 5'-Triphosphate. J Biol Chem 1982; 257:2834-41
123. Michel A D, Xing M, Humphrey P P A. Serum constituents can affect 2'-& 3'-O-(4-benzoylbenzoyl)-ATP potency at P2X7 receptors. Brit J Pharmacol 2001; 132:1501-8
124. Armstrong 1N, Brust T B, Lewis R G, MacVicar B A. Activation of presynaptic P2X7-Like receptors depresses 125. Boyer J L, Romero-Avila T, Schachter J B, Harden T K. Identification of competitive antagonists of the P2Y1 receptor. Mol Pharmacol 1996; 50:1323-9
126. Boyer J L, Harden T K. Irreversible activation of phospholipase C-coupled P2Y-purinergic receptors by 3'-O-(4-benzoyl)benzoyl adenosine 5'-triphosphate. Mol Pharmacol 1989; 39:831-5
127. Vigne P, Hechler B, Gachet C, et al. Benzoyl ATP Is an Antagonist of Rat and Human P2Y1 Receptors and of Platelet Aggregation. Biochem Biophys Res Comm 1999; 256:94-7
128. Blanchard D K, Hoffmann S L, Djeu J Y Inhibition of extracellular ATP-mediated lysis of human macrophages by calmodulin antagonists. J Cell Biochem 1995; 57:452-64
129. Bianchi B R, Lynch K J, Touma E, et al. Pharmacological characterization of recombinant human and rat P2X receptor subtypes. Eur J Pharmacol 1999; 376:127-38
130. Kukley M, Stausberg P, Adelmann G, et al. Ecto-nucleotidases and nucleoside transporters mediate activation of adenosine receptors on hippocampal mossy fibers by P2X7 receptor agonist 2'-3'-O-(4-benzoylbenzoyl)-ATP. J Neuroscience 2004; 24:7128-39
131. Baraldi P G, Di Virgilio F, Romagnoli R. Agonists and antagonists acting at P2X7 receptor. Curr Top Med. Chem. 2004; 4:1707-17
132. Glick A, Ryscavage A, Perez-Lorenzo R, et al. The high-risk benign tumor: evidence from the two-stage skin cancer model and relevance for human cancer. Mol Carcinogenesis 2007; 46:605-10
133. Woodworth C D, Michael E, et al. Strain-dependent differences in malignant conversion of mouse skin tumors is an inherent property of the epidermal keratinocyte. Carcinogenesis 2004; 25:1771-8
134. Reibel J: Prognosis of oral pre-malignant lesions: Significance of clinical, histopathological, and molecular biological characteristics. Crit. Rev Oral Biol Med 2003; 14:47-62
135. Fu W, Cockerell C J: The actinic (solar) keratosis: A 21st century perspective. Arch Dermatol 2003; 139:66-70
136. Lindeque B G: Management of cervical premalignant lesions. Best Pract Res Clin Obstet Gynaecol 2005; 19:545-61.

We claim:

1. A method for inducing apoptosis in malignant cancer cells, comprising:
   a) providing:
      i) a subject comprising a plurality of malignant cancer cells, wherein said cancer cells comprise a $P2X_7$ receptor;
      ii) a composition comprising a compound that pharmacologically activates $P2X_7$ mediated apoptosis in said cancer cells;
   b) administering said composition locally to said cancer cells under conditions such that apoptosis is induced.

2. The method of claim 1, wherein said compound comprises benzoylbenzoyl adenosine triphosphate (BzATP).

3. The method of claim 1, wherein said apoptosis kills said cancer cell.

4. The method of claim 1, wherein said local administering comprises using a medical device selected from the group consisting of a transdermal patch, a catheter, an applicator gun, and a syringe.

5. The method of claim 1, wherein said composition further comprises TNFα.

6. The method of claim 1, wherein said plurality of cancer cells are derived from epithelial cells.

7. The method of claim 1, wherein said plurality of cancer cells are selected from the group consisting of epidermal cancer cells and squamous cell carcinoma cells.

8. A method for inducing apoptosis in malignant epithelial cancer cells, comprising:
   a) providing:
      i) a subject comprising a plurality of malignant epithelial cancer cells;
      ii) a benzoylbenzoyl-adenosine triphosphate $P2X_7$ receptor agonist capable of inducing apoptosis in said cancer cells;
   b) administering said agonist to the surface of said cancer cells under conditions such that apoptosis is induced.

9. The method of claim 8, wherein said apoptosis kills said cancer cell.

10. The method of claim 8, wherein said administering further comprises a medical device.

11. The method of claim 10, wherein said medical device is selected from the group consisting of a transdermal patch, a catheter, an applicator gun and a syringe.

12. The method of claim 8, wherein said administering further comprises TNFα.

13. The method of claim 8, wherein said plurality of epithelial cancer cells are germative epithelial cancer cells.

14. The method of claim 8, wherein said plurality of epithelial cancer cells are selected from the group consisting of epidermal cancer cells and squamous cell carcinoma cells.

* * * * *

SEQUENCE LISTING

```
<160> NUMBER OF SEQ ID NOS: 69

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is aspartate-O-methyl-fluoromethylketone

<400> SEQUENCE: 1

Leu Glu His Xaa
1

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is aspartate-O-methyl-fluoromethylketone

<400> SEQUENCE: 2

Ile Glu Thr Xaa
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Benzyloxy residue
<220> FEATURE:
```

```
<221> NAME/KEY: MISC_FEATURE
<222> LOCATION: (4)..(4)
<223> OTHER INFORMATION: X is aspartate-O-methyl-fluoromethylketone

<400> SEQUENCE: 3

Xaa Val Ala Xaa
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is aspartate-O-methyl-fluoromethylketone

<400> SEQUENCE: 4

Asp Glu Val Xaa
1

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tttcagatgt ggcaattcag                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tatcacatct cgcaatagac                                               20

<210> SEQ ID NO 7
<211> LENGTH: 31
<212> TYPE: DNA
<213> ORGANISM: Artificial Sequence
<220> FEATURE:
<223> OTHER INFORMATION: Synthetic

<400> SEQUENCE: 7
tttttaagct taagatgtga agccaggatc g                                  31

<210> SEQ ID NO 8
<211> LENGTH: 28
<212> TYPE: DNA
<213> ORGANISM: Artificial Sequence
<220> FEATURE:
<223> OTHER INFORMATION: Synthetic

<400> SEQUENCE: 8
tttttaagct tggatcaagc cagctgta                                      28

<210> SEQ ID NO 9
<211> LENGTH: 31
<212> TYPE: DNA
<213> ORGANISM: Artificial Sequence
<220> FEATURE:
```

<223> OTHER INFORMATION: Synthetic

<400> SEQUENCE: 9
tttttaagct tggtggtgtc cctcactgaa t          31

<210> SEQ ID NO 10
<211> LENGTH: 31
<212> TYPE: DNA
<213> ORGANISM: Artificial Sequence
<220> FEATURE:
<223> OTHER INFORMATION: Synthetic

<400> SEQUENCE: 10
tttttaagct tggggctgaa taaagggttg t          31

<210> SEQ ID NO 11
<211> LENGTH: 31
<212> TYPE: DNA
<213> ORGANISM: Artificial Sequence
<220> FEATURE:
<223> OTHER INFORMATION: Synthetic

<400> SEQUENCE: 11
tttttaagct taatgcccat cctctgaaca c          31

<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12
tttttaagct tgccagctgg ggtgaggtca tctg          34

<210> SEQ ID NO 13
<211> LENGTH: 31
<212> TYPE: DNA
<213> ORGANISM: Artificial Sequence
<220> FEATURE:
<223> OTHER INFORMATION: Synthetic

<400> SEQUENCE: 13
tttttaagct ttaggacttg gcgcttcttg t          31

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
tttttaagct tagggcccgc cccaactctg cag          33

<210> SEQ ID NO 15
<211> LENGTH: 35
<212> TYPE: DNA
<213> ORGANISM: Artificial Sequence
<220> FEATURE:
<223> OTHER INFORMATION: Synthetic

<400> SEQUENCE: 15
tttttaagct tagtcattgg aggagcttga agtta          35

<210> SEQ ID NO 16

```
<211> LENGTH: 31
<212> TYPE: DNA
<213> ORGANISM: Artificial Sequence
<220> FEATURE:
<223> OTHER INFORMATION: Synthetic

<400> SEQUENCE: 16 ttttccatg gacaacccttt tattcagccc c                                31

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17 ttttccatg gcacagcaag cccccctccca gta                              33

<210> SEQ ID NO 18
<211> LENGTH: 35
<212> TYPE: DNA
<213> ORGANISM: Artificial Sequence
<220> FEATURE:
<223> OTHER INFORMATION: Synthetic

<400> SEQUENCE: 18 ttttccatg gggtgacagc ctccctccct gcgcg                             35

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19 ttttccatg gcttaccaaa cgtaggaaaa                                   30

<210> SEQ ID NO 20
<211> LENGTH: 31
<212> TYPE: DNA
<213> ORGANISM: Artificial Sequence
<220> FEATURE:
<223> OTHER INFORMATION: Synthetic

<400> SEQUENCE: 20 ttttccatg gcccagatcc cacttaccaa a                                 31

<210> SEQ ID NO 21
<211> LENGTH: 32
<212> TYPE: DNA
<213> ORGANISM: Artificial Sequence
<220> FEATURE:
<223> OTHER INFORMATION: Synthetic

<400> SEQUENCE: 21 ttttccatg gagagcacgt ctcagattcg aa                                32

<210> SEQ ID NO 22
<211> LENGTH: 32
<212> TYPE: DNA
<213> ORGANISM: Artificial Sequence
<220> FEATURE:
<223> OTHER INFORMATION: Synthetic

<400> SEQUENCE: 22
``` ttttccatg ggctgcagcc tggcaccgtt tc                    32

<210> SEQ ID NO 23
<211> LENGTH: 28
<212> TYPE: DNA
<213> ORGANISM: Artificial Sequence
<220> FEATURE:
<223> OTHER INFORMATION: Synthetic

<400> SEQUENCE: 23 ttttccatg gtgcgcgccc tggcgggc                         28

<210> SEQ ID NO 24
<211> LENGTH: 32
<212> TYPE: DNA
<213> ORGANISM: Artificial Sequence
<220> FEATURE:
<223> OTHER INFORMATION: Synthetic

<400> SEQUENCE: 24 ttttccatg gcctgcgctt tcctaccttc cc                    32

<210> SEQ ID NO 25
<211> LENGTH: 36
<212> TYPE: DNA
<213> ORGANISM: Artificial Sequence
<220> FEATURE:
<223> OTHER INFORMATION: Synthetic

<400> SEQUENCE: 25 ttttccatg gtcagatgcc agcatgatca ccaggc                36

<210> SEQ ID NO 26
<211> LENGTH: 39
<212> TYPE: DNA
<213> ORGANISM: Artificial Sequence
<220> FEATURE:
<223> OTHER INFORMATION: Synthetic

<400> SEQUENCE: 26
ggaccaagct tatcgatgtc gactttttt ttttttttt             39

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
ggaccaagct tatcgatgtc gac                             23

<210> SEQ ID NO 28
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' biotin-labeled

<400> SEQUENCE: 28
gctcttggcc ttctgttttg                                 20

<210> SEQ ID NO 29

```
<211> LENGTH: 20
<212> TYPE: DNA
<213> ORGANISM: Artificial Sequence
<220> FEATURE:
<223> OTHER INFORMATION: Synthetic

<400> SEQUENCE: 29
ggtgtagtct gcggtgtcaa                                               20

<210> SEQ ID NO 30
<211> LENGTH: 31
<212> TYPE: DNA
<213> ORGANISM: Artificial Sequence
<220> FEATURE:
<223> OTHER INFORMATION: Synthetic

<400> SEQUENCE: 30
ccgctaagct tgcttgtcac tcaccagagc a                                  31

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
cagtacgttt gtaattgcag ttactg                                        26

<210> SEQ ID NO 32
<211> LENGTH: 26
<212> TYPE: DNA
<213> ORGANISM: Artificial Sequence
<220> FEATURE:
<223> OTHER INFORMATION: Synthetic

<400> SEQUENCE: 32
cagtaactgc aattacaaac gtactg                                        26

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33
gagcttgaag tccaagactc ctg                                           23

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
caggagtctt ggacttcaag ctc                                           23

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
```

```
gccactgcct atacccgccc ca                                              22
```

```
<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
tggggcgggt ataggcagtg gc                                              22
```

```
<210> SEQ ID NO 37
<211> LENGTH: 23
<212> TYPE: DNA
<213> ORGANISM: Artificial Sequence
<220> FEATURE:
<223> OTHER INFORMATION: Synthetic

<400> SEQUENCE: 37
tggcgcttct tgtccatcac agc                                             23
```

```
<210> SEQ ID NO 38
<211> LENGTH: 23
<212> TYPE: DNA
<213> ORGANISM: Artificial Sequence
<220> FEATURE:
<223> OTHER INFORMATION: Synthetic

<400> SEQUENCE: 38
gctgtgatgg acaagaagcg cca                                             23
```

```
<210> SEQ ID NO 39
<211> LENGTH: 31
<212> TYPE: DNA
<213> ORGANISM: Artificial Sequence
<220> FEATURE:
<223> OTHER INFORMATION: Synthetic

<400> SEQUENCE: 39
tttttccatg gcttaccaaa tttaggaaaa g                                    31
```

```
<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
atctctgcag tggcttacag caca                                            24
```

```
<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
tgtgctgtaa gccactgcag agat                                            24
```

```
<210> SEQ ID NO 42
<211> LENGTH: 22
<212> TYPE: DNA
<213> ORGANISM: Artificial Sequence
<220> FEATURE:
```

-continued

<223> OTHER INFORMATION: Synthetic

<400> SEQUENCE: 42
aagccccagt tggcagcttc ag                                             22

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
ctgaagctgc caactggggc tt                                             22

<210> SEQ ID NO 44
<211> LENGTH: 33
<212> TYPE: DNA
<213> ORGANISM: Artificial Sequence
<220> FEATURE:
<223> OTHER INFORMATION: Synthetic

<400> SEQUENCE: 44
tttttccatg gagagcacgt ctcagattat aaa                                 33

<210> SEQ ID NO 45
<211> LENGTH: 32
<212> TYPE: DNA
<213> ORGANISM: Artificial Sequence
<220> FEATURE:
<223> OTHER INFORMATION: Synthetic

<400> SEQUENCE: 45
tttttccatg gagagcaatt ctcagattcg aa                                  32

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
cacaggacaa gttggattcc t                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
aggaatccaa cttgtcctgt g                                              21

<210> SEQ ID NO 48
<211> LENGTH: 31
<212> TYPE: DNA
<213> ORGANISM: Artificial Sequence
<220> FEATURE:
<223> OTHER INFORMATION: Synthetic

<400> SEQUENCE: 48
tttttccatg gccctgcgcg ccctggaagg c                                   31

<210> SEQ ID NO 49

```
<211> LENGTH: 31
<212> TYPE: DNA
<213> ORGANISM: Artificial Sequence
<220> FEATURE:
<223> OTHER INFORMATION: Synthetic

<400> SEQUENCE: 49
tttttccatg gccctgtaat ccctggcggg c                                    31

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
gcagggtttg cctggggaag gtag                                            24

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ctaccttccc caggcaaacc ctgc                                            24

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
gtaggaaagt tcagggcaac ac                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
gtgttgccct gaactttcct ac                                              22

<210> SEQ ID NO 54
<211> LENGTH: 40
<212> TYPE: DNA
<213> ORGANISM: Artificial Sequence
<220> FEATURE:
<223> OTHER INFORMATION: Synthetic

<400> SEQUENCE: 54
ttttccatgg tcagatgcca gcatgatcac caggaatgcc                           40

<210> SEQ ID NO 55
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: The sequence is Biotin-labeled at 5' position

<400> SEQUENCE: 55
gccctgcgcg ccctggcg                                                    18

<210> SEQ ID NO 56
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 56
gcagagagaa gccacagga                                                   19

<210> SEQ ID NO 57
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 57
cctgcgcttt cctaccttcc c                                                21

<210> SEQ ID NO 58
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 58
gcagagagaa gccacagga                                                   19

<210> SEQ ID NO 59
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 59
tcagatgcca tcatgatcac c                                                21

<210> SEQ ID NO 60
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: The sequence is Biotin-labeled at 5' position

<400> SEQUENCE: 60
gtaagtggga tctggggagg a                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 61
tcctccccag atcccactta c                                              21

<210> SEQ ID NO 62
<211> LENGTH: 783
<212> TYPE: DNA
<213> ORGANISM: Homo sapiens

<400> SEQUENCE: 62
tctaaaaatg cccatcctct gaacaccatc tttgtgtagg catctggggg aggccagctg     60
gggtgaggtc atctgccagc caggcccgta ggacttggcg cttcttgttt atcacagcca    120 catgtgggc cactgccagg gcccgcccca actctgcagt cattggagga gcttgaagtt    180
aaagactcct gctaaaaacc agtacgtttc attttgcagt tactgggagg gggcttgctg    240
tggccctgtc aggaagagta gagctctggt ccagctccgc gcaggaggg aggctgtcac    300 catgccggcc tgctgcagct gcagtgatgt tttccagtat gagacgaaca aagtcactcg    360
gatccagagc atgaattatg caccattaa gtggttcttc cacgtgatca tcttttccta    420
cgtttggtaa gtgggatctg ggaggaccc agatctctgc agtggccgac agcacagaaa    480
gccccagcgg gcagcttcag gtgcacattc tgaatctcac atggttttcg aatctgagac    540
gtgctctcac agccagctgg gcgggaggga ggaagcagca gcaggcaaga ggaaacggtg    600
ccaggctgca gcagagagaa gccacaggac aagcgggatt cctttctgct ctacttcagg    660
cccgccaggg cgcgcagggc agggcgtgcc tggggaaggt aggaaagcgc agggcaacac    720
cctggatccc cagggaggag gcgaggatct cagggcacgc ctggtgatca tgctggcatc    780
tga                                                                 783

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
tgttgtggtt ttgttaggaa gagta                                          25

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64

-continued

```
aaaaatctaa atcctcccca aatc                                              24

<210> SEQ ID NO 65
<211> LENGTH: 22
<212> TYPE: DNA
<213> ORGANISM: Artificial Sequence
<220> FEATURE:
<223> OTHER INFORMATION: Synthetic

<400> SEQUENCE: 65
ggatttgggg aggatttaga tt                                                22

<210> SEQ ID NO 66
<211> LENGTH: 22
<212> TYPE: DNA
<213> ORGANISM: Artificial Sequence
<220> FEATURE:
<223> OTHER INFORMATION: Synthetic

<400> SEQUENCE: 66
caacctaaca ccgtttcctc tt                                                22

<210> SEQ ID NO 67
<211> LENGTH: 25
<212> TYPE: DNA
<213> ORGANISM: Artificial Sequence
<220> FEATURE:
<223> OTHER INFORMATION: Synthetic

<400> SEQUENCE: 67
gggagggagg aagtagtagt aggta                                             25

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
tcaaatacca acataatcac caaac                                             25

<210> SEQ ID NO 69
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The sequence is Biotin-labeled at 5' position

<400> SEQUENCE: 69
gcagagagaa gccacagga                                                    19
```